US007970458B2

(12) United States Patent  (10) Patent No.: US 7,970,458 B2
Norris et al.  (45) Date of Patent: Jun. 28, 2011

(54) INTEGRATED DISEASE DIAGNOSIS AND TREATMENT SYSTEM

(75) Inventors: Peter E. Norris, Cambridge, MA (US); Feiling Wang, Medford, MA (US); Xiao-Li Li, Lexington, MA (US)

(73) Assignee: Tomophase Corporation, Burlington, MA (US)

( * ) Notice: Subject to any disclaimer, the term of this patent is extended or adjusted under 35 U.S.C. 154(b) by 1566 days.

(21) Appl. No.: 11/253,242

(22) Filed: Oct. 17, 2005

(65) Prior Publication Data

US 2006/0079762 A1  Apr. 13, 2006

Related U.S. Application Data

(63) Continuation-in-part of application No. 10/963,948, filed on Oct. 12, 2004, now Pat. No. 7,263,394, and a continuation-in-part of application No. 11/244,418, filed on Oct. 4, 2005.

(60) Provisional application No. 60/620,793, filed on Oct. 20, 2004.

(51) Int. Cl.
    *A61B 6/00* (2006.01)
(52) U.S. Cl. ........ 600/478; 600/473; 600/476; 356/511; 356/342; 356/453; 356/287
(58) Field of Classification Search .................. 600/473, 600/476, 478; 356/511, 342, 453, 287
    See application file for complete search history.

(56) References Cited

U.S. PATENT DOCUMENTS

| 4,402,311 A | 9/1983 | Hattori |
| 4,848,867 A | 7/1989 | Kajioka et al. |
| 4,878,492 A | 11/1989 | Sinofsky et al. |
| 4,991,938 A | 2/1991 | Buhrer et al. |
| 5,088,493 A | 2/1992 | Giannini et al. |
| 5,202,745 A | 4/1993 | Sorin et al. |
| 5,321,501 A | 6/1994 | Swanson et al. |
| 5,459,570 A | 10/1995 | Swanson et al. |
| 5,659,392 A | 8/1997 | Marcus et al. |
| 5,710,630 A | 1/1998 | Essenpreis et al. |
| 5,784,162 A | 7/1998 | Cabib et al. |
| 5,803,909 A | 9/1998 | Maki et al. |
| 5,912,762 A | 6/1999 | Li et al. |
| 6,034,774 A | 3/2000 | Marcus et al. |
| 6,134,003 A | 10/2000 | Tearney et al. |

(Continued)

FOREIGN PATENT DOCUMENTS

CN  2524241  12/2002

(Continued)

OTHER PUBLICATIONS

El-Tonsy, M.H., et al., "Continuous-wave Nd:Yag laser hyperthermia: a successful modality in treatment of basal cell carcinoma," *Dermatology Online Journal*, 10(2):12 pages, Oct. 2004.

(Continued)

*Primary Examiner* — Tse Chen
*Assistant Examiner* — Joel F Brutus
(74) *Attorney, Agent, or Firm* — Perkins Coie LLP

(57) ABSTRACT

Designs, implementations, and techniques for optically measuring a sample and integrated systems that provide CT-scan, optical probing and therapy by electromagnetic radiation treatment (e.g. laser, RF, or microwave). Light at different wavelength bands may be used to detect different absorption features in the sample. Multiple light sources may be used including tunable lasers.

18 Claims, 32 Drawing Sheets

U.S. PATENT DOCUMENTS

| | | | |
|---|---|---|---|
| 6,201,989 B1 | 3/2001 | Whitehead et al. | |
| 6,219,565 B1 | 4/2001 | Cupp et al. | |
| 6,246,818 B1* | 6/2001 | Fukushima | 385/47 |
| 6,252,666 B1 | 6/2001 | Mandella et al. | |
| 6,282,011 B1 | 8/2001 | Tearney et al. | |
| 6,377,840 B1 | 4/2002 | Gritsenko et al. | |
| 6,421,164 B2 | 7/2002 | Tearney et al. | |
| 6,451,009 B1 | 9/2002 | Dasilva et al. | |
| 6,485,413 B1 | 11/2002 | Boppart et al. | |
| 6,498,942 B1 | 12/2002 | Esenaliev et al. | |
| 6,501,551 B1 | 12/2002 | Tearney et al. | |
| 6,522,407 B2 | 2/2003 | Everett et al. | |
| 6,585,639 B1* | 7/2003 | Kotmel et al. | 600/116 |
| 6,608,717 B1 | 8/2003 | Medford et al. | |
| 6,609,425 B2* | 8/2003 | Ogawa | 73/608 |
| 6,615,072 B1 | 9/2003 | Izatt et al. | |
| 6,687,010 B1 | 2/2004 | Horii et al. | |
| 6,709,402 B2 | 3/2004 | Dekker | |
| 6,725,073 B1 | 4/2004 | Motamedi et al. | |
| 6,738,144 B1 | 5/2004 | Dogariu | |
| 6,753,966 B2 | 6/2004 | Von Rosenberg | |
| 6,847,453 B2 | 1/2005 | Bush | |
| 6,891,984 B2 | 5/2005 | Petersen et al. | |
| 6,901,284 B1 | 5/2005 | Maki et al. | |
| 6,903,820 B2 | 6/2005 | Wang et al. | |
| 6,903,854 B2 | 6/2005 | Gelikonov et al. | |
| 6,943,881 B2 | 9/2005 | Wang et al. | |
| 7,023,563 B2 | 4/2006 | Li | |
| 7,039,454 B1 | 5/2006 | Kaga et al. | |
| 7,058,155 B2 | 6/2006 | Piacsek et al. | |
| 7,207,984 B2 | 4/2007 | Farr et al. | |
| 7,254,429 B2 | 8/2007 | Schurman et al. | |
| 7,259,851 B2 | 8/2007 | Wang | |
| 7,263,394 B2 | 8/2007 | Wang | |
| 7,428,053 B2 | 9/2008 | Feldchtein et al. | |
| 7,456,965 B2 | 11/2008 | Wang | |
| 7,595,879 B2 | 9/2009 | Wang | |
| 7,831,298 B1 | 11/2010 | Wang et al. | |
| 2002/0049370 A1* | 4/2002 | Laufer et al. | 600/300 |
| 2002/0126347 A1 | 9/2002 | Hogan | |
| 2002/0131049 A1 | 9/2002 | Schmitt | |
| 2003/0020920 A1 | 1/2003 | Dave et al. | |
| 2003/0114878 A1 | 6/2003 | Diederich et al. | |
| 2003/0137669 A1 | 7/2003 | Rollins et al. | |
| 2003/0187319 A1 | 10/2003 | Kaneko et al. | |
| 2004/0001716 A1 | 1/2004 | Daou et al. | |
| 2004/0140425 A1 | 7/2004 | Iizuka et al. | |
| 2004/0218845 A1 | 11/2004 | Li et al. | |
| 2004/0246490 A1 | 12/2004 | Wang | |
| 2004/0247268 A1 | 12/2004 | Ishihara et al. | |
| 2004/0258377 A1 | 12/2004 | Berkey et al. | |
| 2004/0260158 A1 | 12/2004 | Hogan | |
| 2005/0018202 A1 | 1/2005 | Wang | |
| 2005/0053109 A1 | 3/2005 | Hogan | |
| 2005/0075547 A1 | 4/2005 | Wang et al. | |
| 2005/0286055 A1 | 12/2005 | Wang et al. | |
| 2006/0089548 A1 | 4/2006 | Hogan | |
| 2006/0100490 A1 | 5/2006 | Wang et al. | |
| 2007/0103683 A1 | 5/2007 | Wang et al. | |
| 2008/0030740 A1 | 2/2008 | Wang | |
| 2008/0033300 A1 | 2/2008 | Hoang et al. | |
| 2008/0267562 A1 | 10/2008 | Wang | |
| 2009/0073444 A1 | 3/2009 | Wang | |

FOREIGN PATENT DOCUMENTS

| | | |
|---|---|---|
| EP | 0 429 297 | 5/1991 |
| EP | 0 527 050 | 2/1993 |
| JP | 2001066245 A | 3/2001 |
| JP | 2002013907 A | 1/2002 |
| JP | 2004-317437 | 11/2004 |
| WO | 03/062802 | 7/2003 |
| WO | 2005/001522 | 1/2005 |
| WO | 2006/041997 | 4/2006 |
| WO | 2006/045013 | 4/2006 |
| WO | 2008/134449 | 11/2008 |
| WO | 2009/108950 | 9/2009 |

OTHER PUBLICATIONS

Goldberg, S.N., et al., "Thermal ablation therapy for focal malignancy: a unified approach to underlying principles, techniques, and diagnostic imaging guidance," *AJR American Journal Roentgenology*, 174(2):323-331, Feb. 2000.

*Handbook of Optics*, 2nd Edition, vol. 1: Fundamentals, Techniques, & Design, Optical Society of America, McGraw-Hill Professional, pp. 42.68-42.73, Sep. 1994.

James, A., et al., "Airway smooth muscle in health and disease; methods of measurement and relation to function," *The European Respiratory Journal*, 15(4):782-789, Apr. 2000.

Lucroy, M.D., et al., "Selective laser-induced hyperthermia for the treatment of spontaneous tumors in dogs," *Journal of X-Ray Science and Technology*, 10(3-4):237-243, (2002).

Miller, J.D., et al., "A Prospective Feasibility Study of Bronchial Thermoplasty in the Human Airway," *Chest*, 127(6):1999-2006, Jun. 2005.

Nikfarjam, M., et al., "Interstitial laser thermotherapy for liver tumours," *British Journal of Surgery*, 90(9):1033-1047, Sep. 2003.

Ziemann, V., et al., "Ideas for an interferometric thermometer," *Nuclear Instruments and Methods in Physics Research Section A: Accelerators, Spectrometers, Detectors and Associated Equipment*, 564(1):587-589, Aug. 2006.

International Preliminary Report on Patentability dated Feb. 24, 2009 for PCT/US05/35951 (9 pages).

International Search Report and Written Opinion dated Aug. 29, 2008 for PCT/US05/35951 (10 pages).

International Search Report and Written Opinion dated Oct. 17, 2008 for PCT/US08/61451 (7 pages).

Office Action dated Mar. 17, 2010 for Japanese Patent Application No. 2006-515173 (4 pages).

Office Action dated Feb. 12, 2010 for Chinese Patent Application No. 200580043930.4 (12 pages).

International Search Report and Written Opinion for PCT/US05/37730, dated Oct. 4, 2007.

Tearney, G., et al., "In Vivo Endoscopic Optical Biopsy with Optical Coherence Tomography," *Science*, 276(5321):2037-2039, Jun. 1997.

Tumlinson, A., et al., "Endoscope-tip interferometer for ultrahigh resolution frequency domain optical coherence tomography in mouse colon," *Optics Express*, 14(5):1878-1887, Mar. 2006.

Vakhtin, A.B., et al., "Common-Path Interferometer for Frequency-Domain Optical Coherence Tomography," *Applied Optics*, 42(34):6953-6958, Dec. 2003.

Yun, S., et al., "Comprehensive volumetric optical microscopy in vivo," *Nature Medicine*, 12(12):1429-1433, Nov. 2006.

International Preliminary Report on Patentability dated Nov. 5, 2009 for International Application No. PCT/US2008/061451, filed Apr. 24, 2008 (6 pages).

International Search Report and Written Opinion dated Nov. 20, 2009 for International Application No. PCT/US2009/035773, filed Mar. 2, 2009 (7 pages).

International Preliminary Report on Patentability for PCT/US04/17649, dated Dec. 22, 2005.

Office Action dated Nov. 20, 2009 for Chinese Patent Application No. 200480021343.0 (25 pages).

European Search Report dated Nov. 18, 2010 for European Patent Application No. 05813935.3, filed Oct. 20, 2005 (9 pages).

Office Action dated Oct. 22, 2010 for Canadian Patent Application No. 2,528,417 (3 pages).

European Search Report dated Nov. 2, 2010 for European Patent Application No. 04754292.3, filed Jun. 4, 2004 (4 pages).

\* cited by examiner

Prior Art

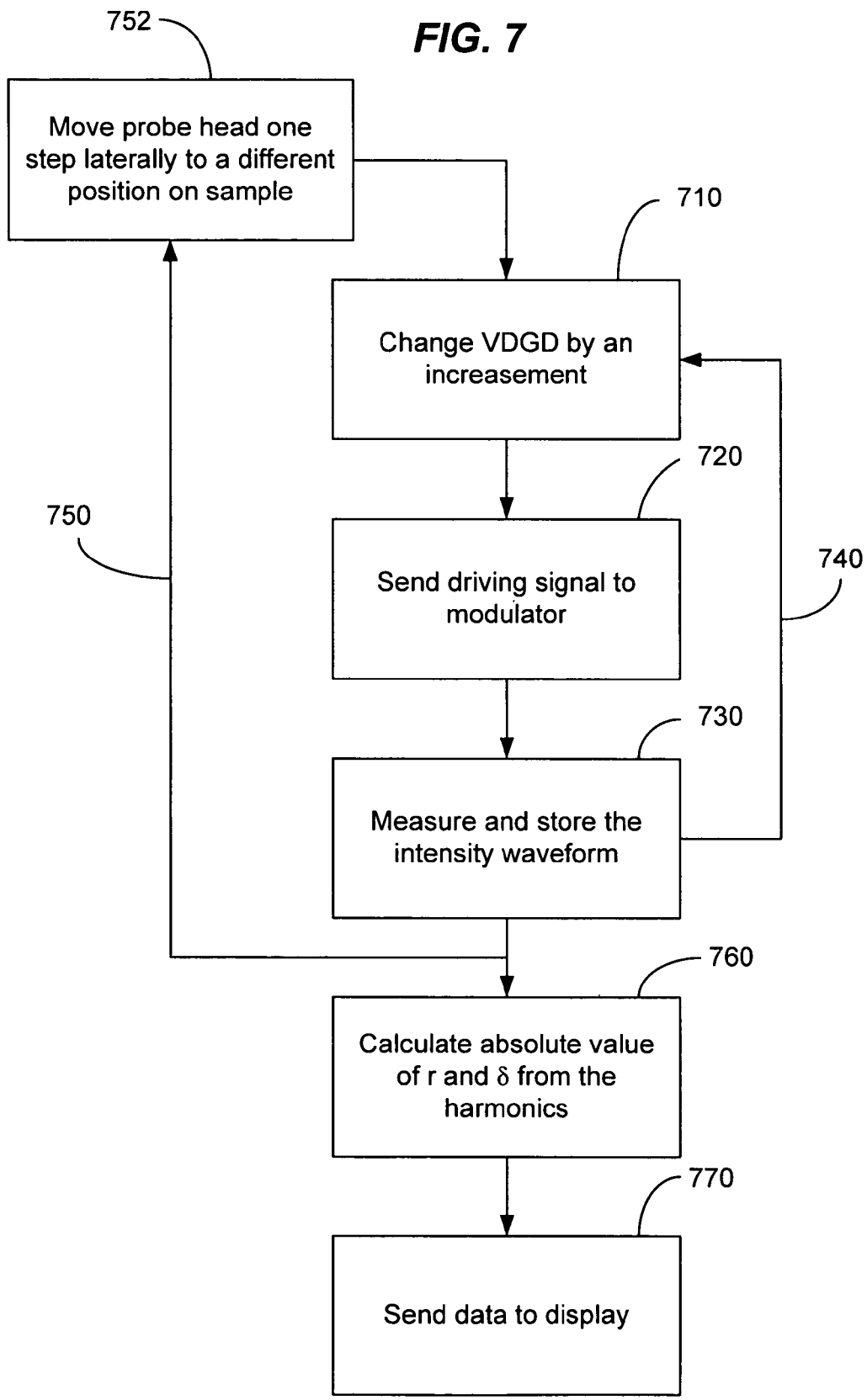

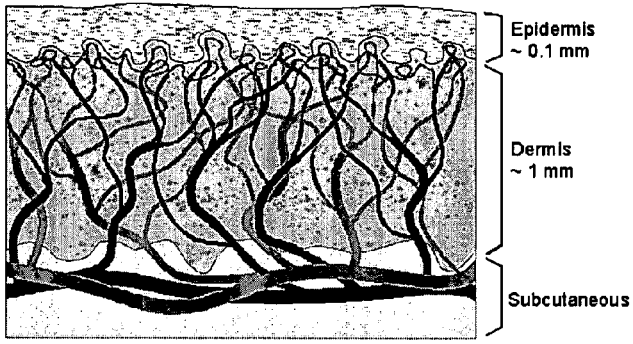
FIG. 19A
FIG. 19B
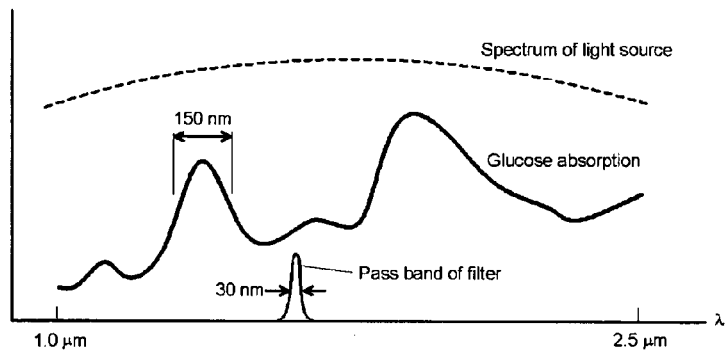
FIG. 20
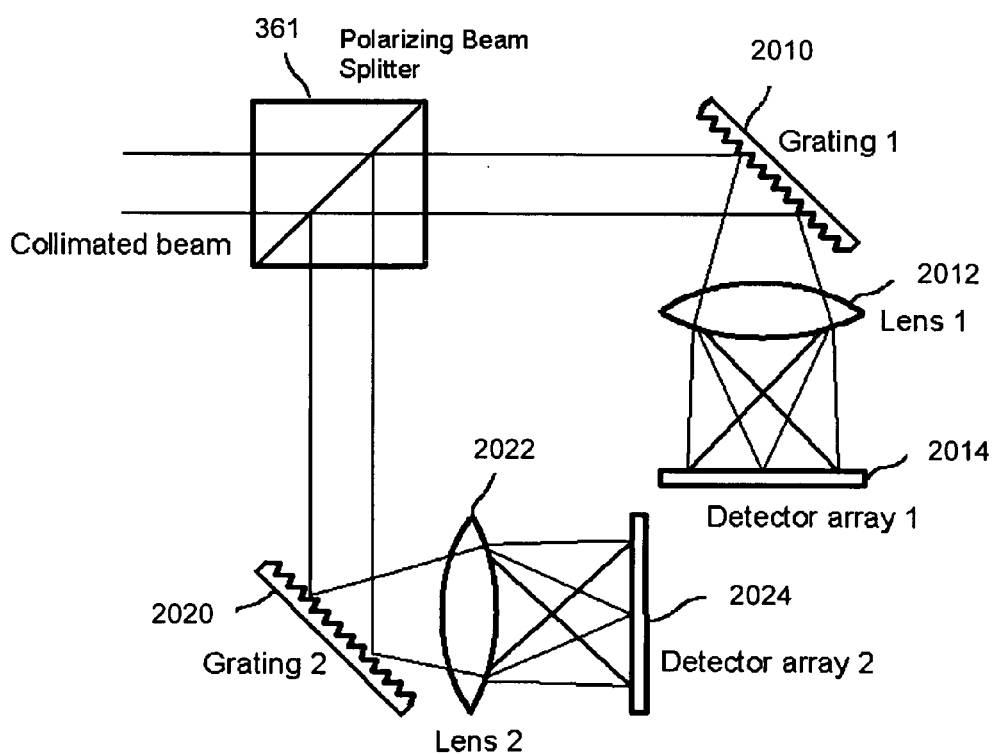

INTEGRATED DISEASE DIAGNOSIS AND TREATMENT SYSTEM

This application claims the benefit of the U.S. Provisional Patent Application Ser. No. 60/620,793 entitled "Early-Stage Lung Cancer Diagnosis and Treatment System" and filed on Oct. 20, 2004.

This application is a continuation-in-part application of and claims the benefit of U.S. application Ser. No. 10/963,948 entitled "Coherence-Gated Optical Glucose Monitor" and filed on Oct. 12, 2004 now U.S. Pat. No. 7,263,394 which was published as U.S. patent publication No. US-2005-0075547-A1 on Apr. 7, 2005.

This application is also a continuation-in-part application of and claims the benefit of pending U.S. application Ser. No. 11/244,418 entitled "Cross-Sectional Mapping of Spectral Absorbance Features" and filed on Oct. 4, 2005.

The entire disclosures of the above-referenced patent applications are incorporated herein by reference as part of the specification of this application.

BACKGROUND

This application relates to devices and techniques for non-invasive optical probing of various substances, and devices, systems and methods for detecting, diagnosing and treating lung disease using the non-invasive optical probing.

Investigation of substances by non-invasive and optical means has been the object of many studies as inhomogeneity of light-matter interactions in substances can reveal their structural, compositional, physiological and biological information. Various devices and techniques based on optical coherence domain reflectometry (OCDR) may be used for non-invasive optical probing of various substances, including but not limited to skins, body tissues and organs of humans and animals, to provide tomographic measurements of these substances.

In many OCDR systems, the light from a light source is split into a sampling beam and a reference beam which propagate in two separate optical paths, respectively. The light source may be partially coherent source. The sampling beam is directed along its own optical path to impinge on the substances under study, or sample, while the reference beam is directed in a separate path towards a reference surface. The beams reflected from the sample and from the reference surface are then brought to overlap with each other to optically interfere. Because of the wavelength-dependent phase delay the interference results in no observable interference fringes unless the two optical path lengths of the sampling and reference beams are very similar. This provides a physical mechanism for ranging. A beam splitter may be used to split the light from the light source and to combine the reflected sampling beam and the reflected reference beam for detection at an optical detector. This use of the same device for both splitting and recombining the radiation is essentially based on the well-known Michelson interferometer. The discoveries and the theories of the interference of partially coherent light are summarized by Born and Wolf in "Principles of Optics", Pergamon Press (1980).

Low-coherence light in free-space Michelson interferometers was utilized for measurement purposes. Optical interferometers based on fiber-optic components were used in various instruments that use low-coherence light as means of characterizing substances. Various embodiments of the fiber-optic OCDR exist such as devices disclosed by Sorin et al in U.S. Pat. No. 5,202,745, by Marcus et al in U.S. Pat. No. 5,659,392, by Mandella et al in U.S. Pat. No. 6,252,666, and by Tearney et al in U.S. Pat. No. 6,421,164. The application of OCDR in medical diagnoses in certain optical configurations has come to be known as "optical coherence tomography" (OCT).

FIG. 1 illustrates a typical optical layout used in many fiber-optic OCDR systems described in U.S. Pat. No. 6,421,164 and other publications. A fiber splitter is attached to two optical fibers that respectively guide the sampling and reference beams in a Michelson configuration. Common to many of these and other implementations, the optical radiation from the low-coherence source is first physically separated into two separate beams where the sampling beam travels in a sample waveguide to interact with the sample while the reference beam travels in a reference waveguide. The fiber splitter than combines the reflected radiation from the sample and the reference light from the reference waveguide to cause interference.

SUMMARY

This application describes devices, systems and techniques that use non-invasive optical probing and integrated medical diagnosis and treatment systems and techniques based on the non-invasive optical probing. In one implementation, for example, an integrated diagnostic and treatment system is described to include a CT scan unit to locate ailing areas in a body part, a referenced cross-sectional imaging unit to analyze each ailing area, and a laser, RF or microwave irradiation therapy unit to treat a selected ailing area. In another implementation, this application describes an integrated diagnostic/therapeutic system for lung cancer treatment which includes a CT scan unit to locate pulmonary nodule locations; a referenced cross-sectional imaging unit to analyze each pulmonary nodule location; and a laser irradiation therapy unit to optically treat a selected pulmonary nodule location. In yet another implementation, an integrated diagnostic and treatment system is described to include a CT scan unit to locate pulmonary nodule locations; a referenced cross-sectional imaging unit to analyze each pulmonary nodule location; and a microwave ablation therapy unit to treat a selected pulmonary nodule location.

Specific implementations of the above systems and devices are also described. In one example, a medical device includes a bronchoscope comprising a working channel configured for insertion into a passage of a body to reach a target area inside the body; an optical fiber probe module comprising (1) a probe optic fiber having a portion inserted into the working channel of the bronchoscope and (2) an optical probe head coupled to an end of the probe optic fiber and located inside the working channel, the optical fiber probe device operable to direct probe light to and collect reflected light from the target area in the body through the probe optic fiber and the optical probe head and to further obtain information of the target area from the collected reflected light; and a laser therapy module comprising a power delivery optic fiber having a portion inserted into the working channel of the bronchoscope to deliver a treatment laser beam to the target area.

A method for diagnosing and treating a malignant condition of a patient is also described to include performing a computed tomography (CT) scan in a selected body part of the patient to identify locations in the selected body part that are potentially malignant; using an optical probe beam to optically probe the identified locations to further identify malignant locations from benign locations; and delivering radiation energy to each identified malignant location to treat a malignant condition.

This application also describes methods and apparatus for the acquisition of optical spectral absorbance features and their distribution in the cross sections of tissues and other samples using multiple light sources emitting light centered at different wavelengths. In one example, a method for optically measuring a sample is described, where different light sources emitting light at different wavelengths are used to measure the sample. The light at each and every wavelength from the different light sources is directed through a single, common waveguide in a first propagation mode to one sampling location of a sample. The first portion of the guided light in the first propagation mode at a location near the sample is directed away from the sample before the first portion reaches the sample while allowing a second portion in the first propagation mode to reach the sample. A reflection of the second portion from the sample is directed to be in a second propagation mode different from the first propagation mode to produce a reflected second portion. Both the reflected first portion in the first propagation mode and the reflected second portion in the second propagation mode are then directed through the single waveguide. A relative delay between the reflected first portion and the reflected second portion received from the single waveguide is produced. The relative delay between the reflected first portion and the reflected second portion received from the single waveguide are adjusted at two different bias values to select a layer of material inside the sample to measure an optical absorption of the selected layer at each and every wavelength from the different light sources. The light at each and every wavelength from the different light sources is directed through the single waveguide to other sampling locations of the sample to measure the optical absorption of the selected layer at each and every wavelength from the different light sources at each of the sampling locations.

In another example, a device is described to include radiation sources to produce radiation beams at different wavelengths, respectively. A multiplexer is used to receive the radiation beams from the radiation sources and to combine the radiation beams to propagate along a common path. A delivery module is used to direct a part of the combined radiation to a sample and to collect reflected radiation from the sample while reflecting the radiation that does not reach the sample in its vicinity. This device also includes a controllable differential delay device to receive both the reflected radiation from the sample and reflected radiation that does not reach the sample. A demultiplexer is included in this device to receive radiation from the differential delay device and to separate received radiation into a plurality of beams at different wavelengths. The device further includes radiation detectors positioned to respectively receive the beams from the demultiplexer.

In another example, a device described in this application includes means for combining and guiding optical radiation from a plurality of light sources, each emitting at wavelengths within a spectral band different from others, towards a sample through a common optical waveguide; means for reflecting a first portion of the combined radiation away from the sample at its vicinity while directing a second portion of the combined radiation to reach the sample; means for collecting and guiding at least part of the reflected first portion and at least part of a reflected second portion from the sample towards a detection module through the common optical waveguide; means for separating the light into a plurality of spectral bands corresponding to emitting spectral bands of the light sources; and means for directing light radiation of the separated spectral bands to a plurality of light detectors, respectively.

This application also describes an example of a device for optically measuring a sample to include light sources emitting light at different wavelength bands centered at different wavelengths, a single waveguide to receive and guide the light at the different wavelength bands in a first propagation mode, and a probe head coupled to the waveguide to receive the light from the waveguide and to reflect a first portion of the light back to the waveguide in the first propagation mode and direct a second portion of the light to a sample. The probe head collects reflection of the second portion from the sample and exports to the waveguide the reflection as a reflected second portion in a second propagation mode different from the first propagation mode. This device also includes an optical differential delay unit to produce and control a relative delay between the first propagation mode and the second propagation mode in response to a control signal, and a detection module to receive the reflected light radiation in the first and second propagation modes to extract information of the sample carried by the reflected light in the second propagation mode and a control unit. The control unit produces the control signal to the optical differential delay unit and sets the relative delay at two different bias values to select a layer of material inside the sample to measure an optical absorption of the selected layer at each and every wavelength from the different light sources. In one implementation, the detection module may be configured to include an optical device to convert a part of received light in the first propagation mode and a part of received light in the second propagation mode into light in a third propagation mode that propagates along a first optical path. This optical device also converts remaining portions of the received light in the first and the second propagation modes into light in a fourth propagation mode that propagates along a second, different optical path. The detection module also includes a first optical element in the first optical path to separate light at different wavelength bands into a first set of different beams, first light detectors to respectively receive and detector the first set of different beams from the first optical element, a second optical element in the second optical path to separate light at different wavelength bands into a second set of different beams, and second light detectors to respectively receive and detector the second set of different beams from the second optical element.

In yet another example, a device for optically measuring a sample is described to include tunable laser sources emitting light at different wavelength bands centered at different wavelengths. A single waveguide is included to receive and guide the light at the different wavelength bands in a first propagation mode. A probe head is coupled to the waveguide to receive the light from the waveguide and to reflect a first portion of the light back to the waveguide in the first propagation mode and direct a second portion of the light to a sample. The probe head collects reflection of the second portion from the sample and exports to the waveguide the reflection as a reflected second portion in a second propagation mode different from the first propagation mode. A detection module is included to receive the reflected light in the first and the second propagation modes in the waveguide and to extract information of the sample carried by the reflected light in the second propagation mode. A control unit is also included to tune each tunable laser through a corresponding wavelength band to obtain absorption measurements of the sample at different wavelengths within each corresponding wavelength band.

The designs, techniques and exemplary implementations for non-invasive optical probing described in this application use the superposition and interaction of different optical modes propagating along substantially the same optical path inside one or more common optical waveguides. When one of the optical modes interacts with the substance under study, its superposition with the other mode can be used for the purpose of acquiring information about the optical properties of the substance.

The methods and apparatus described in this application are at least in part based on the recognition of various technical issues and practical considerations in implementing OCDR in commercially practical and user friendly apparatus, and various technical limitations in OCDR systems disclosed by the above referenced patents and other publications. As an example, at least one of disadvantages associated to the OCDR system designs shown in FIG. 1 or described in the aforementioned patents is the separation of the reference light beam from the sample light beam. Due to the separation of the optical paths, the relative optical phase or differential delay between the two beams may experience uncontrolled fluctuations and variations, such as different physical length, vibration, temperature, waveguide bending and so on. When the sample arm is in the form of a fiber-based catheter that is separate from the reference arm, for example, the manipulation of the fiber may cause a significant fluctuation and drift of the differential phase between the sample and reference light beams. This fluctuation and draft may adversely affect the measurements. For example, the fluctuation and drift in the differential phase between the two beams may lead to technical difficulties in phase sensitive measurements as absolute valuation of refractive indices and measurements of birefringence.

In various examples described in this application, optical radiation is not physically separated to travel different optical paths. Instead, all propagation waves and modes are guided along essentially the same optical path through one or more common optical waveguides. Such designs with the common optical path may be advantageously used to stabilize the relative phase among different radiation waves and modes in the presence of environmental fluctuations in the system such as variations in temperatures, physical movements of the system especially of the waveguides, and vibrations and acoustic impacts to the waveguides and system. In this and other aspects, the present systems are designed to do away with the two-beam-path configurations in various interferometer-based systems in which sample light and reference light travel in different optical paths. Implementations of the present systems may be configured to significantly reduce the fluctuations and drifts in the differential phase delay and to benefit some phase-sensitive measurements, such as the determination of the absolute reflection phase and birefringence. In addition, the techniques and devices described in this application simplify the structures and the optical configurations of devices for optical probing by using the common optical path to guide light.

In various applications, it may be beneficial to acquire the absorption characteristics of the material in an isolated volume inside the sample. In other case it may be desirable to map the distribution of some substances identifiable through their characteristic spectral absorbance. In some OCDR systems such as systems in aforementioned patents, it may be difficult to perform direct measurements of the optical inhomogeneity with regard to these and other spectral characteristics. The systems and techniques described in this application may be configured to allow for direct measurements of these and other spectral characteristics of a sample.

Exemplary implementations are described below to illustrate various features and advantages of the systems and techniques. One of such features is methods and apparatus for acquiring information regarding optical inhomogeneity in substance by a non-invasive means with the help of a low-coherence radiation. Another feature is to achieve high signal stability and high signal-to-noise ratio by eliminating the need of splitting the light radiation into a sample path and a reference path. Additional features include, for example, a platform on which phase-resolved measurements such as birefringence and absolute refractive indices can be made, capability of acquiring optical inhomogeneity with regard to the spectral absorbance, solving the problem of signal drifting and fading caused by the polarization variation in various interferometer-based optical systems, and an effective use of the source radiation with simple optical arrangements. Advantages of the systems and techniques described here include, among others, enhanced performance and apparatus reliability, simplified operation and maintenance, simplified optical layout, reduced apparatus complexity, reduced manufacturing complexity and cost.

Various exemplary methods and techniques for optically sensing samples are described. In some implementations, input light in two different optical propagation modes (e.g., the first and second modes) is directed through a common input optical path to the optical probe head which sends a portion of input light in the second mode to the sample. The probe head directs both the light in the first mode and the returned light from the sample in the second mode through a common optical path to a detection module.

For example, one method described here includes the following steps. Optical radiation in both a first propagation mode and a second, different propagation mode are guided through an optical waveguide towards a sample. The radiation in the first propagation mode is directed away from the sample without reaching the sample. The radiation in the second propagation mode is directed to interact with the sample to produce returned radiation from the interaction. Both the returned radiation in the second propagation mode and the radiation in the first propagation mode are coupled into the optical waveguide away from the sample. Next, the returned radiation in the second propagation mode and the radiation in the first propagation mode from the optical waveguide are used to extract information of the sample.

As another example, a device for optically measuring a sample is described to include a waveguide, a probe head, and a detection module. The waveguide supports a first propagation mode and a second, different propagation mode and is used to receive and guide an input beam in both the first and the second propagation modes. The probe head is coupled to the waveguide to receive the input beam and to reflect a first portion of the input beam in the first propagation mode back to the waveguide in the first propagation mode and direct a second portion of the input beam in the second propagation mode to a sample. The probe head collects reflection of the second portion from the sample and exports to the waveguide the reflection as a reflected second portion in the second propagation mode. The detection module is used to receive the reflected first portion and the reflected second portion in the waveguide and to extract information of the sample carried by the reflected second portion.

This application also describes devices that use one input waveguide to direct input light to the optical probe head and another output waveguide to direct output from the optical probe head. For example, a device for optically measuring a sample may include an input waveguide, which supports a first propagation mode and a second, different propagation mode, to receive and guide an input beam in both the first and the second propagation modes. The device may also include an output waveguide which supports the first and the second propagation modes. In this device, a probe head may be coupled to the input waveguide to receive the input beam and to the output waveguide, the probe head operable to direct a first portion of the input beam in the first propagation mode into the output waveguide in the first propagation mode and direct a second portion of the input beam in the second propagation mode to a sample. The probe head collects reflection of the second portion from the sample and exports to the output waveguide the reflection as a reflected second portion in the second propagation mode. In addition, a detection module may be included in this device to receive the reflected first portion and the reflected second portion in the output waveguide and to extract information of the sample carried by the reflected second portion.

In some other implementations, light in a single optical propagation mode, e.g., a first predetermined mode, is directed to an optical probe head near the sample under measurement. The optical probe head directs a first portion of the input light away from the sample in the first mode and a second portion of the input light to the sample. The optical probe head then directs returned light from the sample in a second, different mode to co-propagate along with the first portion in the first mode in a common optical path.

For example, one method for optically measuring a sample includes the following steps. A beam of guided light in a first propagation mode is directed to a sample. A first portion of the guided light in the first propagation mode is directed away from the sample at a location near the sample before the first portion reaches the sample. A second portion in the first propagation mode is directed to reach the sample. A reflection of the second portion from the sample is controlled to be in a second propagation mode different from the first propagation mode to produce a reflected second portion. Both the reflected first portion in the first propagation mode and the reflected second portion in the second propagation mode are then directed through a common waveguide into a detection module to extract information from the reflected second portion on the sample.

Another method for optically measuring a sample is also described. In this method, light in a first propagation mode is directed to a vicinity of a sample under measurement. A first portion of the light in the first propagation mode is then directed to propagate away from the sample at the vicinity of the sample without reaching the sample. A second portion of the light in the first propagation mode is directed to the sample to cause reflection at the sample. The reflected light from the sample is controlled to be in a second propagation mode that is independent from the first propagation mode to co-propagate with the first portion along a common optical path. The first portion in the first propagation mode and the reflected light in the second propagation mode are used to obtain information of the sample.

This application further describes exemplary implementations of devices and systems for optically measuring samples where optical probe heads receive input light in one mode and outputs light in two modes. One example of such devices includes a waveguide to receive and guide an input beam in a first propagation mode, and a probe head coupled to the waveguide to receive the input beam and to reflect a first portion of the input beam back to the waveguide in the first propagation mode and direct a second portion of the input beam to a sample. This probe head collects reflection of the second portion from the sample and exports to the waveguide the reflection as a reflected second portion in a second propagation mode different from the first propagation mode. This device further includes a detection module to receive the reflected first portion and the reflected second portion in the waveguide and to extract information of the sample carried by the reflected second portion.

In another example, an apparatus for optically measuring a sample is disclosed to include a light source, a waveguide supporting at least a first and a second independent propagation modes and guiding the light radiation from the light source in the first propagation mode to the vicinity of a sample under examination, a probe head that terminates the waveguide in the vicinity of the sample and reverses the propagation direction of a portion of the first propagation mode in the waveguide while transmitting the remainder of the light radiation to the sample, the probe head operable to convert reflected light from the sample into the second propagation mode, and a differential delay modulator that transmits the light in both the first and the second propagation modes from the probe head and the waveguide and varies the relative optical path length between the first and the second propagation modes. In this apparatus, a mode combiner is included to receive light from the differential delay modulator and operable to superpose the first and the second propagation modes by converting a portion of each mode to a pair of new modes. At least one photodetector is used in this apparatus to receive light in at least one of the two new modes. Furthermore, an electronic controller is used in communication with the photodetector and is operable to extract information of the sample from the output of the photodetector.

In yet another example, a device is described to include an optical waveguide, an optical probe head and an optical detection module. The optical waveguide is to guide an optical radiation in a first optical mode. The optical probe head is coupled to the optical waveguide to receive the optical radiation. The optical probe head is operable to (1) redirect a portion of the optical radiation back to the optical waveguide while transmitting the remaining radiation to a sample, (2) receive and direct the reflected or backscattered radiation from the sample into the waveguide, and (3) control the reflected or the backscattered light from the sample to be in a second optical mode different from the first optical mode. The optical detection module is used to receive the radiation redirected by the probe head through the waveguide and to convert optical radiation in the first and second optical modes, at least in part, into a common optical mode.

A further example of a device for optically measuring a sample includes an input waveguide, an output waveguide and a probe head. The input waveguide supports a first and a second different propagation modes and is used to receive and guide an input beam in the first propagation mode. The output waveguide supports a first and a second different propagation modes. The probe head is coupled to the input waveguide to receive the input beam and to the output waveguide to export light. The probe head is operable to direct a first portion of the input beam in the first propagation mode into the output waveguide and direct a second portion of the input beam to a sample. In addition, the probe head collects reflection of the second portion from the sample and exports to the output waveguide the reflection as a reflected second portion in the second propagation mode. Furthermore, this device includes a detection module to receive the reflected first portion and the reflected second portion in the output waveguide and to extract information of the sample carried by the reflected second portion.

This application also describes an example of an apparatus for optically measuring a sample. In this example, a first waveguide capable of maintaining at least one propagation mode is used. A light source that emits radiation is used to excite the propagation mode in the first waveguide. A light director is used to terminate the first waveguide with its first port, to pass the light mode entering the first port, at least in part, through a second port, and to pass the light modes entering the second port, at least in part, through a third port. The apparatus also includes a second waveguide that supports at least two independent propagation modes and having a first end coupled to the second port and a second end. Notably, a probe head is coupled to the second end of the second waveguide and operable to reverse the propagation direction of the light in part back to the second waveguide and to transmit the remainder to the sample. This probe head is operable to transform the collected light from the sample reflection to an orthogonal mode supported by the second waveguide and direct light in the orthogonal mode into the second waveguide. A third waveguide is also included which supports at least two independent propagation modes and is connected to the third port of the light director to receive light therefrom. A differential delay modulator is used to connect to the third waveguide to receive light from the second waveguide and imposes a variable phase delay and a variable path length on one mode in reference to the other. A fourth waveguide supporting at least two independent modes is coupled to the differential delay modulator to receive light therefrom. A detection subsystem is positioned to receive light from the fourth waveguide and to superpose the two propagation modes from the fourth waveguide to form two new modes, mutually orthogonal. This detection subsystem includes two photo-detectors respectively receiving light in the new modes.

Furthermore, this application describes optical sensing devices and systems that direct input light in a single propagation mode to the optical probe head and use the optical probe head to direct both light that does not reach the sample and light that is returned from the sample in the same mode and along a common propagation path which may be formed of one or more connected waveguides towards the detection module. For example, a device based on this aspect may include a waveguide which supports at least an input propagation mode of light, a probe head coupled to the waveguide, and a detection module. The waveguide is used to receive and guide an input beam in the input propagation mode. The probe head is used to receive the input beam and to reflect a first portion of the input beam back to the waveguide in the input propagation mode and direct a second portion of the input beam in the input propagation mode to a sample. The probe head collects reflection of the second portion from the sample and exports to the waveguide the reflection as a reflected second portion in the input propagation mode. The detection module is used to receive the reflected first portion and the reflected second portion in the input propagation mode from the waveguide and to extract information of the sample carried by the reflected second portion.

These and other features, system configurations, associated advantages, and implementation variations are described in detail in the attached drawings, the textual description, and the claims.

BRIEF DESCRIPTION OF THE DRAWINGS

FIG. 7 shows one exemplary operation of the described system in FIG. 5B or the system in FIG. 3 for acquiring images of optical inhomogeneity.

FIG. 19A illustrates an example of a human skin tissue where the optical sensing technique described here can be used to measure the glucose concentration in the dermis layer between the epidermis and the subcutaneous layers.

FIG. 19B shows some predominant glucose absorption peaks in blood in a wavelength range between 1 and 2.5 microns.

FIG. 20 illustrates one exemplary implementation of the detection subsystem in FIG. 3 where two diffraction gratings are used to separate different spectral components in the output light beams from the polarizing beam splitter.

DETAILED DESCRIPTION

Figure 1:
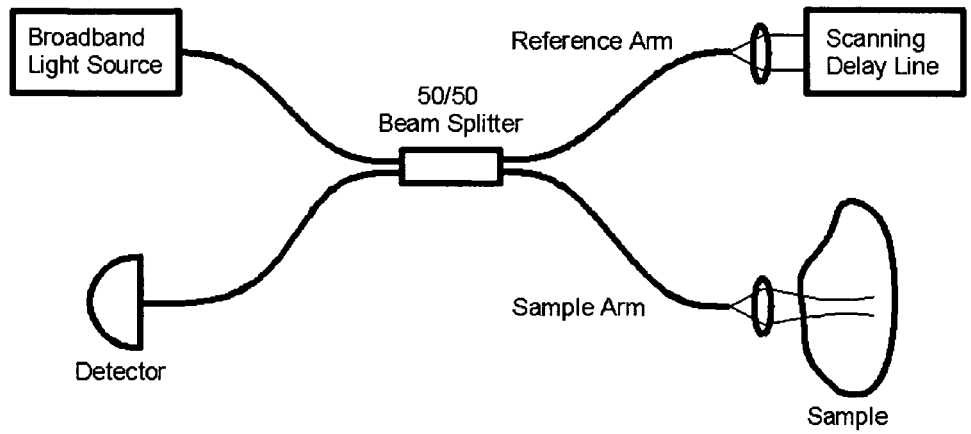
FIG. 1 shows an example of a conventional optical sensing device based on the well-known Michelson interferometer with reference and sample beams in two separate optical paths.

Lung cancer is one of the most deadly cancers in the United States. Patients with lung cancer have a relatively low 5-year survival rate of only 10-15% after diagnosis. The lung cancer in many patients is already in the second or third stage and has metastasized to other sites or organs by the time they begin to exhibit symptoms and seek medical treatment. Few are diagnosed in early stages where the survival rate can be much higher, approaching 85% for the stage 1 lung cancer. The conventional annual chest X-ray examination has not shown sufficient sensitivity to reveal the isolated, small (e.g., less than 1 centimeter in diameter) tumors typically found in the stage 1 lung cancer.

Recently, emphasis has shifted to early stage detection in major European and Japanese studies. In the US, a major new trial, the National Lung Screening Trial (NLST), has begun and is aimed at evaluating the efficacy of thoracic Computed Tomography (CT) scans in detecting early stage lung cancer. The NLST will compare a randomly selected group of high risk subjects (ex-smokers) who receive annual CT scans to a control group of subjects receiving chest x-rays.

The results of early studies have shown that thoracic CT scans often revealed a substantial number of solitary pulmonary nodules (SPNs). Biopsies have shown that approximately 80% or greater (e.g., 98%) of these SPNs were calcified and benign. However, the CT scan could not distinguish between calcified SPNs and active SPNs. The inability of the CT scans to distinguish malignancies from benign SPNs has led to a vigorous debate as to the efficacy of the CT scans in early screening for lung cancer.

A remedy to this defect of CT scans is to perform one or more pulmonary biopsies in order to further examine the nature of the SPNs identified by the CT scans. Pulmonary biopsies, however, can be risky. Statistics show that one in four pulmonary biopsies results in pneumothorax, a punctured lung. Also, the elderly and patients on blood thinners are at substantial risk of bleeding during pulmonary biopsies. In addition, pulmonary biopsies are relatively expensive. These and other factors have lead to search for alternative diagnostic methods to replace pulmonary biopsies.

The non-invasive optical probing techniques and devices described in this application may be used to detect and diagnose lung diseases in humans and animals including lung cancer. The optical probe head described in various implementations may be inserted into the lung to optically measure various parts of the lung without taking physical samples from the lung. The following sections first describe the specific implementations of non-invasive optical probing based on spectral responses of tissues or parts and interactions of different optical modes in the probe light. Next, examples of integrated lung disease diagnosis and treatment systems that combine CT scan with optical probing and laser treatment are described.

Spectral responses of materials and substances are important in many applications. For example, some distinct material properties are reflected in their spectral responses and can be detected or measured via the spectral responses. A detected or measured distinct property may be used for, e.g., identifying and locating a region or area such as a body part of a person or animal. Next, the identified body part may be further analyzed. As a more specific example, cancer tumors or other conditions can be detected and located using the measured spectral responses. Various non-invasive optical techniques described in this application may be used to measure spectral responses of a targeted body part of a person or animal. An optical probe head is used to scan a probing beam through the body part to optically measure the optical responses of the targeted body part to obtain a map. At each location within the targeted body part, light at different optical wavelengths is used to obtain optical absorption responses at these different wavelengths. Notably, the spectral absorption features of a target layer underneath the surface may be optically selected and measured by rejecting contributions to the reflected probe light made by the tissues outside the boundaries of the target layer.

In some implementations, a single broadband light source may be used for the acquisition of the spectral information within the emission spectral range of the light source. A tunable optical filter may be used to single out the spectral response of a narrow wavelength band within the emitted spectrum of the light source. When an absorbance feature to be measured or various targeted absorbance features in a body part under measured occupy a broad spectral range beyond the emission spectral bandwidth of a single light source, the light source may be implemented by combining two or more light sources for the acquisition of spectral absorbance mapping (SAM) in tissues and other samples.

The following sections first describe various techniques and devices for non-invasive optical probing using a single light source and then describe devices and techniques that combine two or more different light sources at different spectral ranges for the SAM measurements.

Energy in light traveling in an optical path such as an optical waveguide may be in different propagation modes. Different propagation modes may be in various forms. States of optical polarization of light are examples of such propagation modes. Two independent propagation modes do not mix with one another in the absence of a coupling mechanism. As an example, two orthogonally polarization modes do not interact with each other even though the two modes propagate along the same optical path or waveguide and are spatially overlap with each other. The exemplary techniques and devices described in this application use two independent propagation modes in light in the same optical path or waveguide to measure optical properties of a sample. A probe head may be used to direct the light to the sample, either in two propagation modes or in a single propagation modes, and receive the reflected or back-scattered light from the sample.

For example, one beam of guided light in a first propagation mode may be directed to a sample. A first portion of the first propagation mode may be arranged to be reflected before reaching the sample while a second portion in the first propagation mode is allowed to reach the sample. The reflection of the second portion from the sample is controlled in a second propagation mode different from the first propagation mode to produce a reflected second portion. Both the reflected first portion in the first propagation mode and the reflected second portion in the second propagation mode are directed through a common waveguide into a detection module to extract information from the reflected second portion on the sample.

In another example, optical radiation in both a first propagation mode and a second, different propagation mode may be guided through an optical waveguide towards a sample. The radiation in the first propagation mode is directed away from the sample without reaching the sample. The radiation in the second propagation mode is directed to interact with the sample to produce returned radiation from the interaction. Both the returned radiation in the second propagation mode and the radiation in the first propagation mode are coupled into the optical waveguide away from the sample. The returned radiation in the second propagation mode and the radiation in the first propagation mode from the optical waveguide are then used to extract information of the sample.

In these and other implementations based on the disclosure of this application, two independent modes are confined to travel in the same waveguide or the same optical path in free space except for the extra distance traveled by the probing light between the probe head and the sample. This feature stabilizes the relative phase, or differential optical path, between the two modes of light, even in the presence of mechanical movement of the waveguides. This is in contrast to interferometer sensing devices in which sample light and reference light travel in different optical paths. These interferometer sensing devices with separate optical paths are prone to noise caused by the variation in the differential optical path, generally complex in optical configurations, and difficult to operate and implement. The examples described below based on waveguides are in part designed to overcome these and other limitations.

Figure 2:
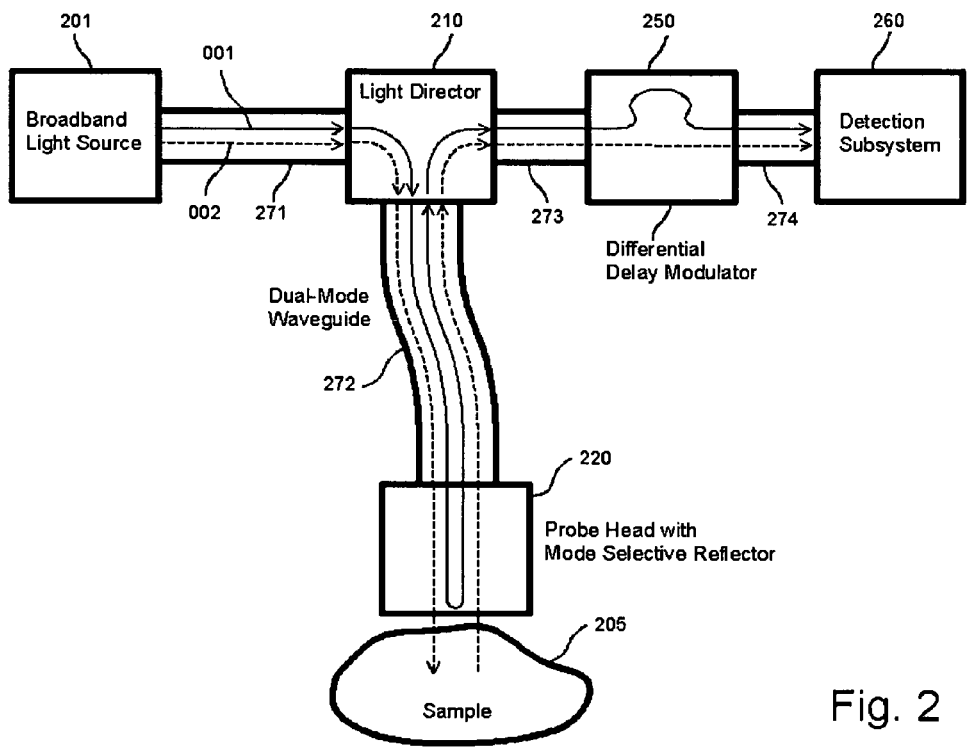
FIG. 2 shows one example of a sensing device according to one implementation.

FIG. 2 shows one example of a sensing device according to one implementation. This device directs light in two propagation modes along the same waveguide to an optical probe head near a sample 205 for acquiring information of optical inhomogeneity in the sample. A sample holder may be used to support the sample 205 in some applications. Light radiation from a broadband light source 201 is coupled into the first dual-mode waveguide 271 to excite two orthogonal propagation modes, 001 and 002. A light director 210 is used to direct the two modes to the second dual-mode waveguide 272 that is terminated by a probe head 220. The probe head 220 may be configured to perform at least the following functions. The first function of the probe head 220 is to reverse the propagation direction of a portion of light in the waveguide 272 in the mode 001; the second function of the probe head 220 is to reshape and deliver the remaining portion of the light in mode 002 to the sample 205; and the third function of the probe head 220 is to collect the light reflected from the sample 205 back to the second dual-mode waveguide 272. The back traveling light in both modes 001 and 002 is then directed by light director 210 to the third waveguide 273 and further propagates towards a differential delay modulator 250. The differential delay modulator 250 is capable of varying the relative optical path length and optical phase between the two modes 001 and 002. A detection subsystem 260 is used to superpose the two propagation modes 001 and 002 to form two new modes, mutually orthogonal, to be received by photo-detectors. Each new mode is a mixture of the modes 001 and 002.

The superposition of the two modes 001 and 002 in the detection subsystem 260 allows for a range detection. The light entering the detection subsystem 260 in the mode 002 is reflected by the sample, bearing information about the optical inhomogeneity of the sample 205, while the other mode, 001, bypassing the sample 205 inside probe head 220. So long as these two modes 001 and 002 remain independent through the waveguides their superposition in the detection subsystem 260 may be used to obtain information about the sample 205 without the separate optical paths used in some conventional Michelson interferometer systems.

For the simplicity of the analysis, consider a thin slice of the source spectrum by assuming that the amplitude of the mode 001 is $E_{001}$ in a first linear polarization and that of the mode 002 is $E_{002}$ in a second, orthogonal linear polarization in the first waveguide 271. The sample 205 can be characterized by an effective reflection coefficient r that is complex in nature; the differential delay modulator 250 can be characterized by a pure phase shift $\Gamma$ exerted on the mode 001. Let us now superpose the two modes 001 and 002 by projecting them onto a pair of new modes, $E_A$ and $E_B$, by a relative 45-degree rotation in the vector space. The new modes, $E_A$ and $E_B$, may be expressed as following:

$$\begin{cases} E_A = \frac{1}{\sqrt{2}}(e^{j\Gamma}E_{001} + rE_{002}); \\ E_B = \frac{1}{\sqrt{2}}(e^{j\Gamma}E_{001} + rE_{002}). \end{cases} \quad (1)$$

It is assumed that all components in the system, except for the sample 205, are lossless. The resultant intensities of the two superposed modes are $$\begin{cases} I_A = \frac{1}{2}[E_{001}^2 + E_{002}^2 + |r|E_{001}E_{002}\cos(\Gamma - \varphi)]; \\ I_B = \frac{1}{2}[E_{001}^2 + E_{002}^2 - |r|E_{001}E_{002}\cos(\Gamma - \varphi)], \end{cases} \quad (2)$$

where $\phi$ is the phase delay associated with the reflection from the sample. A convenient way to characterize the reflection coefficient r is to measure the difference of the above two intensities, i.e.

$$I_A - I_B = |r|E_{001}E_{002}\cos(\Gamma - \phi). \quad (3)$$

If Γ is modulated by the differential delay modulator 250, the measured signal, Eq. (3), is modulated accordingly. For either a periodic or a time-linear variation of Γ, the measured signal responds with a periodic oscillation and its peak-to-peak value is proportional to the absolute value of r.

For a broadband light source 201 in FIG. 2, consider the two phases, Γ and ϕ to be dependent on wavelength. If the two modes 001 and 002 experience significantly different path lengths when they reach the detection system 260, the overall phase angle, Γ–ϕ, should be significantly wavelength dependant as well. Consequently the measured signal, being an integration of Eq. (3) over the source spectrum, yields a smooth function even though Γ is being varied. The condition for a significant oscillation to occur in the measured signal is when the two modes 001 and 002 experience similar path lengths at the location of their superposition. In this case the overall phase angle, Γ–ϕ, becomes wavelength independent or nearly wavelength independent. In other words, for a given relative path length set by the modulator 250, an oscillation in the measured signal indicates a reflection, in the other mode, from a distance that equalizes the optical path lengths traveled by the two modes 001 and 002. Therefore the system depicted in FIG. 2 can be utilized for ranging reflection sources.

Due to the stability of the relative phase between the two modes, 001 and 002, phase-sensitive measurements can be performed with the system in FIG. 2 with relative ease. The following describes an exemplary method based on the system in FIG. 2 for the determination of the absolute phase associated with the radiation reflected from the sample 205.

In this method, a sinusoidal modulation is applied to the differential phase by the differential delay modulator 250, with a modulation magnitude of M and a modulation frequency of Ω. The difference in intensity of the two new modes is the measured and can be expressed as follows:

$$I_A - I_B = |r| E_{001} E_{002} \cos [M \sin(\Omega t) - \phi]. \quad (4)$$

It is clear from Eq. (4) that the measured exhibits an oscillation at a base frequency of Ω and oscillations at harmonic frequencies of the base frequency Ω. The amplitudes of the base frequency and each of the harmonics are related to ϕ and |r|. The relationships between r and the harmonics can be derived. For instance, the amplitude of the base-frequency oscillation and the second harmonic can be found from Eq. (4) to be:

$$A_\Omega = E_{001} E_{002} J_1(M) |r| \sin \phi; \quad (5a)$$

$$A_{2\Omega} = E_{001} E_{002} J_2(M) |r| \cos \phi, \quad (5b)$$

where $J_1$ and $J_2$ are Bessel functions of the first and second order, respectively. Eq. (5a) and (5b) can be used to solve for |r| and ϕ, i.e. the complete characterization of r. We can therefore completely characterize the complex reflection coefficient r by analyzing the harmonic content of various orders in the measured signal. In particular, the presence of the base-frequency component in the measured is due to the presence of ϕ.

Figure 3:
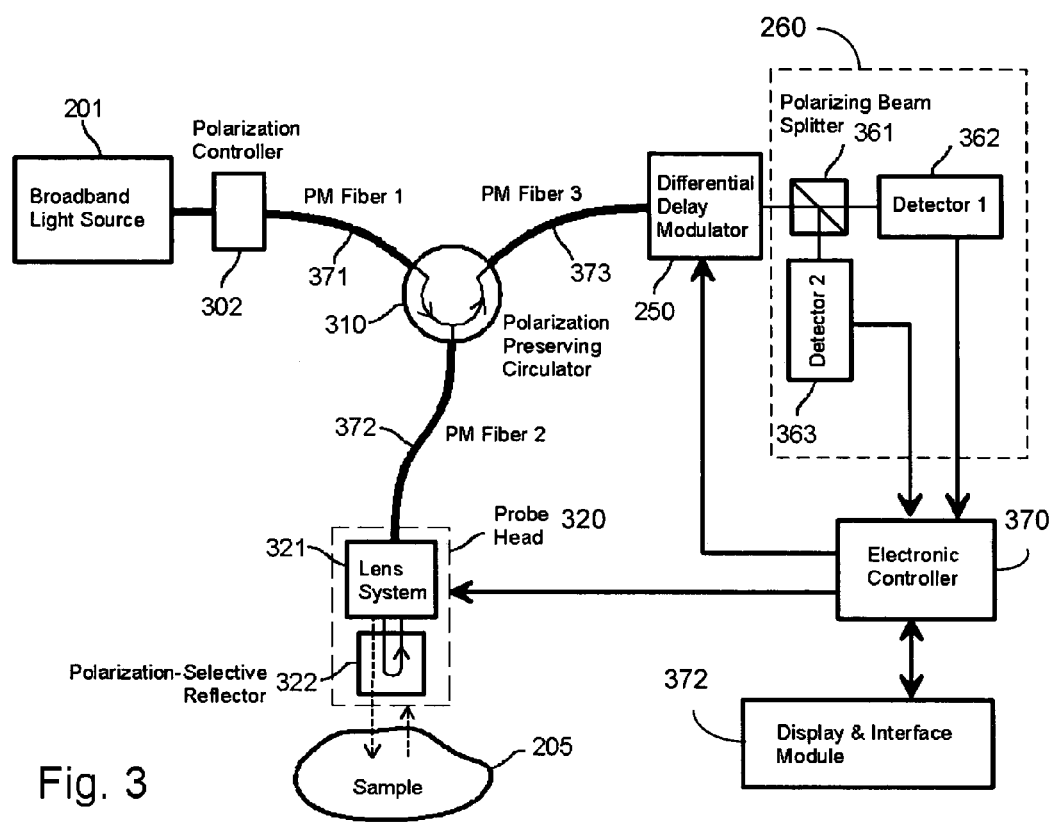
FIG. 3 shows an exemplary implementation of the system depicted in FIG. 2.

FIG. 3 shows an exemplary implementation of the system depicted in FIG. 2. The spectrum of source 201 may be chosen to satisfy the desired ranging resolution. The broader the spectrum is the better the ranging resolution. Various light sources may be used as the source 201. For example, some semiconductor superluminescent light emitting diodes (SLED) and amplified spontaneous emission (ASE) sources may possess the appropriate spectral properties for the purpose. In this particular example, a polarization controller 302 may be used to control the state of polarization in order to proportion the magnitudes of the two modes, 001 and 002, in the input waveguide 371. The waveguide 371 and other waveguides 372 and 373 may be dual-mode waveguides and are capable of supporting two independent polarization modes which are mutually orthogonal. One kind of practical and commercially available waveguide is the polarization maintaining (PM) optical fiber. A polarization maintaining fiber can carry two independent polarization modes, namely, the s-wave polarized along its slow axis and the p-wave polarized along its fast axis. In good quality polarization maintaining fibers these two modes can have virtually no energy exchange, or coupling, for substantial distances. Polarization preserving circulator 310 directs the flow of optical waves according to the following scheme: the two incoming polarization modes from fiber 371 are directed into the fiber 372; the two incoming polarization modes from fiber 372 are directed to the fiber 373. A polarization-preserving circulator 310 may be used to maintain the separation of the two independent polarization modes. For instance, the s-wave in the fiber 371 should be directed to the fiber 372 as s-wave or p-wave only. Certain commercially available polarization-preserving circulators are adequate for the purpose.

The system in FIG. 3 implements an optical probe head 320 coupled to the waveguide 372 for optically probing the sample 205. The probe head 320 delivers a portion of light received from the waveguide 372, the light in one mode (e.g., 002) of the two modes 001 and 002, to the sample 205 and collects reflected and back-scattered light in the same mode 002 from the sample 205. The returned light in the mode 002 collected from the sample 205 carries information of the sample 205 and is processed to extract the information of the sample 205. The light in the other mode 001 in the waveguide 372 propagating towards the probe head 320 is reflected back by the probe head 320. Both the returned light in the mode 002 and the reflected light in the mode 001 are directed back by the probe head 320 into the waveguide 372 and to the differential delay modulator 250 and the detection system 260 through the circulator 310 and the waveguide 373.

In the illustrated implementation, the probe head 320 includes a lens system 321 and a polarization-selective reflector (PSR) 322. The lens system 321 is to concentrate the light energy into a small area, facilitating spatially resolved studies of the sample in a lateral direction. The polarization-selective reflector 322 reflects the mode 001 back and transmits the mode 002. Hence, the light in the mode 002 transmits through the probe head 320 to impinge on the sample 205. Back reflected or scattered the light from the sample 205 is collected by the lens system 321 to propagate towards the circulator 310 along with the light in the mode 001 reflected by PSR 322 in the waveguide 372.

Figure 4:
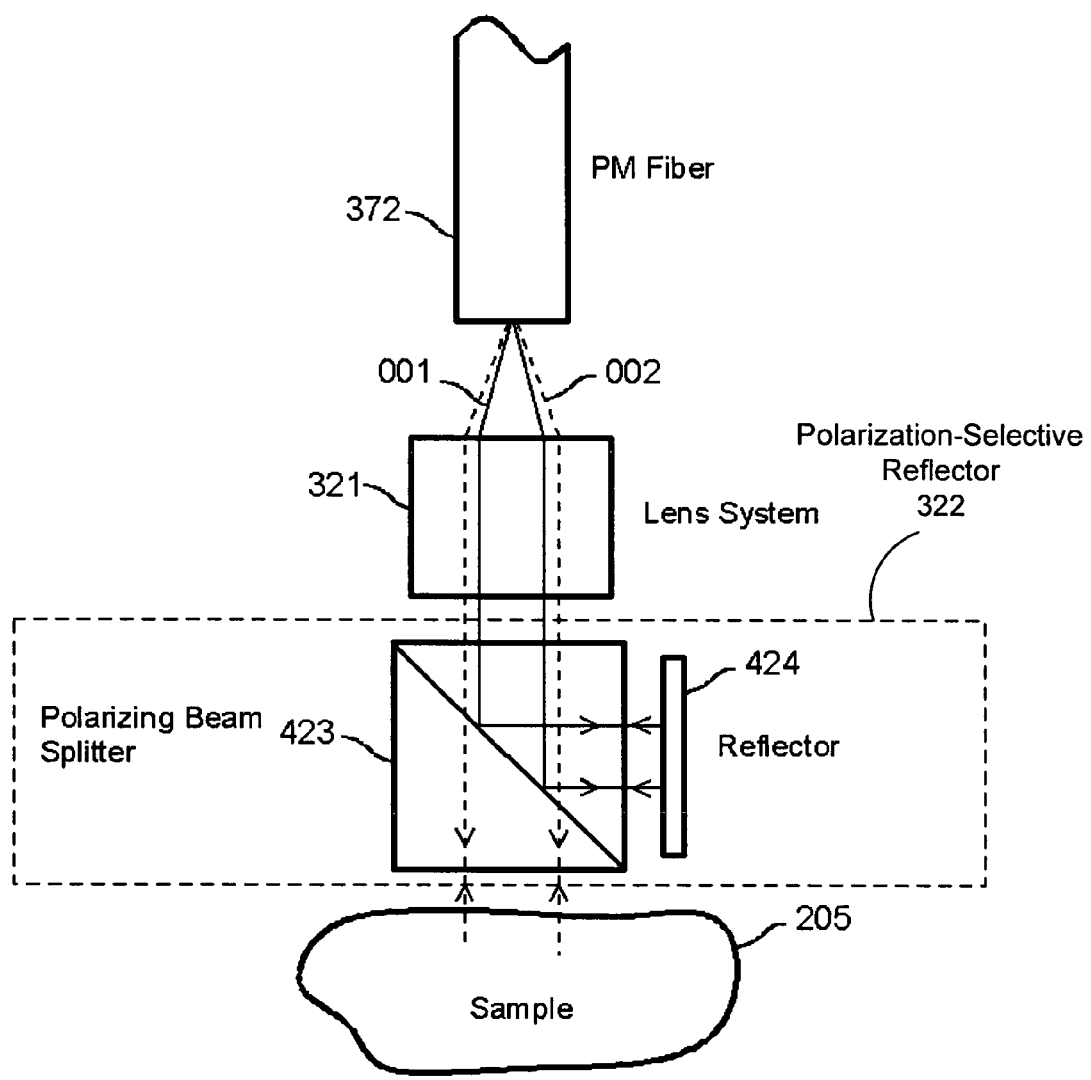
FIG. 4 shows one exemplary implementation of the probe head and one exemplary implementation of the polarization-selective reflector (PSR) used in FIG. 3.

FIG. 4 shows details of the probe head 320 and an example of the polarization-selective reflector (PSR) 322 according to one implementation. The PSR 322 includes a polarizing beam splitter (PBS) 423 and a reflector or mirror 424 in a configuration as illustrated where the PBS 423 transmits the selected mode (e.g., mode 002) to the sample 205 and reflects and diverts the other mode (e.g., mode 001) away from the sample 205 and to the reflector 424. By retro reflection of the reflector 424, the reflected mode 001 is directed back to the PBS 423 and the lens system 321. The reflector 424 may be a reflective coating on one side of beam splitter 423. The reflector 424 should be aligned to allow the reflected radiation to re-enter the polarization-maintaining fiber 372. The transmitted light in the mode 002 impinges the sample 205 and the light reflected and back scattered by the sample 205 in the mode 002 transmits through the PBS 423 to the lens system 321. The lens system 321 couples the light in both the modes 001 and 002 into the fiber 372.

In the implementation illustrated in FIG. 3, the detection system 260 includes a polarizing beam splitter 361, and two photodetectors 362 and 363. The polarizing beam splitter 361 is used to receive the two independent polarization modes 001 and 002 from the modulator 250 and superposes the two independent polarization modes 001 and 002. The beam splitter 361 may be oriented in such a way that, each independent polarization is split into two parts and, for each independent polarization mode, the two split portions possess the same amplitude. This way, a portion of the mode 001 and a portion of the mode 002 are combined and mixed in each of the two output ports of the beam splitter 361 to form a superposed new mode and each photodetector receives a superposed mode characterized by Eq. (1). The polarizing beam splitter 361 may be oriented so that the incident plane of its reflection surface makes a 45-degree angle with one of the two independent polarization mode, 001 or 002.

The system in FIG. 3 further implements an electronic controller or control electronics 370 to receive and process the detector outputs from the photodetectors 362 and 363 and to control operations of the systems. The electronic controller 370, for example, may be used to control the probe head 320 and the differential delay modulator 250. Differential delay modulator 250, under the control of the electronics and programs, generates a form of differential phase modulation as the differential path length scans through a range that matches a range of depth inside the sample 205. The electronic controller 370 may also be programmed to record and extract the amplitude of the oscillation in the measured signal characterized by Eq. (3) at various differential path lengths generated by the modulator 250. Accordingly, a profile of reflection as a function of the depth can be obtained as a one-dimensional representation of the sample inhomogeneity at a selected location on the sample 205.

For acquiring two-dimensional images of optical inhomogeneity in the sample 205, the probe head 320 may be controlled via a position scanner such as a translation stage or a piezo-electric positioner so that the probing light scans in a lateral direction, perpendicular to the light propagation direction. For every increment of the lateral scan a profile of reflection as a function of depth can be recorded with the method described above. The collected information can then be displayed on a display and interface module 372 to form a cross-sectional image that reveals the inhomogeneity of the sample 205.

In general, a lateral scanning mechanism may be implemented in each device described in this application to change the relative lateral position of the optical probe head and the sample to obtain a 2-dimensional map of the sample. A xy-scanner, for example, may be engaged either to the optical head or to a sample holder that holds the sample to effectuate this scanning in response to a position control signal generated from the electronic controller 370.

Figure 5A:
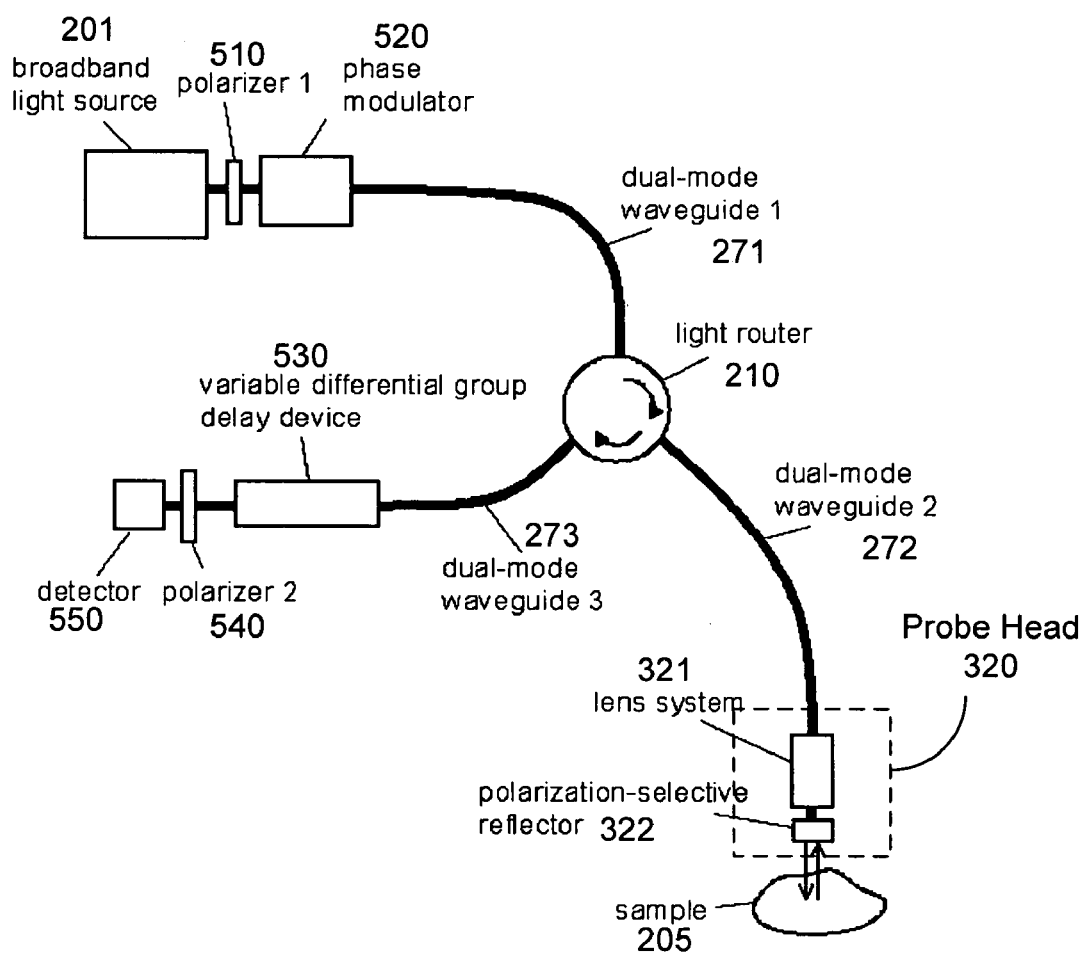
FIGS. 5A and 5B illustrate another exemplary optical sensing system that use three waveguides and a light director to direct light in two modes to and from the probe head in measuring a sample.
Figure 5B:
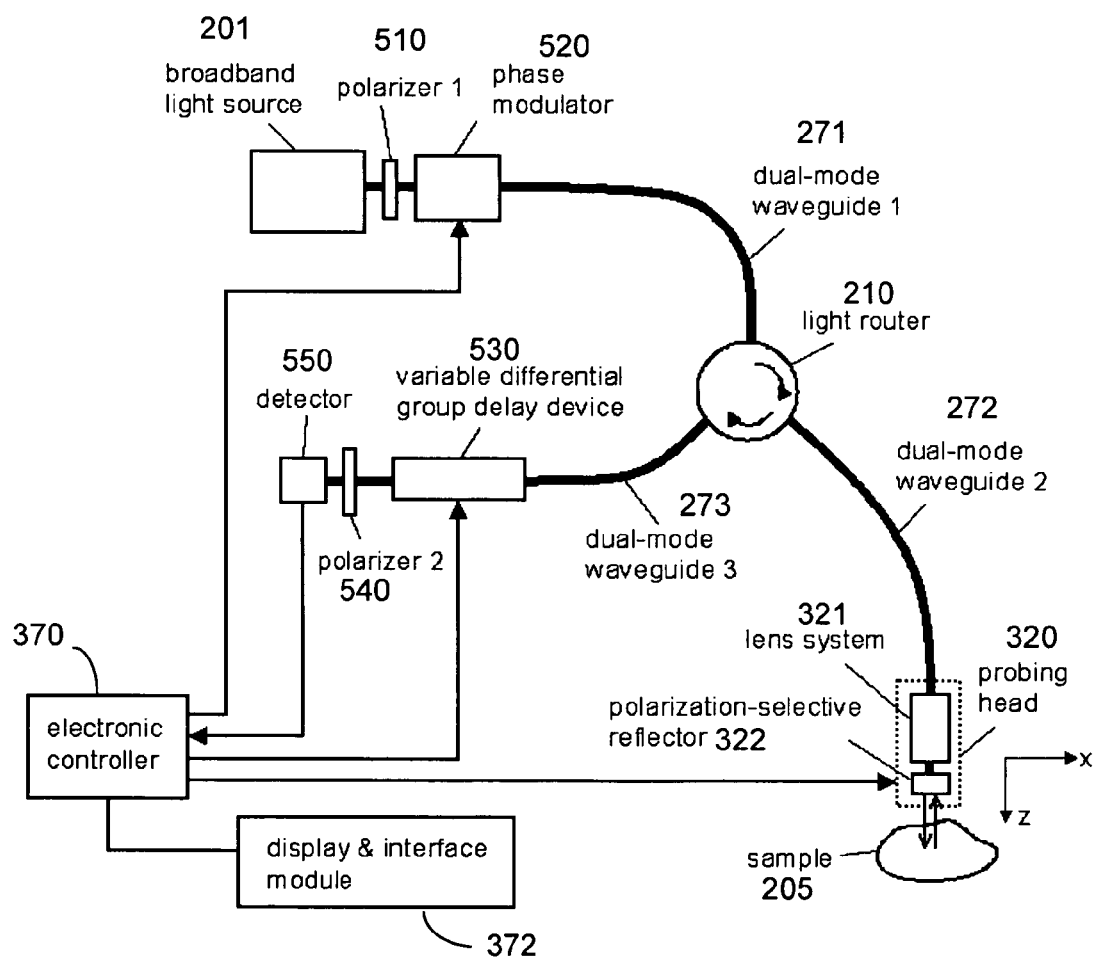

FIGS. 5A and 5B illustrate another exemplary system that use waveguides 271, 272, and 273 and a light director 210 to direct light in two modes to and from the probe head 320 in measuring the sample 205. A first optical polarizer 510 is oriented with respect to the polarization axes of the PM waveguide 271 to couple radiation from the broadband light source 201 into the waveguide 271 in two orthogonal linear polarization modes as the independent propagation modes. An optical phase modulator 520 is coupled in the waveguide 271 to modulate the optical phase of light in one guided mode relative to the other. A variable differential group delay (VDGD) device 530 is inserted in or connected to the waveguide 273 to introduce a controllable amount of optical path difference between the two waves. A second optical polarizer 540 and an optical detector 550 are used here to form a detection system. The second polarizer 540 is oriented to project both of the guided waves onto the same polarization direction so that the changes in optical path difference and the optical phase difference between the two propagation modes cause intensity variations, detectable by the detector 550.

The light from the source 201 is typically partially polarized. The polarizer 510 may be aligned so that maximum amount of light from the source 201 is transmitted and that the transmitted light is coupled to both of the guided modes in the waveguide 271 with the substantially equal amplitudes. The electric fields for the two orthogonal polarization modes S and P in the waveguide 271 can be expressed as:

$$\begin{cases} E_s = \frac{1}{\sqrt{2}} E, \\ E_p = \frac{1}{\sqrt{2}} E. \end{cases} \quad (6)$$

where the electric field transmitting the polarizer is denoted as E. It should be appreciated that the light has a finite spectral width (broadband or partially coherent). The fields can be described by the following Fourier integral:

$$E = \int E_\omega e^{j\omega t} d\omega. \quad (7)$$

For the simplicity of the analysis, a thin slice of the spectrum, i.e. a lightwave of a specific wavelength, is considered below. Without loosing generality, it is assumed that all the components, including polarizers, waveguides, Router, PSR and VDGD, are lossless. Let us designate the reflection coefficient of the sample r, that is complex in nature. The p-wave picks up an optical phase, $\Gamma$, relative to the s-wave as they reach the second polarizer 540:

$$\begin{cases} E_s = \frac{1}{\sqrt{2}} E, \\ E_p = \frac{1}{\sqrt{2}} r E e^{j\Gamma}. \end{cases} \quad (8)$$

The light that passes through Polarizer 540 can be expressed by $$E_a = \frac{1}{\sqrt{2}}(E_s + E_p) = \frac{1}{2}E(1 + re^{j\Gamma}). \quad (9)$$

The intensity of the light that impinges on the photodetector 550 is given by:

$$I = E_a E_a^* = \frac{1}{4}|E|^2[1 + |r|^2 + 2|r|\cos(\Gamma + \delta)]. \quad (10)$$

where phase angle $\delta$ reflects the complex nature of the reflection coefficient of the sample 205 and is defined by $$r = |r|e^{j\delta}. \quad (11)$$

Assuming the modulator 520 exerts a sinusoidal phase modulation, with magnitude M and frequency $\Omega$, in the p-wave with respect to the s-wave, the light intensity received by the detector 550 can be expressed as follows:

$$I = \frac{1+|r|^2}{4}|E|^2 + \frac{|r|}{2}|E|^2\cos[M\sin(\Omega t) + \varphi + \delta]. \quad (12)$$

where phase angle φ is the accumulated phase slip between the two modes, not including the periodic modulation due to the modulator 520. The VDGD 530 or a static phase shift in the modulator 520, may be used to adjust the phase difference between the two modes to eliminate φ.

Figure 6:
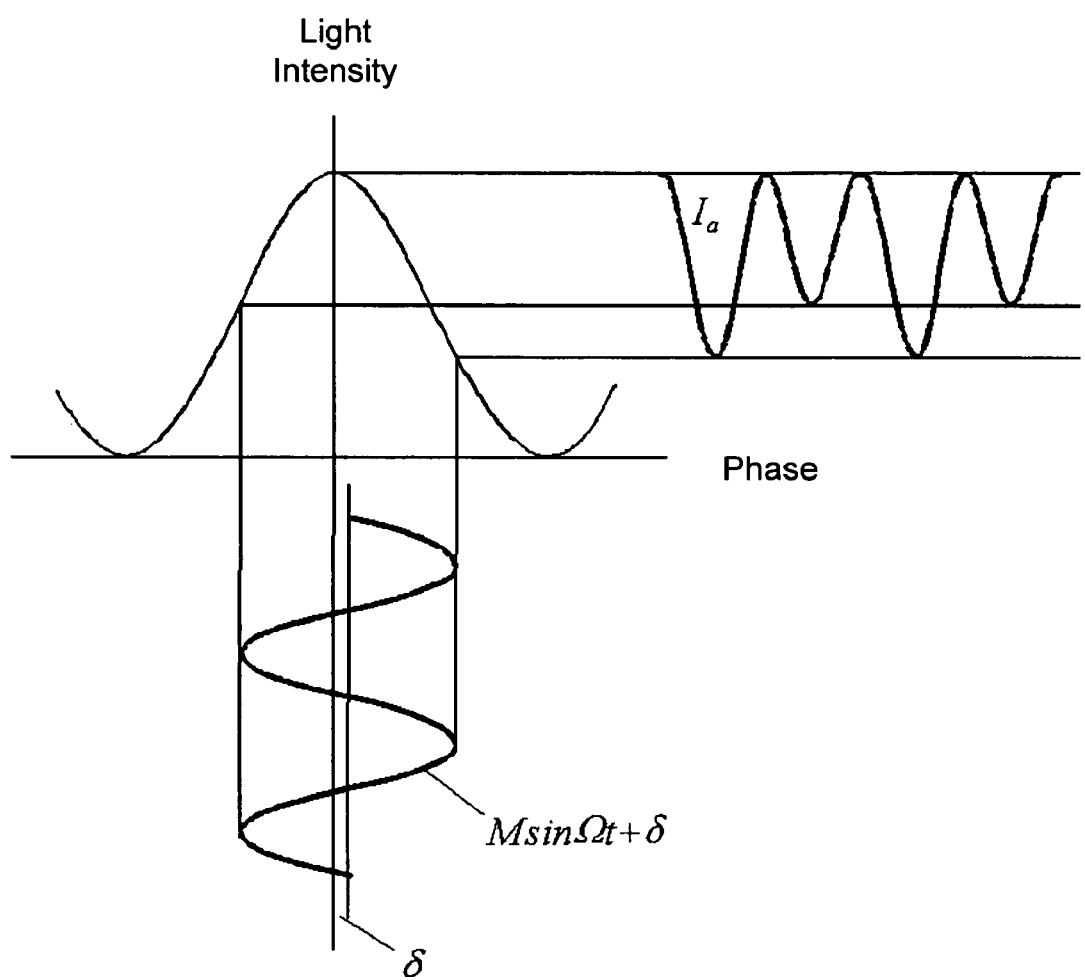
FIG. 6 illustrates the waveform of the intensity received at the detector in the system in FIGS. 5A and 5B as a function of the phase where the detected light intensity exhibits an oscillating waveform that possesses a base frequency and its harmonics.

FIG. 6 illustrates the waveform of the intensity I received at the detector 550 as a function of the phase. The detected light intensity exhibits an oscillating waveform that possesses a base frequency of Ω and its harmonics. The amplitudes of the base frequency and each of the harmonics are related to δ and |r|. The mathematical expressions for the relationships between r and the harmonics can be derived. For instance, the amplitude of the base-frequency oscillation and the second harmonic are found to be:

$$A_\Omega = 0.5|E|^2 J_1(M)|r|\sin\delta; \quad (13a)$$

$$A_{2\Omega} = 0.5|E|^2 J_2(M)|r|\cos\delta, \quad (13b)$$

where $J_1$ and $J_2$ are Bessel functions of the first and second order, respectively. Eq. (13a) and (13b) can be used to solve for |r| and δ, i.e. the complete characterization of r.

The effect of having a broadband light source 201 in the system in FIGS. 5A and 5B is analyzed below. When there is a significant differential group delay between the two propagation modes there must be an associated large phase slippage φ that is wavelength dependent. A substantial wavelength spread in the light source means that the phase slippage also possesses a substantial spread. Such a phase spread cannot be eliminated by a phase control device that does not also eliminate the differential group delay. In this case the detected light intensity is given by the following integral:

$$I = \int \left\{ \frac{1+|r|^2}{4}|E(\lambda)|^2 + \frac{|r|}{2}|E(\lambda)|^2 \cos[M\sin(\Omega t) + \varphi(\lambda) + \delta] \right\} d\lambda. \quad (14)$$

It is easy to see that if the range of φ(λ) is comparable to π for the bandwidth of the light source no oscillation in I can be observed as oscillations for different wavelengths cancel out because of their phase difference. This phenomenon is in close analogy to the interference of white light wherein color fringes are visible only when the path difference is small (the film is thin). The above analysis demonstrates that the use of a broadband light source enables range detection using the proposed apparatus. In order to do so, let the s-wave to have a longer optical path in the system compared to the p-wave (not including its round-trip between Probing Head and Sample). For any given path length difference in the system there is a matching distance between Probing Head and Sample, z, that cancels out the path length difference. If an oscillation in I is observed the p-wave must be reflected from this specific distance z. By varying the path length difference in the system and record the oscillation waveforms we can therefore acquire the reflection coefficient r as a function of the longitudinal distance z, or depth. By moving Probing Head laterally, we can also record the variation of r in the lateral directions.

FIG. 7 further shows one exemplary operation of the described system in FIG. 5B or the system in FIG. 3 for acquiring images of optical inhomogeneity. At step 710, the relative phase delay between the two modes is changed, e.g., increased by an increment, to a fixed value for measuring the sample 205 at a corresponding depth. This may be accomplished in FIG. 5B by using the differential delay device 530 or the bias in the differential delay modulator 250 in FIG. 3. At step 720, a modulation driving signal is sent to the modulator 520 in FIG. 5B or the modulator 250 in FIG. 3 to modulate the relative phase delay between the two modes around the fixed value. At step 730, the intensity waveform received in the detector 550 in FIG. 5B or the intensity waveforms received in the detectors 362,363 in FIG. 3 are measured and stored in the electronic controller 370. Upon completion of the step 730, the electronic controller 370 controls the differential delay device 530 in FIG. 5B or the bias in the differential delay modulator 250 in FIG. 3 to change the relative phase delay between the two modes to a different fixed value for measuring the sample 205 at a different depth. This process iterates as indicated by the processing loop 740 until desired measurements of the sample at different depths at the same location are completed. At this point, electronic controller 370 controls the probe head 320 to laterally move to a new location on the sample 205 and repeat the above measurements again until all desired locations on the sample 205 are completed. This operation is represented by the processing loop 750. The electronic controller 370 processes each measurement to compute the values of δ and |r| from the base oscillation and the harmonics at step 760. Such data processing may be performed after each measurement or after all measurements are completed. At step 770, the computed data is sent to the display module 372.

In the above implementations, light for sensing the sample 205 is not separated into two parts that travel along two different optical paths. Two independent propagation modes of the light are guided essentially in the same waveguide at every location along the optical path except for the extra distance traveled by one mode between the probe head 320 and the sample 205. After redirected by the probe head 320, the two modes are continuously guided in the same waveguide at every location along the optical path to the detection module.

Alternatively, the light from the light source to the probe head may be controlled in a single propagation mode (e.g., a first propagation mode) rather than two different modes. The probe head may be designed to cause a first portion of the first mode to reverse its propagation direction while directing the remaining portion, or a second portion, to reach the sample. The reflection or back scattered light of the second portion from the sample is collected by the probe head and is controlled in the second propagation mode different from the first mode to produce a reflected second portion. Both the reflected first portion in the first propagation mode and the reflected second portion in the second propagation mode are directed by the probe head through a common waveguide into the detection module for processing. In comparison with the implementations that use light in two modes throughout the system, this alternative design further improves the stability of the relative phase delay between the two modes at the detection module and provides additional implementation benefits.

Figure 8A:
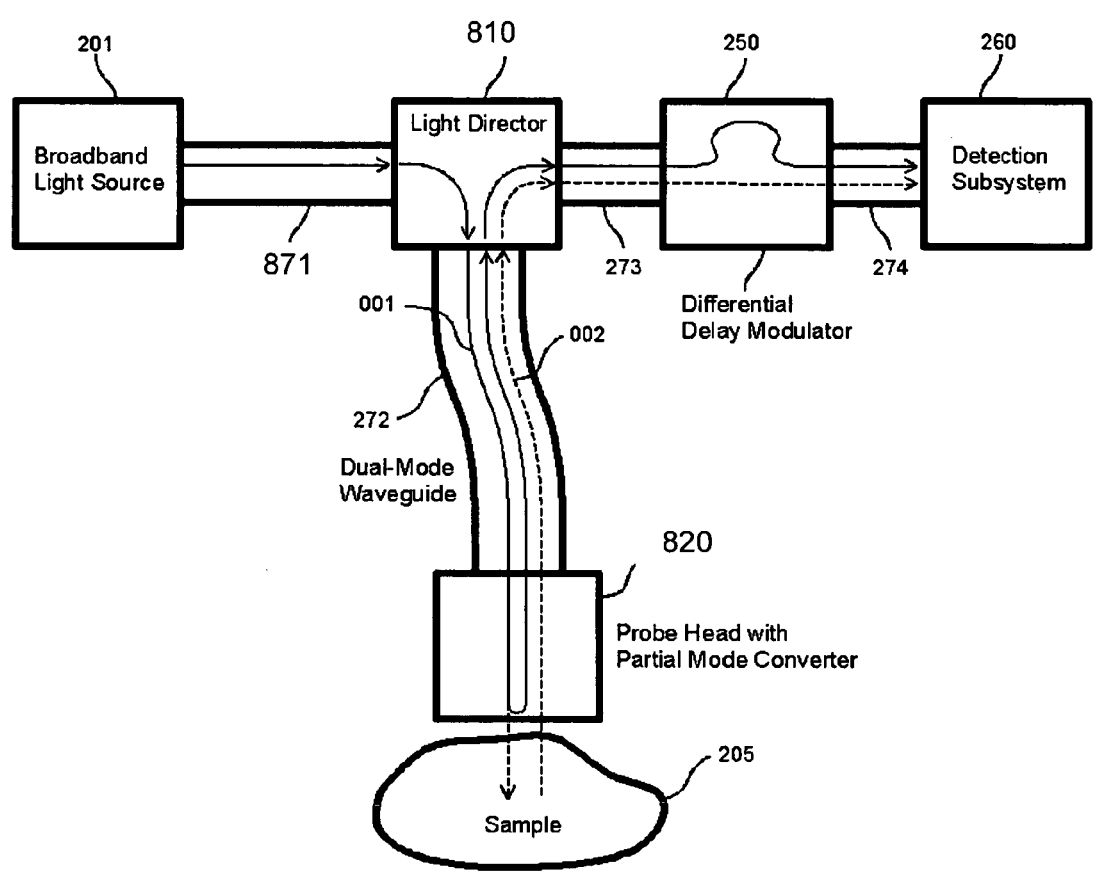
FIGS. 8A and 8B illustrate one exemplary design of the optical layout of the optical sensing system and its system implementation with an electronic controller where light in a single mode is used as the input light.
Figure 8B:
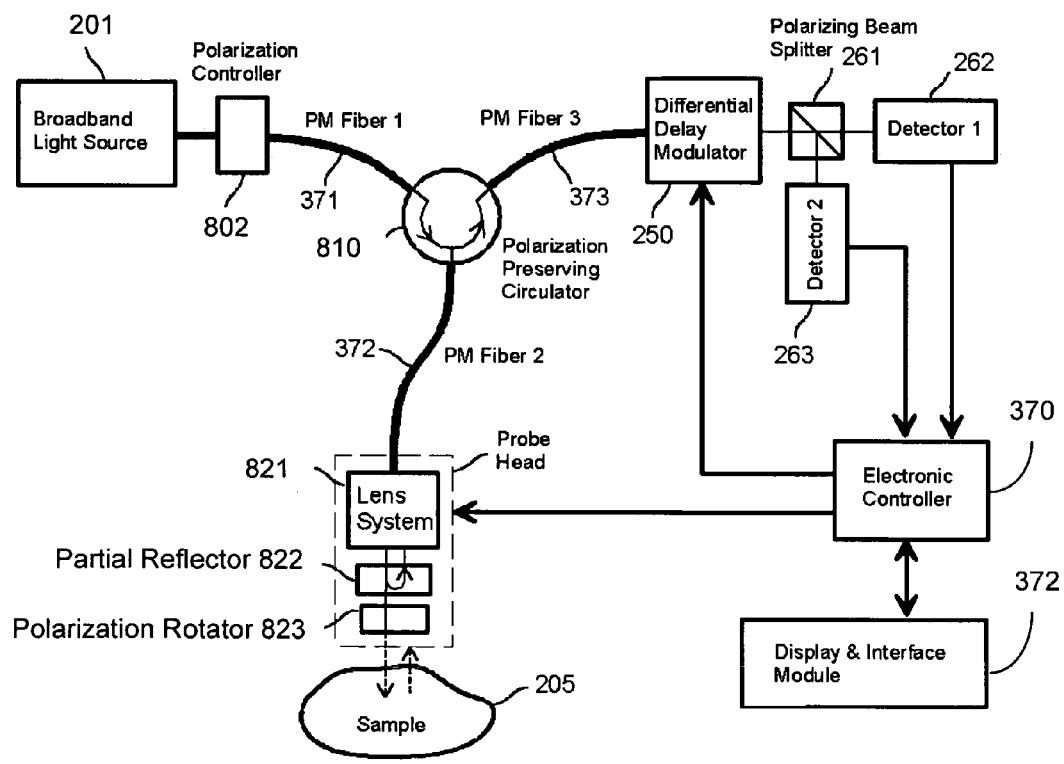

FIGS. 8A and 8B illustrate one exemplary design of the optical layout of the optical sensing system and its system implementation with an electronic controller. An input waveguide 871 is provided to direct light in a first propagation mode, e.g., the mode 001, from the broadband light source 201 to a light director 810. The waveguide 871 may be a mode maintaining waveguide designed to support at least one propagation mode such as the mode 001 or 002. When light is coupled into the waveguide 871 in a particular mode such as the mode 001, the waveguide 871 essentially maintains the light in the mode 001. A polarization maintaining fiber supporting two orthogonal linear polarization modes, for example, may be used as the waveguide 871. Similar to systems shown in FIGS. 2, 3, 5A and 5B, dual-mode waveguides 272 and 273 are used to direct the light. A light director 510 is used to couple the waveguides 871, 272, and 273, to convey the mode 001 from the input waveguide 871 to one of the two modes (e.g., modes 001 and 002) supported by the dual-mode waveguide 272, and to direct light in two modes from the waveguide 272 to the dual-mode waveguide 273. In the example illustrated in FIG. 8A, the light director 810 couples the light in the mode 001 from the waveguide 871 into the same mode 001 in the waveguide 272. Alternatively, the light director 810 may couple the light in the mode 001 from the waveguide 871 into the different mode 002 in the waveguide 272. The dual-mode waveguide 271 is terminated at the other end by a probe head 820 which couples a portion of light to the sample 205 for sensing.

The probe head 820 is designed differently from the prove head 320 in that the probe head 830 converts part of light in the mode 001 into the other different mode 002 when the light is reflected or scattered back from the sample 205. Alternatively, if the light in the waveguide 272 that is coupled from the waveguide 871 is in the mode 002, the probe head 820 converts that part of light in the mode 002 into the other different mode 001 when the light is reflected or scattered back from the sample 205. In the illustrated example, the probe head 820 performs these functions: a) to reverse the propagation direction of a small portion of the incoming radiation in mode 001; b) to reshape the remaining radiation and transmit it to the sample 205; and c) to convert the radiation reflected from the sample 205 to an independent mode 002 supported by the dual-mode waveguide 272. Since the probe head 820 only converts part of the light into the other mode supported by the waveguide 272, the probe head 820 is a partial mode converter in this regard. Due to the operations of the probe head 820, there are two modes propagating away from the probe head 820, the mode 001 that bypasses the sample 205 and the mode 002 for light that originates from sample reflection or back scattering. From this point on, the structure and operations of the rest of the system shown in FIG. 8A may be similar to the systems in FIGS. 2, 3, 5A, and 5B.

FIG. 8B shows an exemplary implementation of the design in FIG. 8A where an electronic controller 2970 is used to control the differential delay modulator 250 and the probe head 820 and a display and interface module 372 is provided. Radiation from broadband light source 201, which may be partially polarized, is further polarized and controlled by an input polarization controller 802 so that only a single polarization mode is excited in polarization-maintaining fiber 371 as the waveguide 871 in FIG. 8A. a polarization preserving circulator may be used to implement the light director 810 for routing light from the waveguide 371 to the waveguide 372 and from the waveguide 372 to the waveguide 373.

The probe head 820 in FIG. 8B may be designed to include a lens system 821 similar to the lens system 321, a partial reflector 822, and a polarization rotator 823. The partial reflector 822 is used to reflect the first portion of light received from the waveguide 372 back to the waveguide 372 without changing its propagation mode and transmits light to and from the sample 205. The polarization rotator 823 is used to control the light from the sample 205 to be in the mode 002 upon entry of the waveguide 372.

Figure 9:
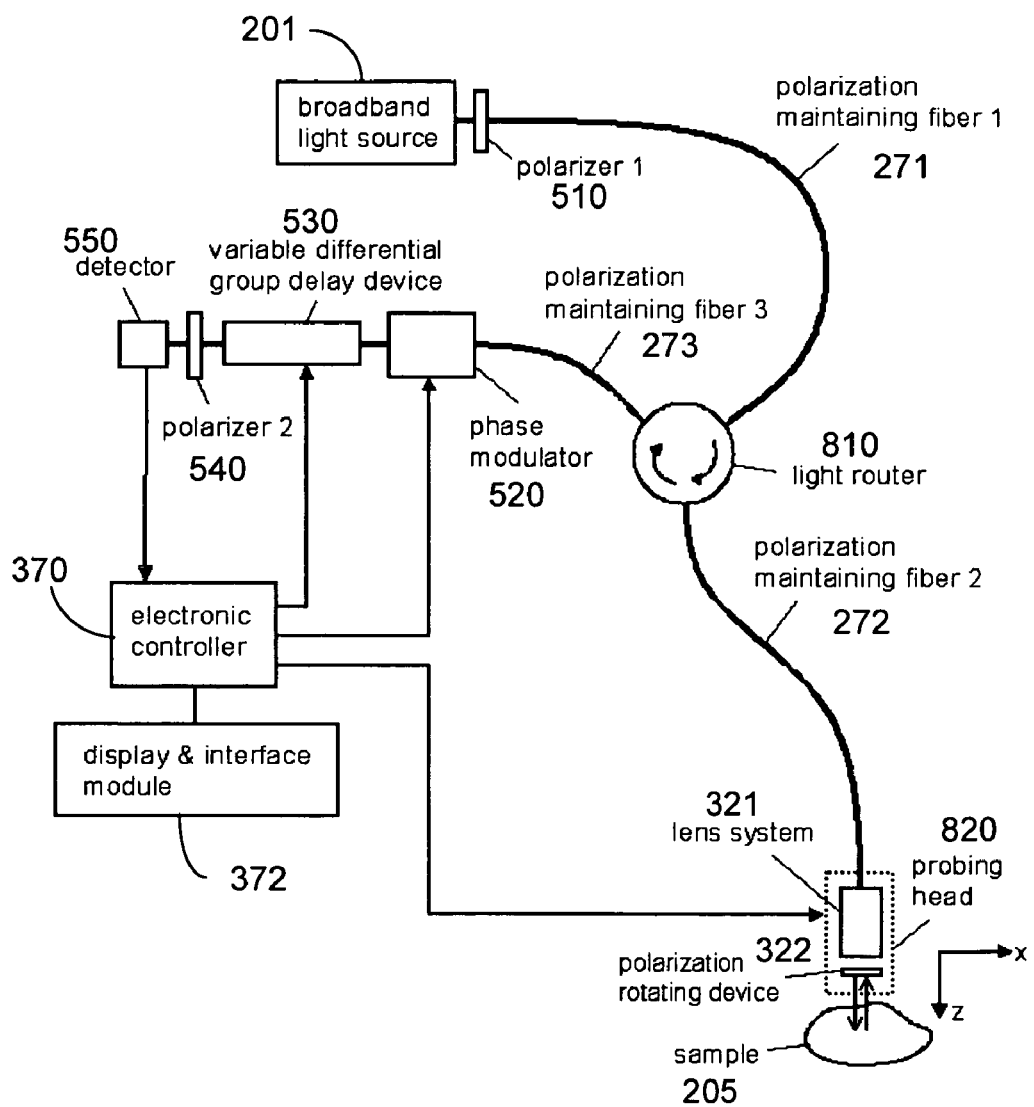
FIG. 9 shows another example of a system implementation where the optical probe head receives light in a single input mode and converts part of light into a different mode.

FIG. 9 shows another example of a system implementation where the optical probe head 820 receives light in a single input mode and converts part of light into a different mode. An input polarizer 510 is used in the input PM fiber 272 to control the input light in the single polarization mode. A phase modulator 520 and a variable differential group delay device 530 are coupled to the output PM fiver 273 to control and modulate the relative phase delay of the two modes before optical detection. An output polarizer 540 is provided to mix the two modes and the detector 550 is used to detect the output from the output polarizer 540.

Figure 10A:
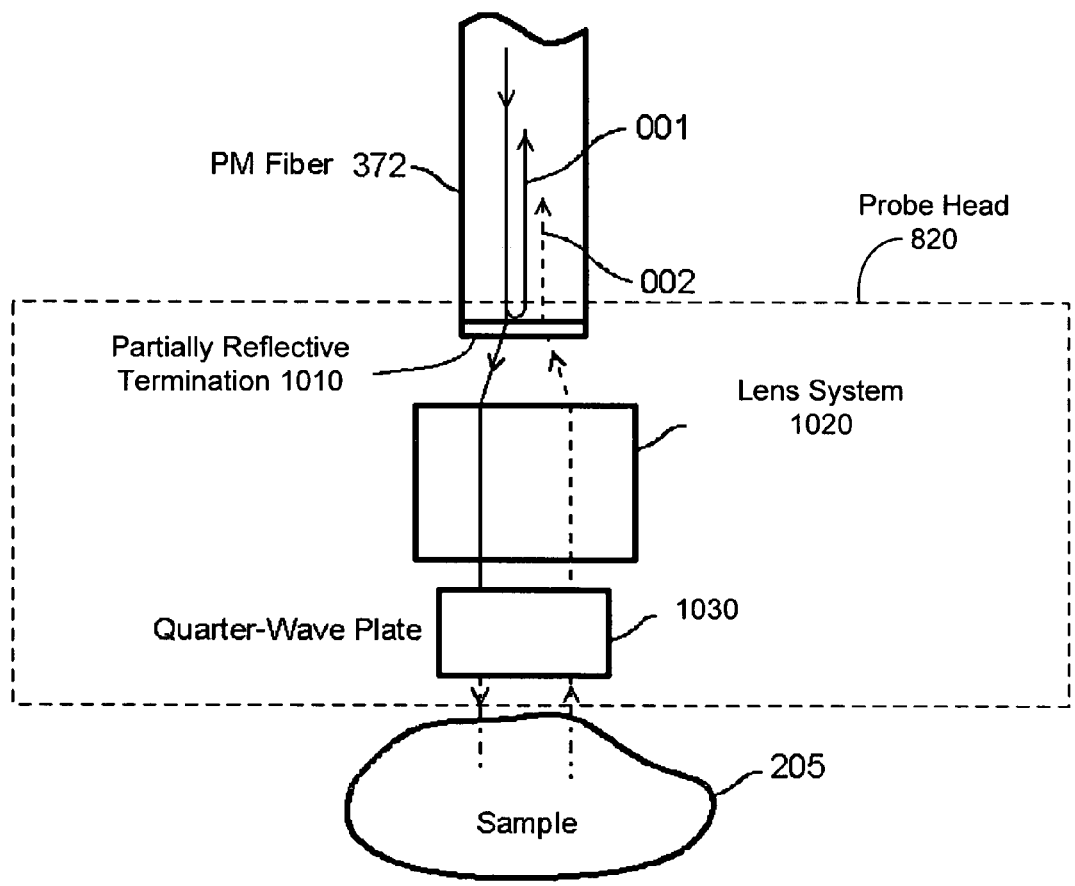
FIGS. 10A and 10B show two examples of the possible designs for the probe head used in sensing systems where the input light is in a single mode.
Figure 10B:
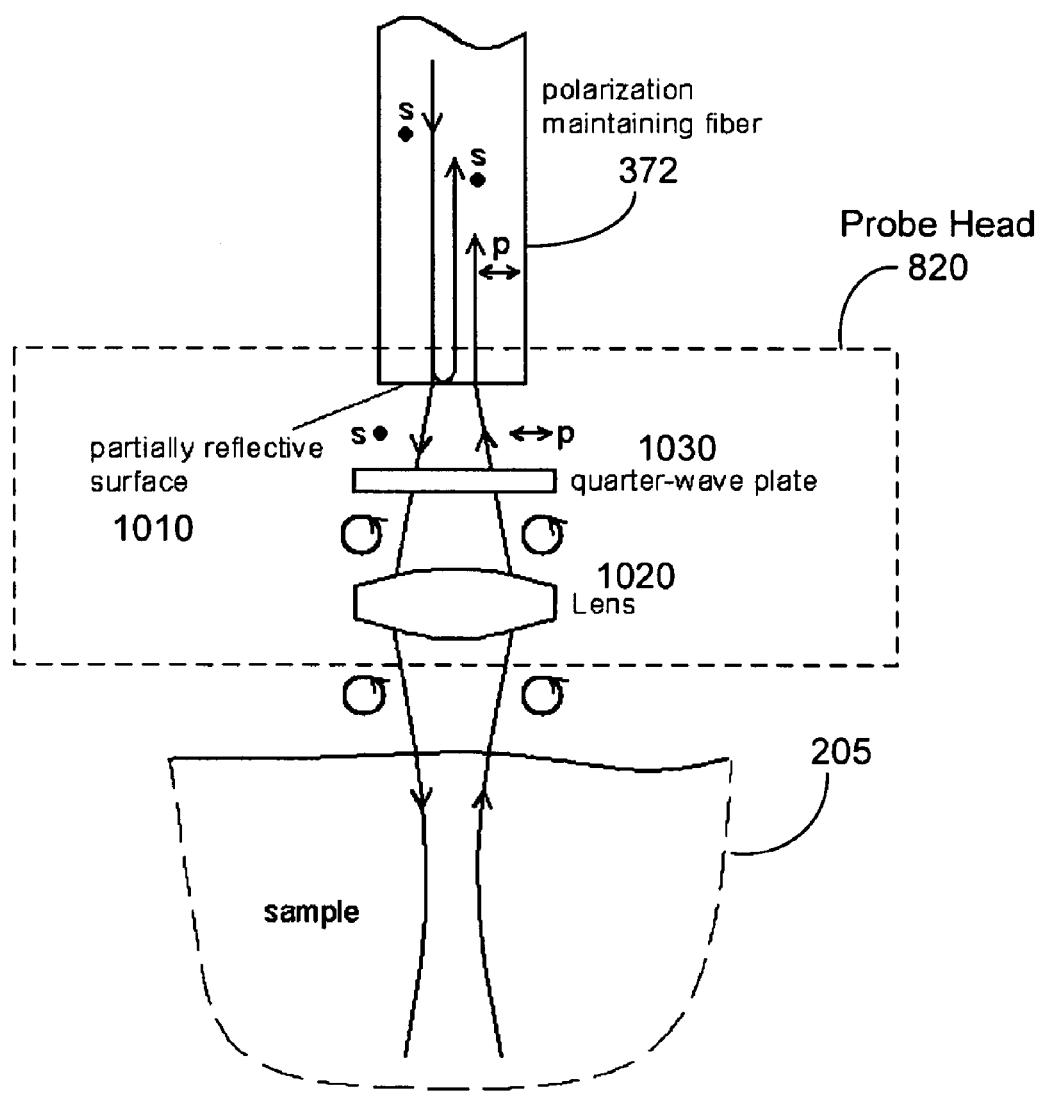

FIGS. 10A and 10B show two examples of the possible designs for the probe head 820 including a partially reflective surface 1010, a lens system 1020, and a quarter-wave plate 1030 for rotating the polarization and to convert the mode. In FIG. 10A, the termination or end facet of polarization-maintaining fiber 372 is used as the partial reflector 1010. An uncoated termination of an optical fiber reflects approximately 4% of the light energy. Coatings can be used to alter the reflectivity of the termination to a desirable value. The lens system 1020 reshapes and delivers the remaining radiation to sample 205. The other role played by the lens system 1020 is to collect the radiation reflected from the sample 205 back into the polarization-maintaining fiber 372. The quarter wave plate 1030 is oriented so that its optical axis make a 45-degree angle with the polarization direction of the transmitted light. Reflected light from the sample 205 propagates through the quarter wave plate 1030 once again to become polarized in a direction perpendicular to mode 001, i.e. mode 002. Alternatively, the quarter wave plate 1030 may be replaced by a Faraday rotator. The head design in FIG. 10B changes the positions of the lens system 1020 and the quarter wave plate or Faraday rotator 1030.

Figure 11:
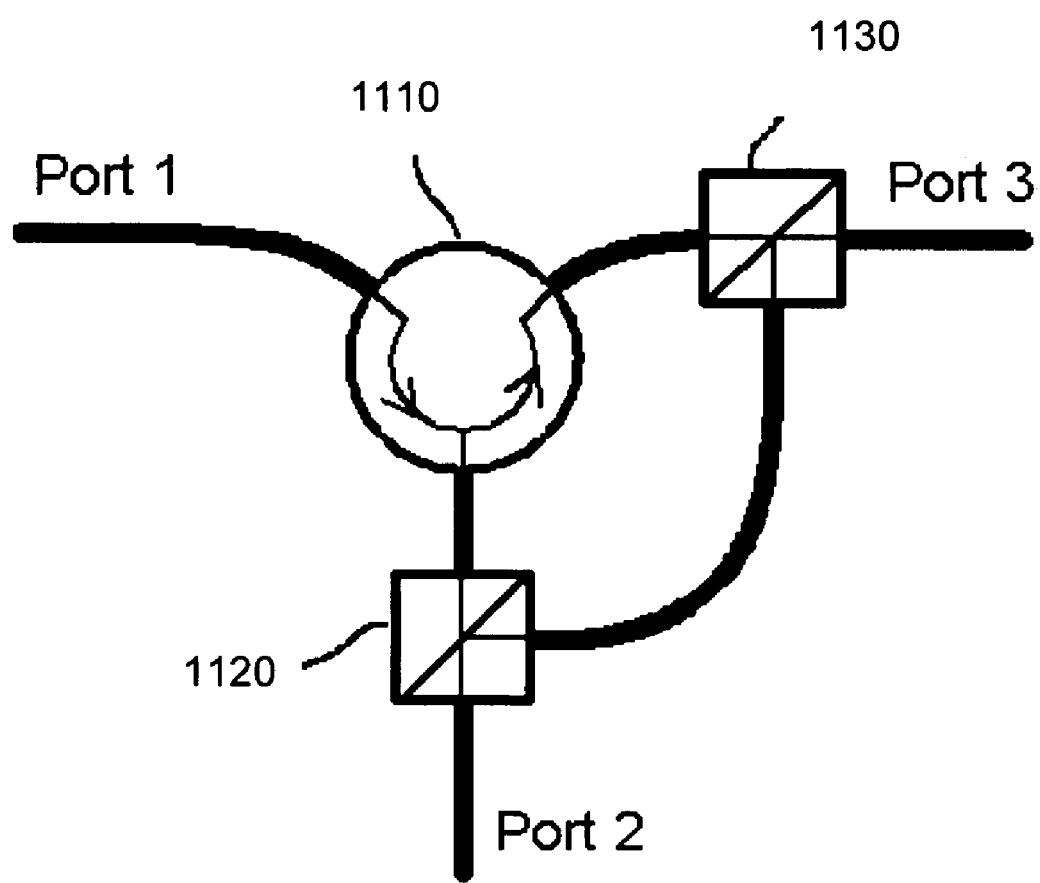
FIG. 11 shows one implementation of a light director that includes a polarization-maintaining optical circulator and two polarization beam splitters.

In the examples in FIGS. 8A, 8B, and 9, there is only one polarization mode entering the light director 810 or the polarization-preserving circulator from waveguide 871 or 371. Therefore, the light director 810 or the polarization preserving circulator may be constructed with a polarization-maintaining optical circulator 1110 and two polarization beam splitters 1120 and 1130 as shown in FIG. 11. The polarization-maintaining circulator 1110 is used to convey only one polarization mode among its three ports, rather than both modes as in the case shown in FIGS. 3, 5A and 5B. The polarizing beam splitter 1120 and 1130 are coupled to polarization-maintaining circulator 1110 so that both polarization modes entering Port 2 are conveyed to Port 3 and remain independent.

Figure 12:
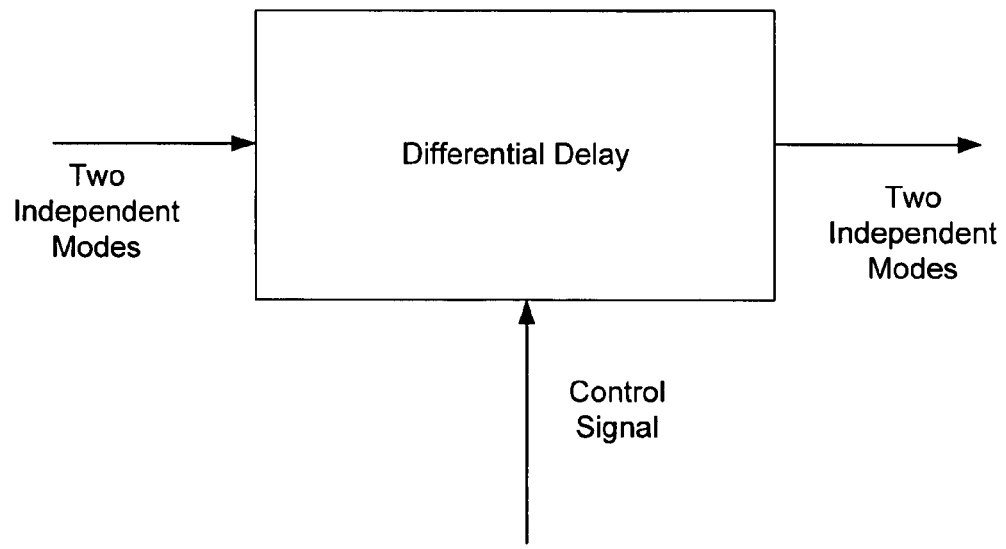
FIG. 12 illustrates an example of the optical differential delay modulator used in present optical sensing systems where an external control signal is applied to control a differential delay element to change and modulate the relative delay in the output.

A number of hardware choices are available for differential delay modulator 250. FIG. 12 illustrates the general design of the modulator 250 where an external control signal is applied to control a differential delay element to change and modulate the relative delay in the output. Either mechanical or non-mechanical elements may be used to produce the desired relative delay between the two modes and the modulation on the delay.

Figure 12A:
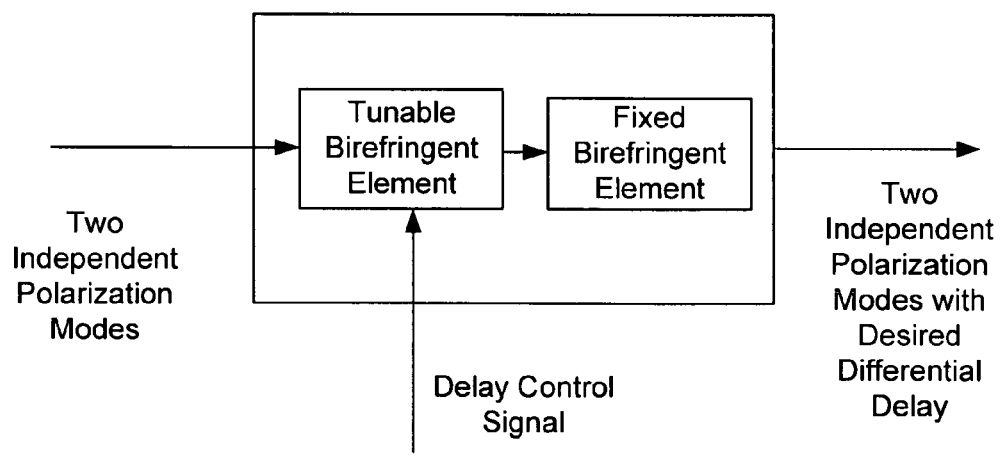
FIGS. 12A and 12B illustrate two exemplary devices for implementing the optical differential delay modulator in FIG. 12.

In one implementation, a non-mechanical design may include one or more segments of tunable birefringent materials such as liquid crystal materials or electro-optic birefringent materials such as lithium niobate crystals in conjunction with one or more fixed birefringent materials such as quartz and rutile. The fixed birefringent material provides a fixed delay between two modes and the tunable birefringent material provides the tuning and modulation functions in the relative delay between the two modes. FIG. 12A illustrates an example of this non-mechanical design where the two modes are not physically separated and are directed through the same optical path with birefringent segments which alter the relative delay between two polarization modes.

Figure 12B:
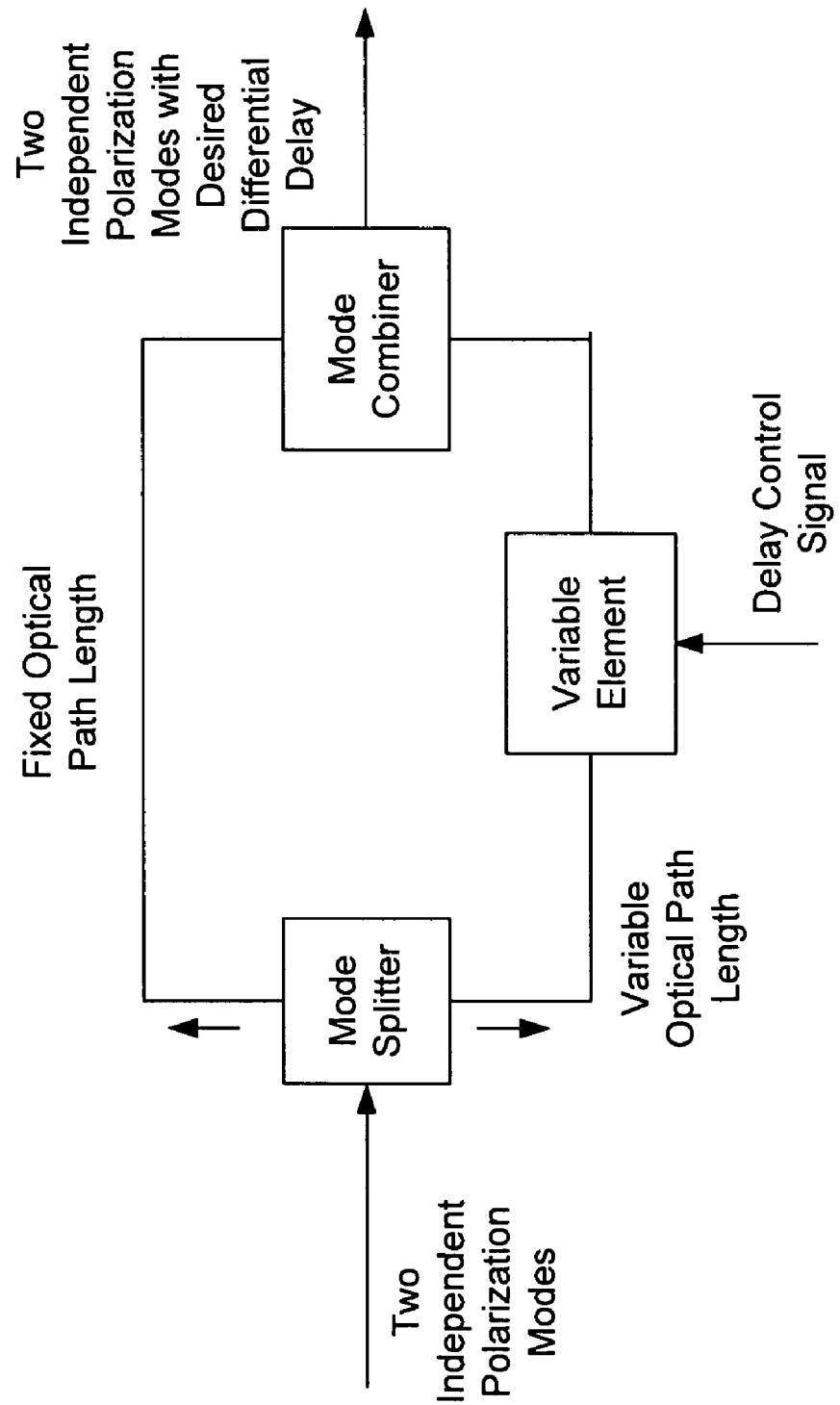

FIG. 12B shows a different design where the two modes in the received light are separated by a mode splitter into two different optical paths. A variable delay element is inserted in one optical path to adjust and modulate the relative delay in response to an external control signal. A mode combiner is then used to combine the two modes together in the output. The mode splitter and the mode combiner may be polarization beams splitters when two orthogonal linear polarizations are used as the two modes.

The variable delay element in one of the two optical paths may be implemented in various configurations. For example, the variable delay element may be a mechanical element. A mechanical implementation of the device in FIG. 12B may be constructed by first separating the radiation by polarization modes with a polarizing beam splitter, one polarization mode propagating through a fixed optical path while the other propagating through a variable optical path having a piezoelectric stretcher of polarization maintaining fibers, or a pair of collimators both facing a mechanically movable retroreflector in such a way that the light from one collimator is collected by the other through a trip to and from the retroreflector, or a pair collimators optically linked through double passing a rotatable optical plate and bouncing off a reflector.

Figure 13A:
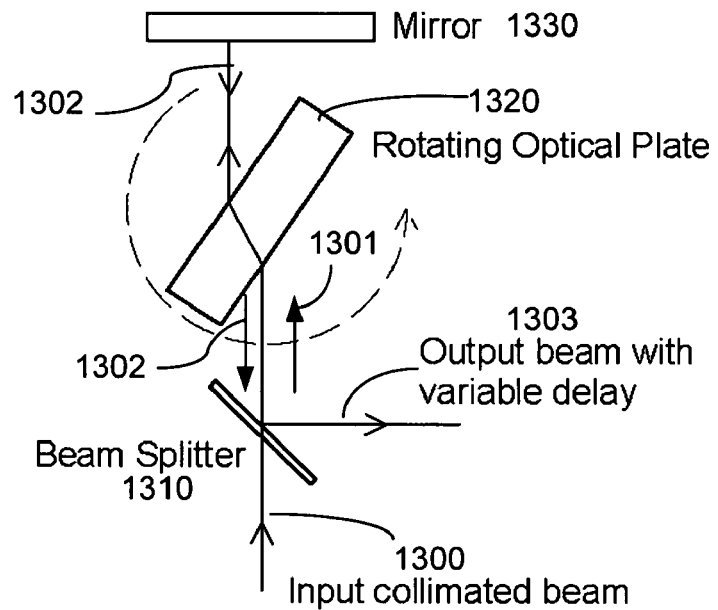
FIGS. 13A and 13B illustrate two examples of a mechanical variable delay element suitable for implementing the optical differential delay modulator shown in FIG. 12B.
Figure 13B:
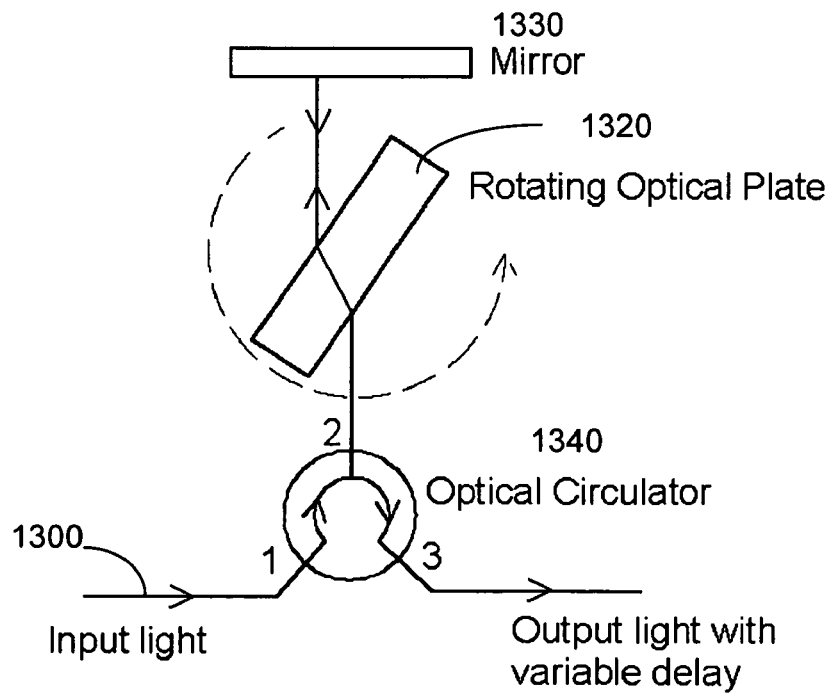

FIGS. 13A and 13B illustrate two examples of a mechanical variable delay element suitable for FIG. 12B. Such a mechanical variable delay device may be used to change the optical path length of a light beam at high speeds and may have various applications other than what is illustrated in FIG. 12B. In addition, the optical systems in this application may use such a delay device.

The mechanical delay device shown in FIG. 13A includes an optical beam splitter 1310, a rotating optical plate 1320 which may be a transparent plate, and a mirror or reflector 1330. The beam splitter 1310 is used as the input port and the output port for the device. The rotating optical plate 1320 is placed between the mirror 1330 and the beam splitter 1310. The input light beam 1300 is received by the beam splitter 1310 along the optical path directing from the beam splitter 1310 to the mirror 1330 through the rotating optical plate 1320. A portion of the light 1300 transmitting through the beam splitter 1310 is the beam 1301 which impinges on and transmits through the rotating optical plate 1320. The mirror or other optical reflector 1330 is oriented to be perpendicular to the light beam incident to the optical plate 1310 from the opposite side. The reflected light beam 1302 from the mirror 1320 traces the same optical path back traveling until it encounters the Beam Splitter 1310. The Beam Splitter 1310 deflects part of the back traveling light 1302 to a different direction as the output beam 1303.

In this device, the variation of the optical path length is caused by the rotation of the Optical Plate 1320. The Optical Plate 1320 may be made of a good quality optical material. The two optical surfaces may be flat and well polished to minimize distortion to the light beam. In addition, the two surfaces should be parallel to each other so that the light propagation directions on both sides of the Optical Plate 1320 are parallel. The thickness of the Optical Plate 1320 may be chosen according to the desirable delay variation and the range of the rotation angle. The optical path length experienced by the light beam is determined by the rotation angle of the Optical Plate 1320. When the surfaces of the Optical Plate 1320 is perpendicular to the light beam (incident angle is zero), the path length is at its minimum. The path length increases as the incident angle increases.

In FIG. 13A, it may be beneficial to collimate the input light beam so that it can travel the entire optical path without significant divergence. The Optical Plate 1320 may be mounted on a motor for periodic variation of the optical delay. A good quality mirror with a flat reflecting surface should be used to implement the mirror 1330. The reflecting surface of the mirror 1330 may be maintained to be perpendicular to the light beam.

If a linearly polarized light is used as the input beam 1300 in FIG. 13A, it is beneficial to have the polarization direction of the light parallel to the incident plane (in the plane of the paper) as less reflection occurs at the surfaces of Optical Plate 1320 for this polarization compared to other polarization directions. Antireflection coatings can be used to further reduce the light reflection on the surfaces of the Optical Plate 1320.

The beam splitter 1310 used in FIG. 13A uses both its optical transmission and optical reflection to direct light. This aspect of the beam splitter 1310 causes reflection loss in the output of the device due to the reflection loss when the input light 1300 first enters the device through transmission of the beam splitter 1310 and the transmission loss when the light exits the device through reflection of the beam splitter 1310. For example, a maximum of 25% of the total input light may be left in the output light if the beam splitter is a 50/50 beam splitter. To avoid such optical loss, an optical circulator may be used in place of the beam splitter 1320. FIG. 13B illustrates an example where the optical circulator 1340 with 3 ports is used to direct input light to the optical plate 1320 and the mirror 1330 and directs returned light to the output port. The optical circulator 1340 may be designed to direct nearly all light entering its port 1 to port 2 and nearly all light entering its port 2 to the port 3 with nominal optical loss and hence significantly reduces the optical loss in the device. Commercially available optical circulators, either free-space or fiber-based, may be used to implement the circulator 1340.

Figure 14A:
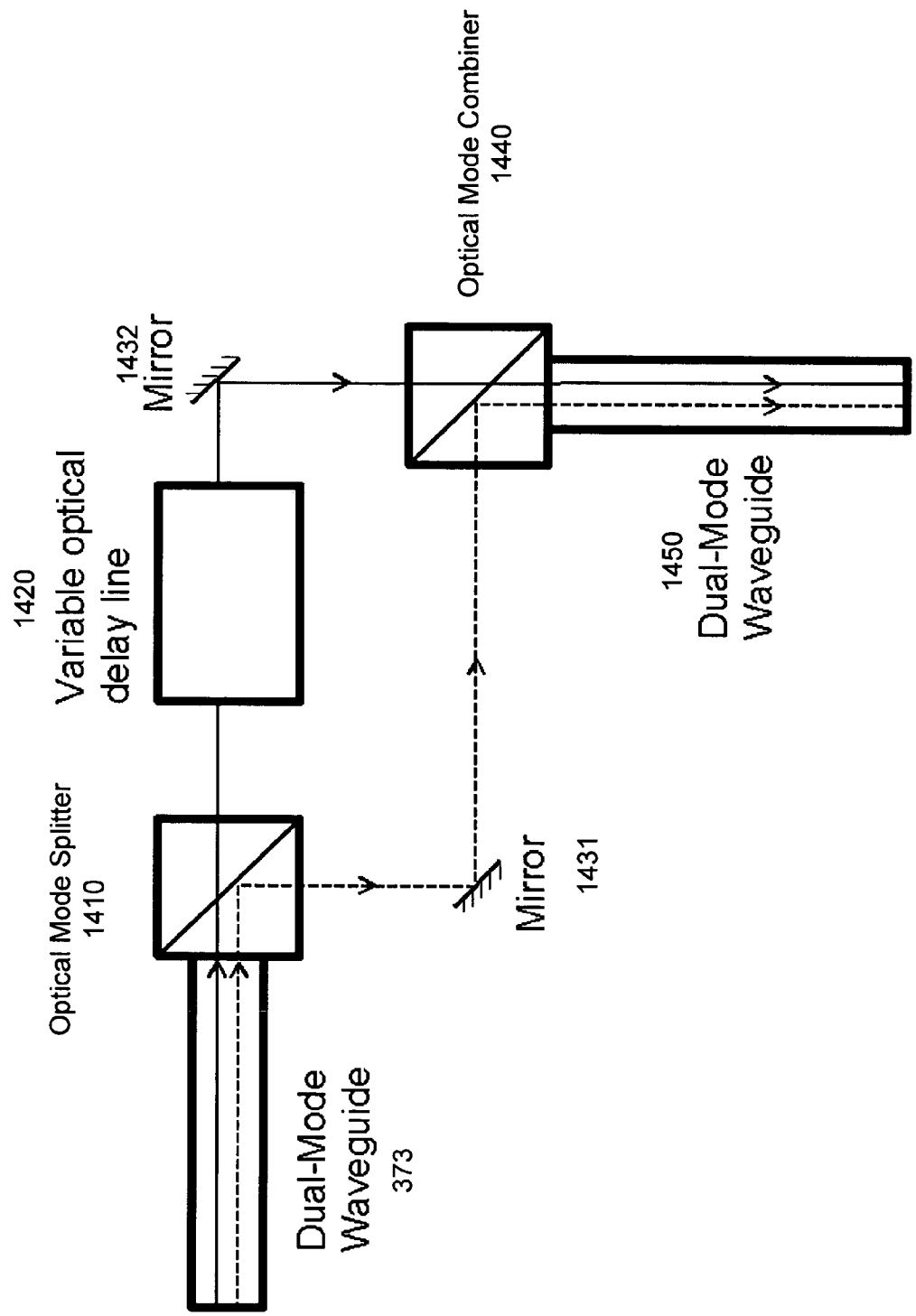
FIG. 14A shows an exemplary implementation of the delay device in FIG. 12B as part of or the entire differential delay modulator.
Figure 14B:
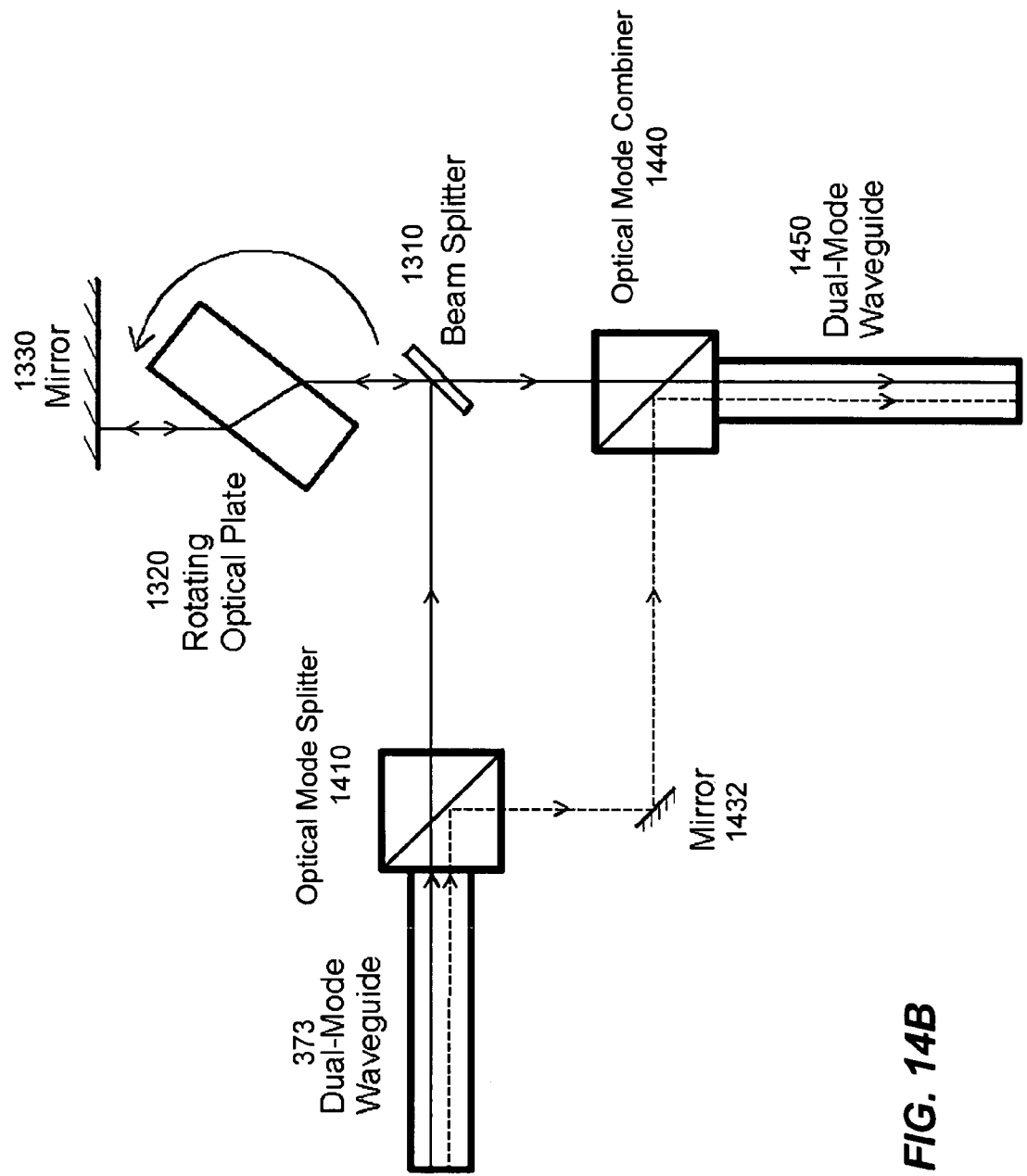
FIG. 14B shows a delay device based on the design in FIG. 14A where the mirror and the variable optical delay line are implemented by the mechanical delay device in FIG. 13A.

FIG. 14A shows an exemplary implementation of the delay device in FIG. 12B as part of or the entire differential delay modulator 250. A first optical mode splitter 1410 is used to separate two modes in the waveguide 373 into two paths having two mirrors 1431 and 1432, respectively. A second optical mode splitter 1440, which is operated as a mode combiner, is used to combine the two modes into an output. If the two modes are two orthogonal linear polarizations, for example, polarization beam splitters may be used to implement the 1410 and 1440. A variable optical delay line or device 1420 is placed in the upper path to control the differential delay between the two paths. The output may be coupled into another dual-mode waveguide 1450 leading to the detection module or directly sent into the detection module. FIG. 14B shows a delay device based on the design in FIG. 14A where the mirror 1432 and the variable optical delay line 1420 are implemented by the mechanical delay device in FIG. 13A. The mechanical delay device in FIG. 13B may also be used to implement the device in FIG. 14A.

In the above examples, a single dual-mode waveguide 272 or 372 is used as an input and output waveguide for the probe head 220, 320, or 820. Hence, the input light, either in a single mode or two independent modes, is directed into the probe head through that dual-mode waveguide 272 or 372, and the output light in the two independent modes is also directed from the probe head to the detection subsystem or detector.

Alternatively, the single dual-mode waveguide 272 or 372 may be replaced by two separate waveguides, one to direct input light from the light source to the probe head and another to direct light from the probe head to the detection subsystem or detector. As an example, the device in FIG. 2 may have a second waveguide different from the waveguide 272 to direct reflected light in two different modes from the optical probe head 220 to the modulator 250 and the detection subsystem 260. In this design, the light director 210 may be eliminated. This may be an advantage. In implementation, the optics within the probe head may be designed to direct the reflected light in two modes to the second waveguide.

Figure 15:
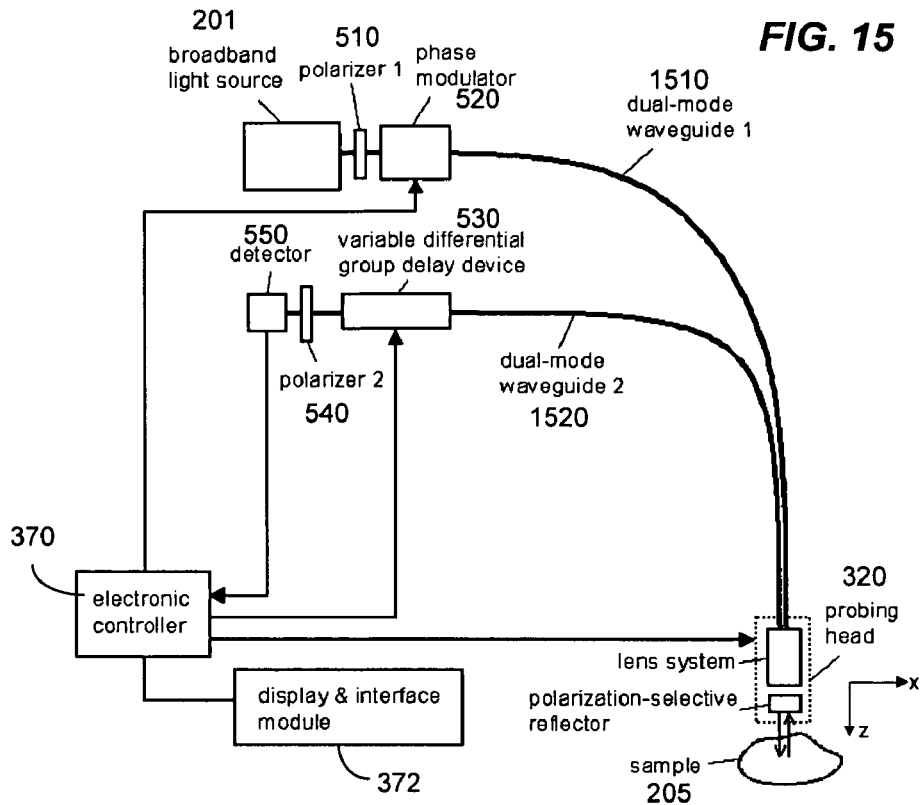
FIG. 15 illustrates an optical sensing system as an alternative to the device shown in FIG. 5B.

FIG. 15 illustrates an example for this design as an alternative to the device shown in FIG. 5B. In this design, the probing light is delivered to the sample 205 through one dual-mode waveguide 1510 and the reflected/scattered light is collected by the probe head 320 and is directed through another dual-mode waveguide 1520. With the probe head shown in FIG. 4, the mirror 424 may be oriented and aligned so that the light is reflected into the waveguide 1520 instead of the waveguide 1510. This design may be applied to other devices based on the disclosure of this application, including the exemplary devices in FIGS. 2, 3, 8A, 8B and 9.

The above-described devices and techniques may be used to obtain optical measurements of a given location of the sample at different depths by controlling the relative phase delay between two modes at different values and optical measurements of different locations of the sample to get a tomographic map of the sample at a given depth or various depths by laterally changing the relative position of the probe head over the sample. Such devices and techniques may be further used to perform other measurements on a sample, including spectral selective measurements on a layer of a sample.

In various applications, it may be beneficial to obtain information about certain substances, identifiable through their spectral absorbance, dispersed in the samples. For this purpose, a tunable bandpass filter may be used to either filter the light incident to the probe head to select a desired spectral window within the broadband spectrum of the incident light to measure the response of the sample and to vary the center wavelength of the spectral window to measure a spectral distribution of the responses of the sample. This tuning of the bandpass filter allows a variable portion of the source spectrum to pass while measuring the distribution of the complex reflection coefficient of the sample.

Alternatively, the broadband light may be sent to the optical probe head without optical filtering and the spectral components at different wavelengths in the output light from the probe head may be selected and measured to measure the response of the sample around a selected wavelength or the spectral distribution of the responses of the sample. In one implementation, a tunable optical bandpass filter may be inserted in the optical path of the output light from the probe head to filter the light. In another implementation, a grating or other diffractive optical element may be used to optically separate different spectral components in the output light to be measured by the detection subsystem or the detector.

Figure 16:
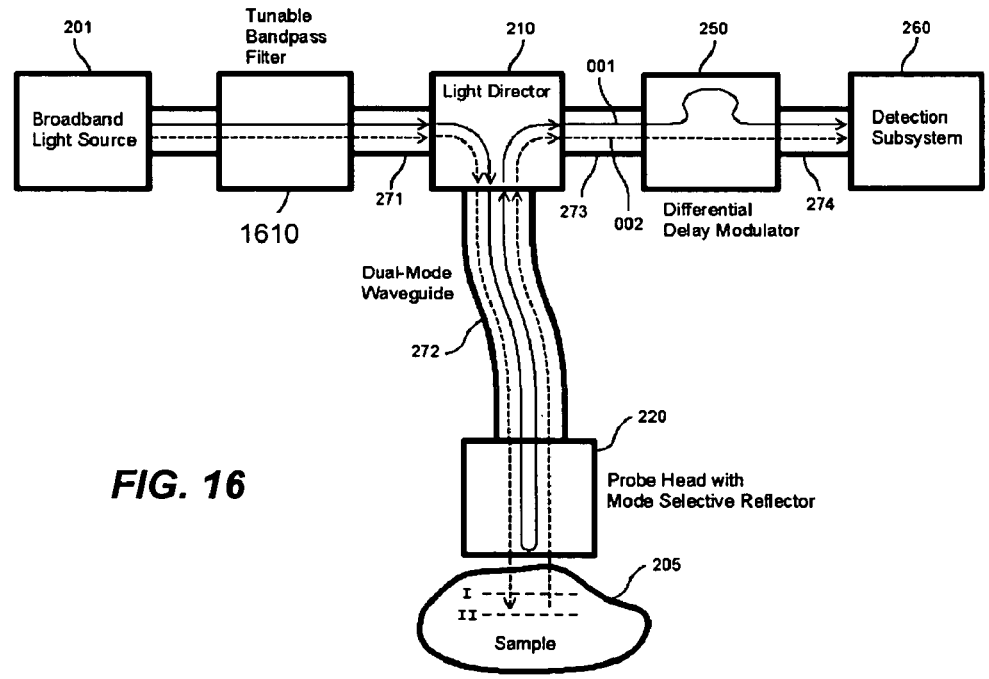
FIG. 16 shows a system based on the design in FIG. 2 where a tunable filter is inserted in the input waveguide to filter the input light in two different modes.
Figure 17:
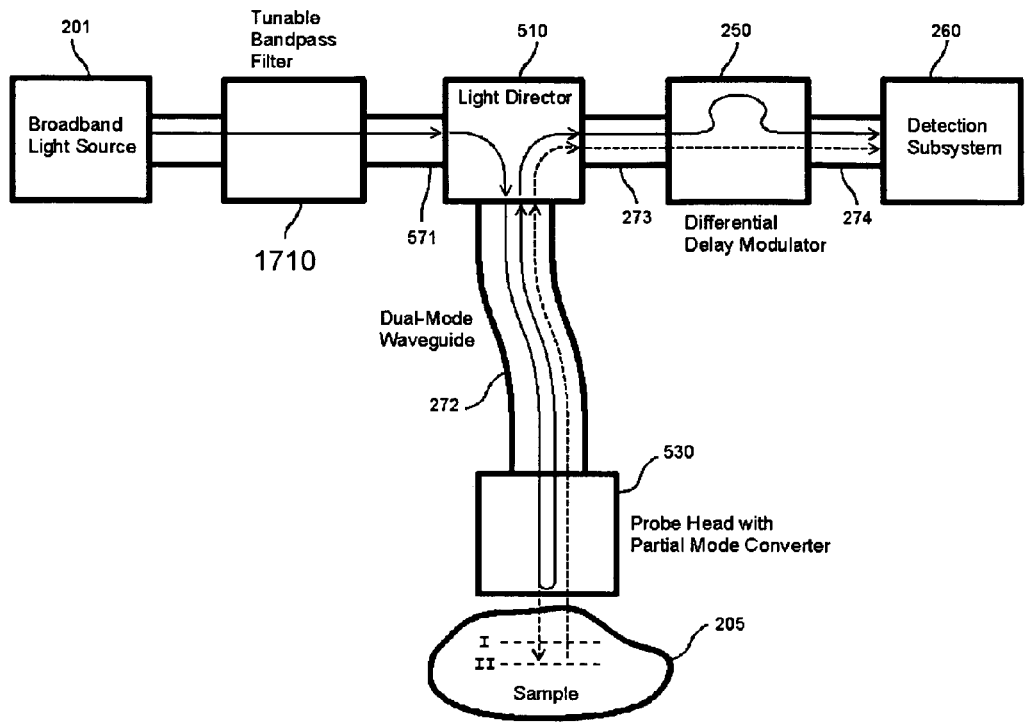
FIG. 17 shows another exemplary system based on the design in FIG. 8A where a tunable filter is inserted in the input waveguide to filter the input light in a single mode.

As an example, FIG. 16 shows a system based on the design in FIG. 2 where a tunable filter 1610 is inserted in the input waveguide 271 to filter the input light in two different modes. FIG. 17 shows another exemplary system based on the design in FIG. 8A where a tunable filter 1710 is inserted in the input waveguide 871 to filter the input light in a single mode. Such a tunable filter may be placed in other locations.

Figure 18:
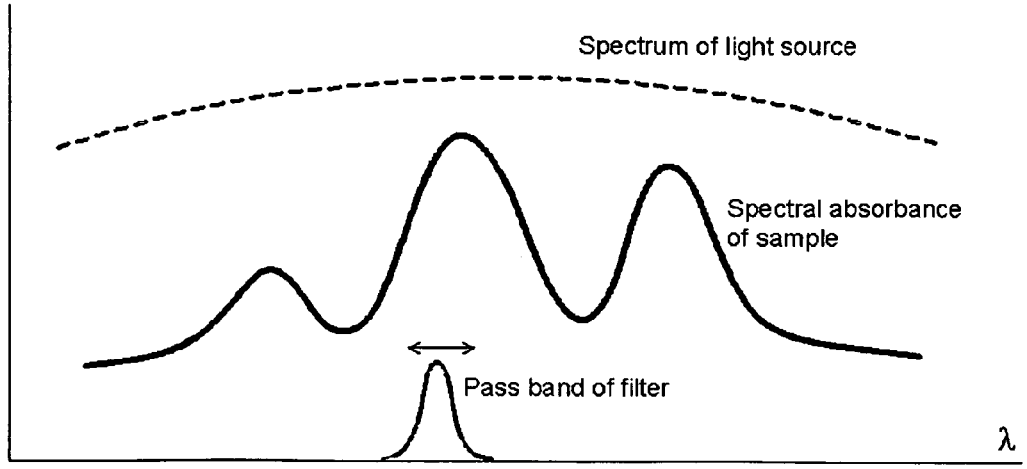
FIG. 18 illustrates the operation of the tunable bandpass filter in the devices in FIGS. 16 and 17.

FIG. 18 illustrates the operation of the tunable bandpass filter in the devices in FIGS. 16 and 17. The filter selects a narrow spectral band within the spectrum of the light source to measure the spectral feature of the sample.

Notably, the devices and techniques of this application may be used to select a layer within a sample to measure by properly processing the measured data. Referring back to the devices in FIGS. 16 and 17, let us assume that the absorption characteristics of a layer bounded by interfaces I and II is to be measured. For the simplicity of description, it is assumed that the spectral absorption of the substance in the layer is characterized by a wavelength-dependent attenuation coefficient $\mu_h(\lambda)$ and that of other volume is characterized by $\mu_g(\lambda)$. It is further assumed that the substance in the vicinity of interface I (II) possesses an effective and wavelength independent reflection coefficient $r_I$ ($r_{II}$). If the characteristic absorption of interest is covered by the spectrum of the light source, an optical filter 1610 or 1710 with a bass band tunable across the characteristic absorption of the sample 205 may be used to measure the spectral responses of the sample 205 centered at different wavelengths.

In operation, the following steps may be performed. First, the differential delay modulator 250 is adjusted so that the path length traveled by one mode (e.g., the mode 001) matches that of radiation reflected from interface I in the other mode (e.g., the mode 002). At this point, the pass band of filter 1610 or 1710 may be scanned while recording the oscillation of the measured signal due to a periodic differential phase generated by the modulator 250. The oscillation amplitude as a function of wavelength is given by $$A_I(\lambda) = r_I e^{-2\mu_g(\lambda) z_I} \tag{15}$$

where $z_I$ is the distance of interface I measured from the top surface of the sample 205. Next, the differential delay modulator 250 is adjusted again to change the differential delay so that the path length traveled by the mode 001 matches that of radiation reflected from interface II in the mode 002. The measurement for the interface II is obtained as follows:

$$A_{II}(\lambda) = r_{II} e^{-\mu_g(\lambda) z_I - 2\mu_h(\lambda) z_{II}}, \tag{16}$$

where $z_{II}$ is the distance of interface II measured from interface I. To acquire the absorption characteristics of the layer bounded by the interfaces I and II, Eq. (7) and Eq. (6) can be used to obtain the following ratio:

$$\frac{A_{II}(\lambda)}{A_I(\lambda)} = \frac{r_{II}}{r_I} e^{-2\mu_h(\lambda) z_{II}}. \tag{17}$$

Notably, this equation provides the information on the absorption characteristics of the layer of interest only and this allows measurement on the layer. This method thus provides a "coherence gating" mechanism to optically acquire the absorbance spectrum of a particular and designated layer beneath a sample surface.

It should be noted that the pass band of the optical filter 1610 or 1710 may be designed to be sufficiently narrow to resolve the absorption characteristics of interest and at the meantime broad enough to differentiate the layer of interest. The following example for monitoring the glucose level by optically probing a patient's skin shows that this arrangement is reasonable and practical.

Various dependable glucose monitors rely on taking blood samples from diabetes patients. Repeated pricking of skin can cause considerable discomfort to patients. It is therefore desirable to monitor the glucose level in a noninvasive manner. It is well known that glucose in blood possesses "signature" optical absorption peaks in a near-infrared (NIR) wavelength range. It is also appreciated the main obstacle in noninvasive monitoring of glucose is due to the fact that a probing light beam interacts, in its path, with various types of tissues and substances which possess overlapping absorption bands. Extracting the signature glucose peaks amongst all other peaks has proven difficult.

The above "coherence gating" may be used to overcome the difficulty in other methods for monitoring glucose. For glucose monitoring, the designated layer may be the dermis layer where glucose is concentrated in a network of blood vessels and interstitial fluid.

FIG. 19A illustrates an example of a human skin tissue where the coherence gating technique described here can be used to measure the glucose concentration in the dermis layer between the epidermis and the subcutaneous layers. The dermis layer may be optically selected and measured with the coherence gating technique. It is known that the superficial epidermis layer, owing to its pigment content, is the dominant source of NIR absorption. Because of the absence of blood, however, the epidermis yields no useful information for glucose monitoring. The coherent gating technique can be applied to acquire solely the absorbance spectrum of the dermis layer by rejecting the absorptions of the epidermis and the subcutaneous tissues. An additional advantage of this technique is from the fact that dermis exhibits less temperature variation compared to the epidermis. It is known that surface temperature variation causes shifts of water absorption, hampering glucose monitoring.

FIG. 19B shows some predominant glucose absorption peaks in blood in a wavelength range between 1 and 2.5 microns. The width of these peaks are approximately 150 nm. To resolve the peaks, the bandwidth of the tunable bandpass filter may be chosen to be around 30 nm. The depth resolution is determined by the following equation:

$$\frac{2\ln(2)}{\pi} \frac{\lambda_o^2}{\Delta\lambda} = 60 \ \mu m \tag{18}$$

Therefore, the coherence gating implemented with the devices in FIGS. 16 and 17 or other optical sensing devices may be used to determine the absorption characteristics of the glucose in tissue layers no less than 60 µm thick. As illustrated in FIG. 19A, human skin consists of a superficial epidermis layer that is typically 0.1 mm thick. Underneath epidermis is the dermis, approximately 1 mm thick, where glucose concentrates in blood and interstitial fluids. The above analysis indicates that it is possible to use the apparatus shown in FIGS. 16 and 17 to isolate the absorption characteristics of the dermis from that of the epidermis and other layers.

It is clear from Eq. (18) that the product of spectral resolution and layer resolution is a constant for a given center wavelength $\lambda_0$. The choice of the filter bandwidth should be made based on the tradeoff between these two resolutions against the specific requirements of the measurement.

The tunable bandpass filter 1610 or 1710 may be operated to acquire the absorption characteristics of an isolated volume inside a sample.

FIG. 20 illustrates one exemplary implementation of the detection subsystem 260 in FIG. 3 where two diffraction gratings 2010 and 2020 are used to separate different spectral components in the output light beams from the polarizing beam splitter 361. A lens 2012 is positioned to collect the diffracted components from the grating 2010 and focus different spectral components to different locations on its focal plane. A detector array 2014 with multiple photodetector elements is placed at the focal plane of the lens 2012 so that different spectral components are received by different photodetector elements. A second lens 2022 and a detector array 2024 are used in the optical path of the diffracted components in a similar way. In devices shown in FIGS. 5A, 5B, 8A, and 8B where a single optical detector is used for measurements, a single grating, a lens, and a detector array may be used.

In operation, each detector element receives light in a small wavelength interval. The photocurrents from all elements in an array can be summed to form a signal which is equivalent to the signal received in each single detector without the grating shown in FIG. 3. By selectively measuring the photocurrent from an individual element or a group of elements in an array, the spectral information of the sample can be obtained.

In the above described examples, the optical probe head sends out light in two different propagation modes where light in one of the two modes carries the information from the sample. Alternatively, light in a single propagation mode may be used as the input light to the optical probe head and as output light from the optical probe head. Hence, devices based on this design not only use a common optical path to direct light to and from the probe head and sample but also control the light in a single mode. In comparison with above examples where two different modes are used for light coming out of the probe heads, this single-mode design further eliminates or reduces any differences between different modes that propagate in the same optical path.

Figure 21:
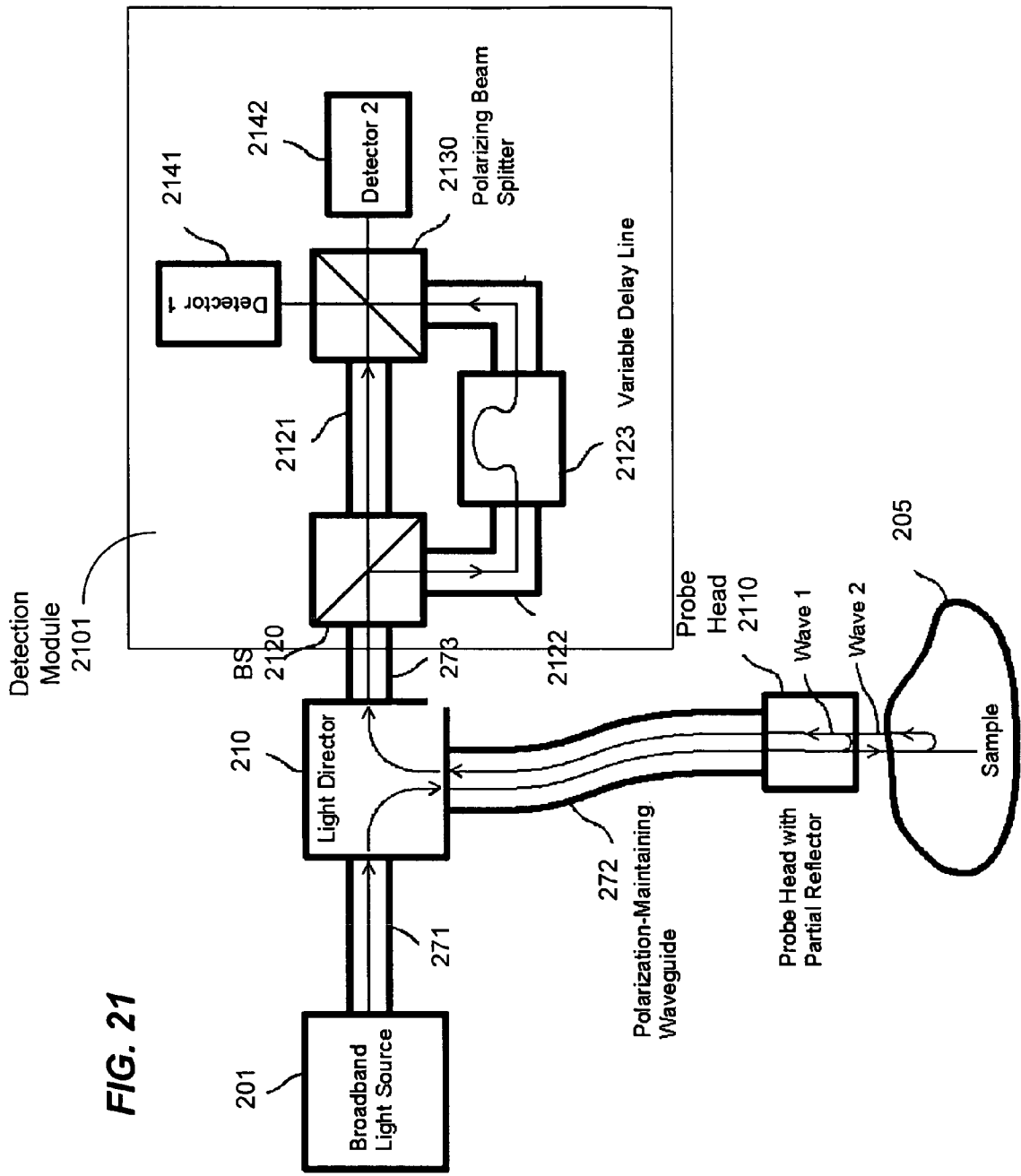
FIGS. 21 and 22 shows examples of optical sensing devices that direct light in a single mode to the optical probe head and direct output light from the probe head in the same single mode.

FIG. 21 shows one exemplary system for acquiring information of optical inhomogeneity and other properties in substances with only one propagation mode inside waveguides. A broadband or low-coherence light from Broadband Light Source 201 is directed to a probe head 2110 by means of polarization-maintaining waveguides 271 and 272. A partial reflector inside the probe head 2110 reverses the direction of a small portion of the input light to create a radiation wave 1 while transmitting the remainder of the input light to the sample 205. Backscattered or reflected light from the sample 205 becomes a second radiation wave 2 and is collected by the probe head 2110. The probe head 2110 combines and couples both the radiation waves 1 and 2 back into the waveguide 272. The radiation waves 1 and 2 travel in the waveguide 272 towards Light the light director 210 which directs radiation waves 1 and 2 through the waveguide 273 towards the detection module 2101. Notably, the radiation waves 1 and 2 output from the probe head 2110 are in the same mode as the input light to the probe head 2110. the probe head 2110 does not change the mode of light when directing the radiation waves 1 and 2 to the waveguide 272.

The detection module 2101 includes a beam Splitter 2120, two optical paths 2121 and 2122, an optical variable delay element 2123 in the path 2122, a beam combiner 2130, and two optical detectors 2141 and 2142. The beam splitter 2120 splits the light in the waveguide 273, which includes the radiation waves 1 and 2 in the same mode, into two parts that respectively propagate in the two optical paths 2121 and 2122. Notably, each of the two parts includes light from both the radiation waves 1 and 2. The variable delay element or delay line 2123 in the optical path 2122 is controlled by a control signal to adjust the relative optical delay between the two optical paths 2121 and 2122 and may be implemented by, e.g., the exemplary delay elements described in this application and other delay designs. The beam combiner 2130 combines the signals of the two optical paths to overlap with each other and to output two optical signals for optical detectors 2141 and 2142, respectively. The beam combiner may be a polarization beam splitter which splits the combined light into two parts, orthogonal in polarization to one another.

The probe head 2110 may include a partial reflector to produce the radiation wave 1 which does not reach the sample 205. Assuming the single propagation mode for the light to the probe head 2110 and the light out of the probe head 21110 is a polarization mode, the light reflected from the partial reflector in the probe head 2110, i.e., the radiation wave 1, has the same polarization as the light collected from the sample, the radiation wave 2. Therefore, both Radiation 1 and 2 travel in the same propagation mode in the waveguides, 272 and 273. Because the radiation waves 1 and 2 are reflected from different locations, they experience different optical path lengths when reaching the beam splitter 2120. The effect of variable delay element 2123 is to add an adjustable amount of the delay in the light in the path 2122 relative to the light in the path 2121.

In operation, the variable delay element 2123 can be adjusted so that the partial radiation 1 reaching the polarization beam splitter 2130 through the path 2122 can be made to experience a similar optical path length as the partial radiation 2 reaching the beam splitter 2130 via the other path 2121. The superposition of the two beams at the photo detectors 2141 and 2142 causes a measurable intensity variation as their relative path length is being varied by the variable delay element 2123. This variation can be utilized to retrieve information on the inhomogeneity and other properties of the sample 205.

Figure 22:
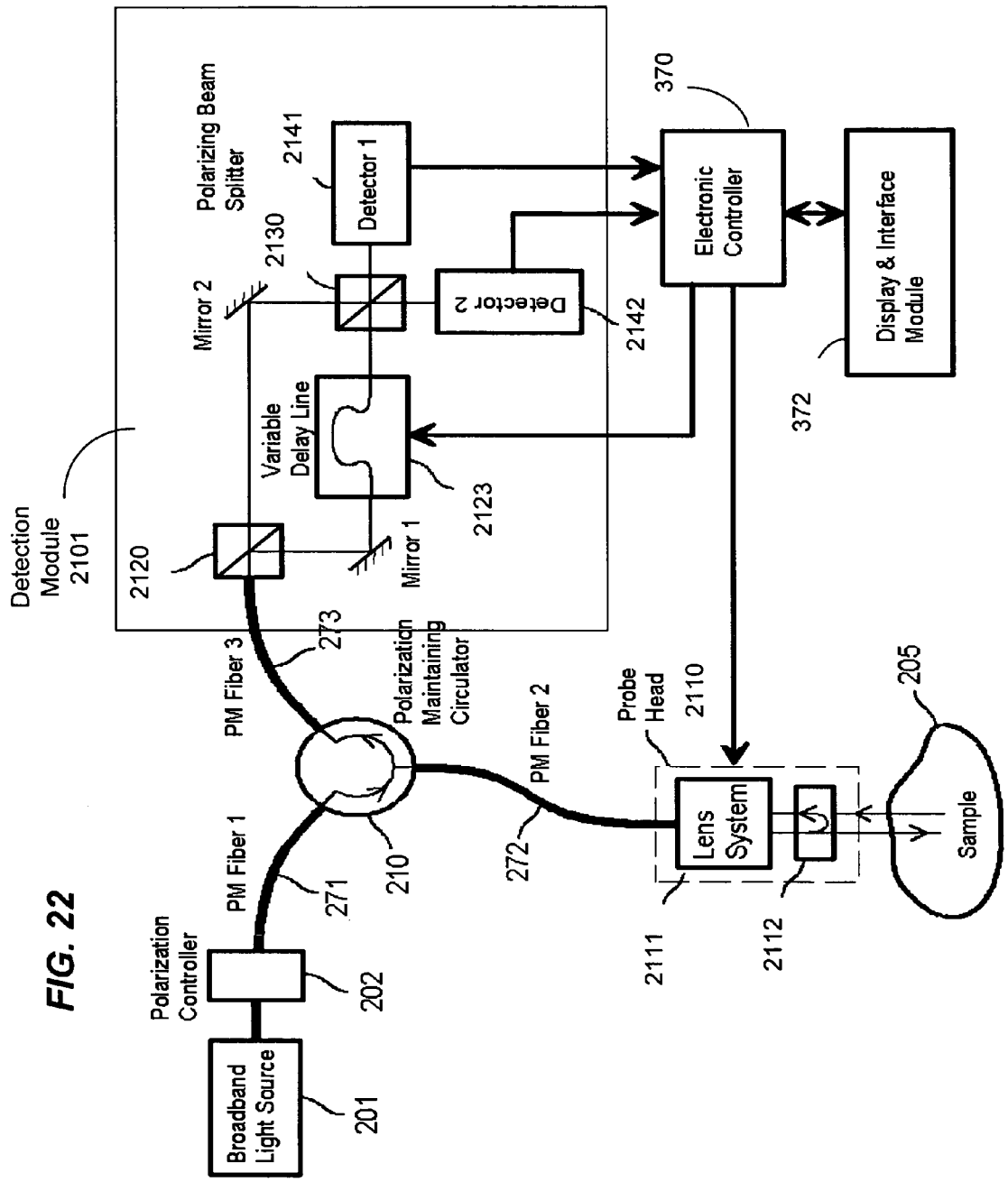

FIG. 22 shows an exemplary implementation of the system in FIG. 21 using polarization maintaining optical fibers. A polarization controller 202 may be placed at the output of the light source 201 to control the polarization of the input light in one polarization mode. The optical head 2110 is shown to include a lens system 2111 and a partial reflector 2112. Two mirrors 1 and 2 are used to construct the two optical paths between the beam splitters 2120 and 2130. The optical radiation reflected from the partial reflector 2122 and from the sample 205 travel in the polarization-maintaining (PM) fiber 272 in the same mode. The main portions of the radiation waves 1 and 2 are deflected to the mirror 1 while the remaining portions are directed to the mirror 2 by the beam splitter 2120.

The incident plane of the polarizing beam splitter 2130 can be made to have a finite angle with respect to the polarization directions of light from both the Mirror 2 in one optical path and the variable delay element 2123 from the other optical path. In this configuration, light energies received by both detectors 2141 and 2142 are the superposition of the two radiations, i.e., Radiation 1 and Radiation 2. It should be appreciated that the linkage between the beam splitters 2120 and 2130 can be made by means of optical fibers or other optical waveguides to eliminate the free space paths and the two mirrors 1 and 2.

In the examples shown in FIGS. 21 and 22, the spacing between the optical head 2110 and the sample 205 may be greater than the sample depth of interest so that, upon reaching the beam splitter 2130, the partial radiation 1 experiences optical path length similar only to that of partial radiation 2. In other words, split parts of the same radiation do not experience similar optical path length during the operation of the systems in FIGS. 21 and 22.

Figure 23:
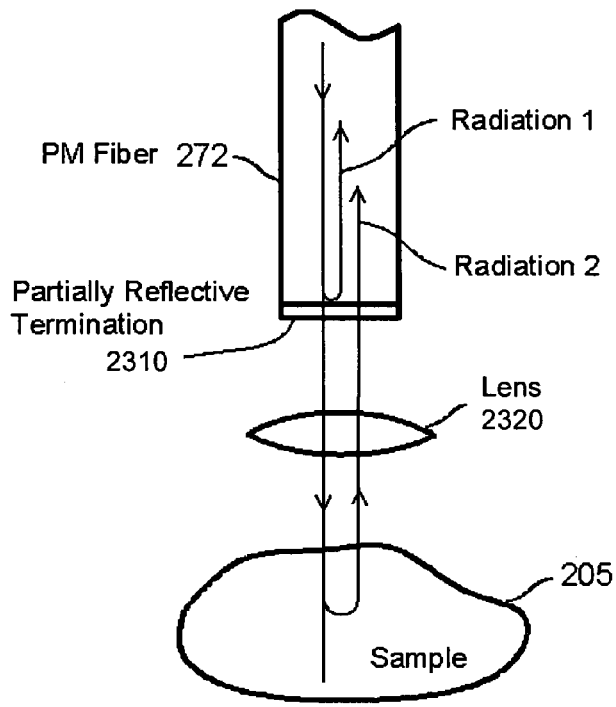
FIG. 23 shows an example of a design for the optical probe head for the devices in FIGS. 21 and 22 where the optical probe head does not change the mode of light.

FIG. 23 shows one exemplary optical arrangement for the probe head 2110. The partial reflector 2310 can be realized with a partially reflective fiber termination, i.e., the end facet of the fiber 272. An uncoated fiber tip has a reflectivity of approximately 4% and thus may be used as this partial reflector. Optical coating on the end facet may be used to change the reflectivity to a desirable value.

The reflectance of the fiber termination 2310 may be chosen based on several factors. In one respect, the radiation wave 1 should be strong enough so that its superposition with the radiation wave 2 creates an adequate intensity variation at the two detectors 2141 and 2142. On the other hand, the radiation wave 1 may not be too strong as it may overwhelm the photodetectors 2141 and 2142, prohibiting the use of high gain in the detection systems. For optimized operation of the system, one may want to choose the reflectance of the fiber termination to be comparable to the total light collected by the fiber from the sample.

In FIGS. 21 and 22, a common waveguide 272 is used for both sending input light into the probe head 2110 and directing output light output the probe head 2110. Alternatively, similar to the design in FIG. 15, the waveguide 272 may be replaced by an input waveguide for sending input light into the probe head 2110 and an output waveguide directing output light output the probe head 2110 to the beam splitter 2120 of the detection module 2101. In this design, the light director 210 can be eliminated and the optical probe head 2110 may be designed to direct output light with both the radiation waves 1 and 2 into the output waveguide.

Similar to tuning the frequency of light in other examples as described, in implementing the devices in FIGS. 21 and 22, a tunable optical bandpass filter may be used to tune the frequency band of the light to selectively measure the property of the sample 205 at the frequency band of the filter. In addition, the use of gratings in the detection module to measure different spectral components of the sample as shown in FIG. 20 may be used in the module 2101 as well.

Figure 24:
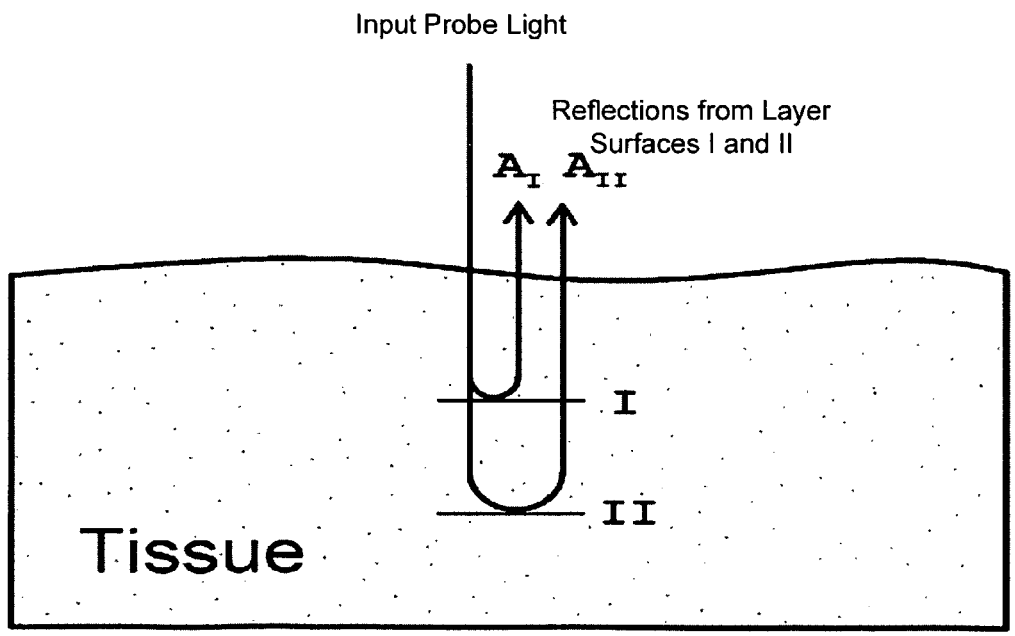
FIG. 24 illustrates two selected surfaces underneath a surface of a body part in optical spectral absorbance mapping measurements.

FIG. 24 further illustrates the measuring technique for optically targeting a layer underneath the surface of a body for its spectral absorbance. Referring to Equations (15)-(17), the optical differential delay can be adjusted to obtain the measurements $A_I$ and $A_{II}$ from the two depths I and II in order to obtain measurement for the layer between the depths I and II. If the center wavelength of the light source λ is scanned to obtain measurements at different wavelengths, the measured ratio in Equation (17) can be used to obtain spectral absorption characteristics of the substance bounded by interfaces I and II only, i.e. $\mu_h(\lambda)$. Therefore, this techniques effectively isolates the substance between I and II in terms of its spectral absorbance for the measurement. This procedure can be carried out for all layers, by varying the depths of the interfaces I and II, to obtain a cross-sectional spectral absorbance mapping (SAM).

One way to obtain SAM measurements is to first obtain the cross-sectional maps of the reflectance, $A(\lambda)$, at two or more different wavelengths using light radiations centered at these wavelengths. When a single light source is used as described above, a tunable optical filter is used to select the different wavelengths at each spatial location of the probe head over the target area to obtain measurements. Upon completing measurements at different wavelengths at one location, the probe head is moved to the next location and the measurements repeat. This process continues until all locations within the target area are measured. This use of the optical differential delay at variable delay values and the scan along the target surface in combination effectuates a 3-dimensional mapping of the spectral absorbance of the target area.

In some applications where the sample has absorption features in a broad spectral range, a single light source may not be able to provide a sufficiently broad spectral coverage over these absorption features. The following sections describe techniques that use two or more light sources with radiations centered at different wavelengths to provide a broad spectral coverage in SAM measurements.

Various optical arrangements described here can be adopted for performing SAM measurements. Several examples are described below for using multiple light sources at different wavelengths.

Figure 25:
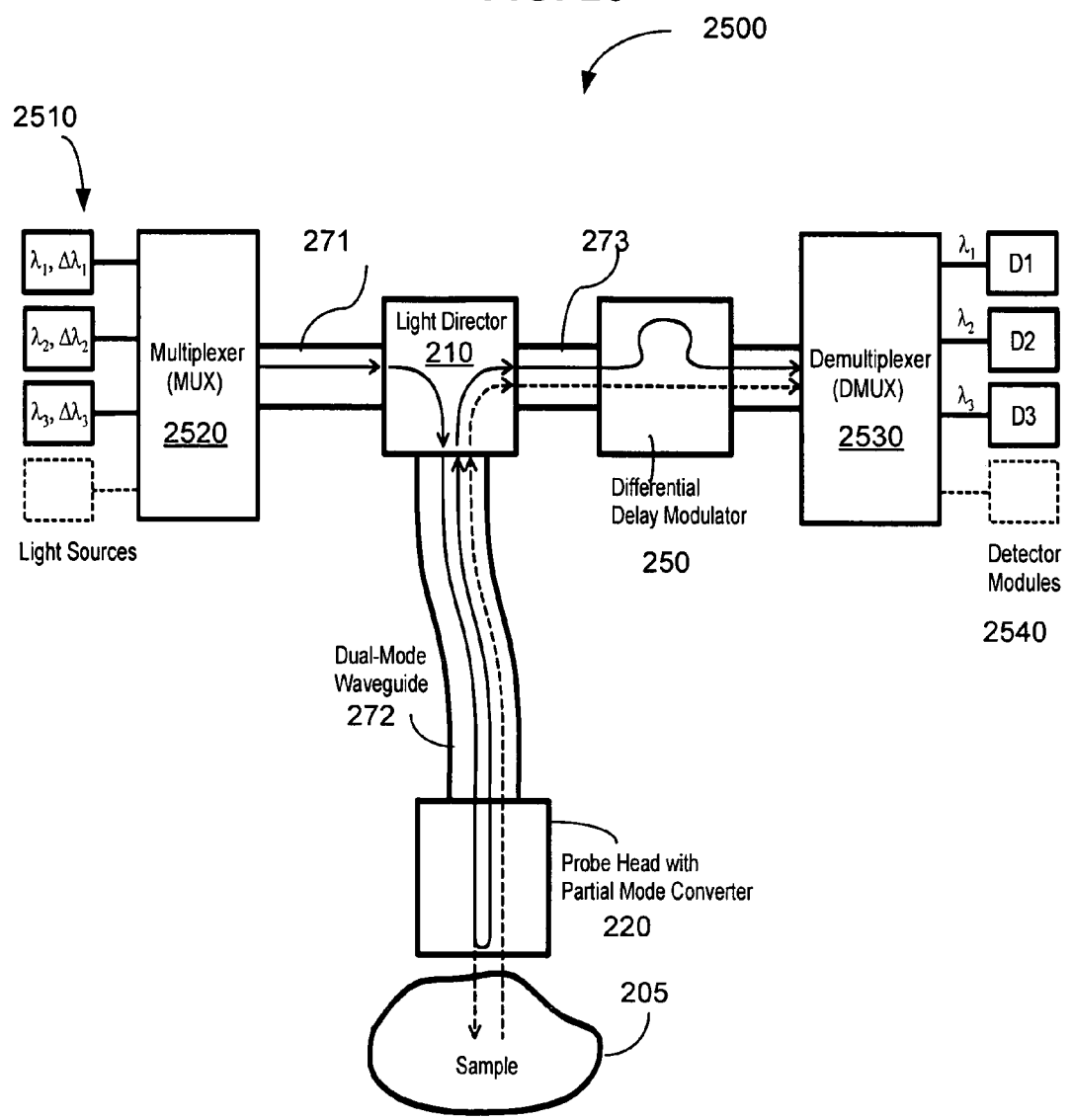
FIGS. 25, 26 and 27 show examples of devices that use multiple light sources at fixed center emitting wavelengths for spectral absorbance mapping measurements.
Figure 31:
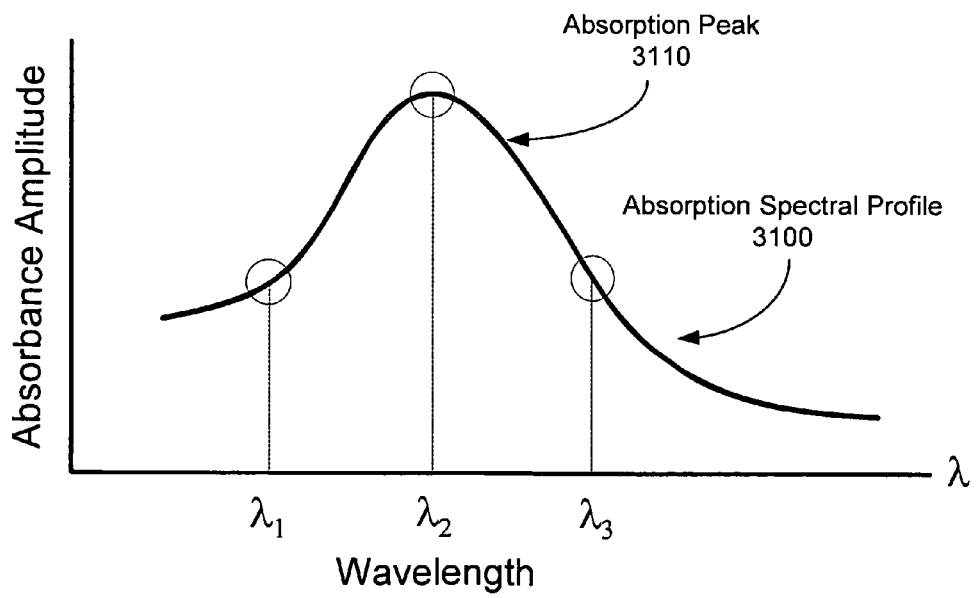
FIG. 31 illustrates an example for using different beams at different wavelengths to detect an absorption feature in a sample in spectral absorbance mapping measurements.

FIG. 25 shows an optical device 2500 that uses two or more different light sources 2510 at different optical wavelengths to obtain reflectance maps from a sample. Each light source emits within a bandwidth Δλ centered at a different wavelength from other light sources. The wavelengths of the light sources 2510 can be selected to cover the spectral range of the absorption features in samples to be measured. In some applications, the wavelengths of 2510 may be selected to effectively sample a specific absorbance feature of interest, as shown in FIG. 31. and thus may not cover other absorption features in the sample. In a specific implementation, the bandwidth $\Delta\lambda$ of each light source should be selected with consideration of the depth spatial resolution desired for the measurements. An optical multiplexer 2520 is used to receive the optical radiations from different light sources 2510, to combine these optical waves into a common optical path, i.e., the common optical waveguide 271. The light director 210 directs the combined optical radiation to the probe head 220 via a common waveguide 272. The probe head 220, which is positioned above the sample 205, split a portion of light from the multiplexed or combined optical radiation as the probe light and direct this probe light to the sample 205. The reflected light from the sample 205 is collected by the probe head 220 and is directed to the differential delay modulator 250 via the waveguide 272, the light director 210 and another waveguide 273. Details, various implementations and operations of the device 2500 are described in previous sections. An optical demultiplexer 2530 is further used to separate the light output from the differential delay modulator 250 spatially based on different wavelength bands centered at the different wavelengths of the light sources 2510. Accordingly, an array of different optical detector modules 2540 are used to respectively receive and detect the separated beams of different wavelength bands. As an example, light radiation centered at the wavelength $\lambda_1$ and within the bandwidth of $\Delta\lambda_1$ from one light source is separated from the rest and sent to the detector module 1 (D1). Each detector module may include one or multiple optical detectors. The differential delay modulator 250, the demultiplexer 2530 and the detector modules 2540 form at least part of an optical correlator which performs the optical detection of the device 2500. The multiplexed light radiations are delivered to the tissue through the optical waveguide 272 or fiber and the probe head 220. Backscattered and reflected light from the tissue is collected in part by the probe head 220 and redirected to the optical correlator.

In practice, the probe head 220 is operated to scan the multiplexed light radiation over the sample 205 to obtain measurements at different wavelengths. For every designated spatial interval the differential delay modulator 250 scans over a range to correspond to a range of depth inside the sample. This process repeats until all sampling locations of an area of the sample are measured. In this implementation, cross-sectional maps for light radiations at two or more wavelengths can be simultaneously obtained. While the differential delay modulator 250 and the probing light radiation are being scanned, the photocurrents from the detector modules 2540, each receiving light radiation within a different wavelength band associated with one of the light sources 2510, can be simultaneously recorded as the data from which the multiple reflectance maps, $A(\lambda_1)$, $A(\lambda_2)$ and so on, can be extracted. Each reflectance map is formed by radiation within the band of one light source. These reflectance maps can then be used to derive SAM using an algorithm based on the principles outlined by Equations (15) through (17).

Figure 26:
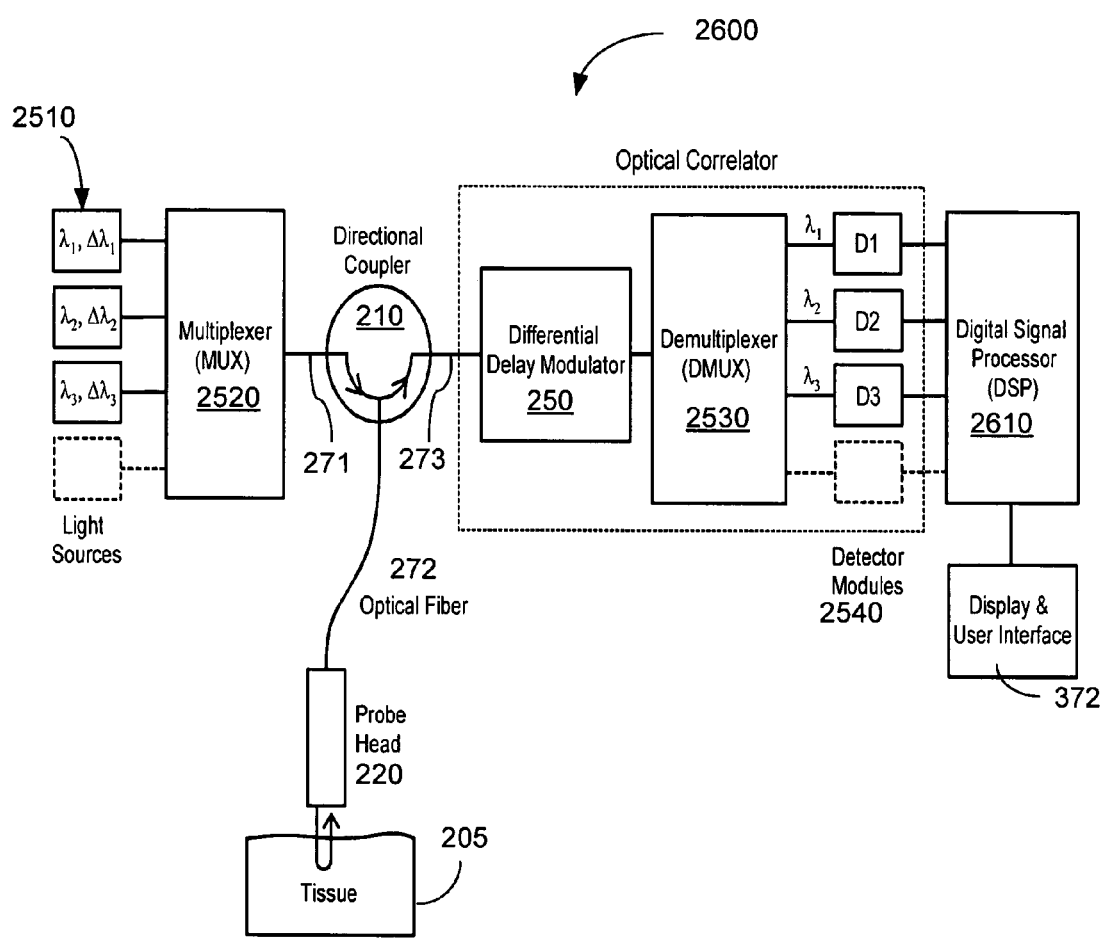

FIG. 26 shows one implementation 2600 of the device 2500 in FIG. 25 where a digital signal processor (DSP) 2610 is used to process the detector outputs from the detector module 2540 and to produce the spectral absorption map. The DSP 2610 may be part of the device controller 370 shown in FIG. 3. A display and user interface module 372 is used to allow an operator to view the SAM result and to control the device.

Figure 27:
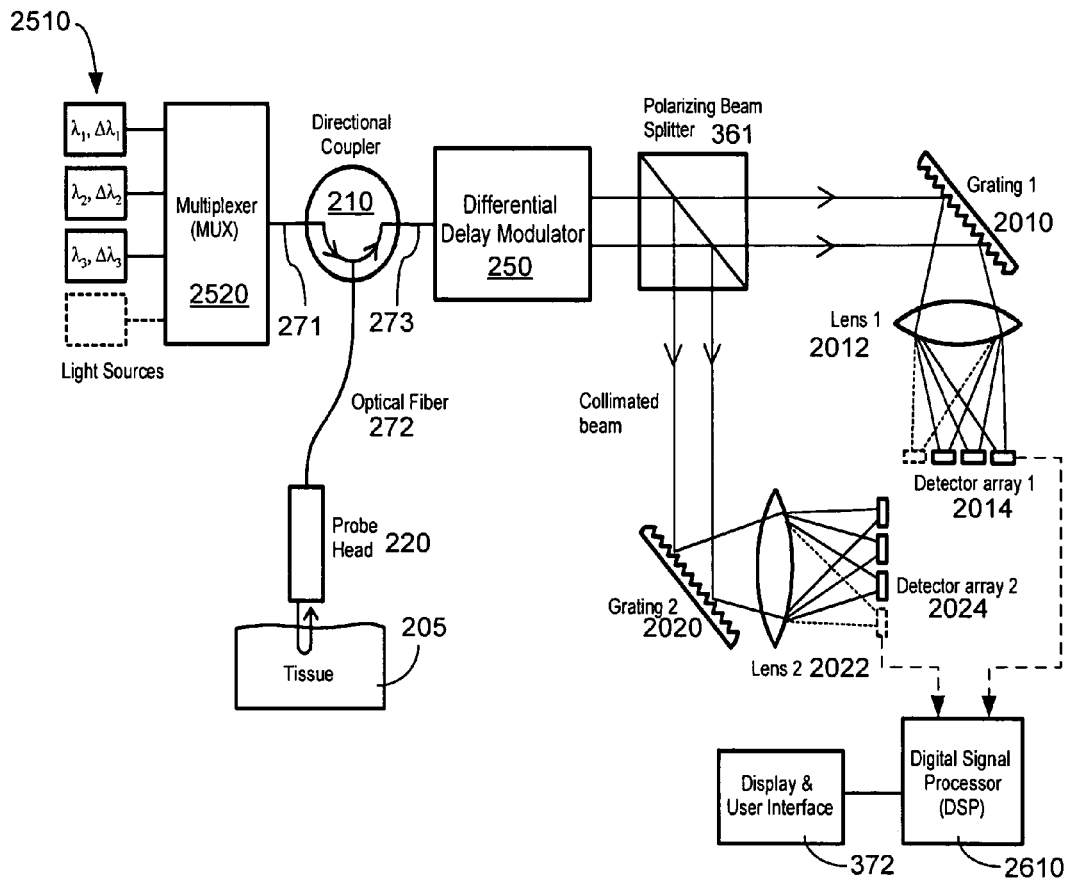

FIG. 27 shows an example of the device 2600 in FIG. 26 where the demultiplexer 2530 is implemented with two gratings 2010 and 2020 and two lenses 2012 and 2014. The detector modules 2540 are implemented with two detector arrays 2014 and 2024, i.e., each of the detector modules 2540 includes one detector in the array 2014 and another detector in the array 2024 for detecting light at the same wavelength and in different polarization states. The polarization beam splitter 361 split the wavelength multiplexed light from the differential delay modulator 250 into two beams with mutually orthogonal polarization states where each split beam is a mixture of light in two different modes from the probe head 220. The polarization beam splitter 361 converts a part of received light in the first propagation mode and a part of received light in the second propagation mode into light in a third propagation mode that propagates along a first optical path and to convert remaining portions of the received light in the first and the second propagation modes into light in a fourth propagation mode that propagates along a second, different optical path. The third and fourth modes are two orthogonal polarization modes of the polarization beam splitter 361.

The gratings 2010 and 2020 separate the wavelength multiplexed light radiation into angle intervals, each corresponding to the light from one of the light sources 2510. The number of photosensitive elements in one detector array can be equal to the number of light sources used. The sensing area of each of the photosensitive elements may be designed to be sufficiently large so that all the light radiation within the band of one light source can be received by one element in the array. For instance, if three light sources are used in the system, two arrays each with three photosensitive elements may be used.

Figure 28:
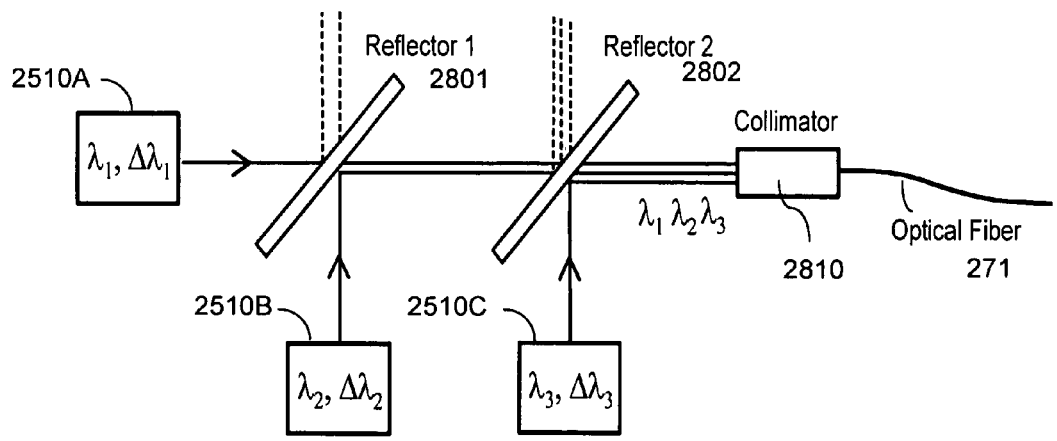
FIG. 28 shows one example of an optical multiplexer to combine beams from different light sources into a common waveguide or optical path.

The optical multiplexer 2520 may be implemented in various configurations. FIG. 28 shows one example of the multiplexer 2520 where partially reflective mirrors 2810 and 2802 are used to multiplex radiation beams from three different light sources 2510A, 2510B and 2510C. The design can be used with N partially reflective mirrors to multiplex beams from (N+1) light sources. The partially reflective mirrors can be manufactured by coating one side of a glass with a thin metal layer. With this arrangement not all the light power will be multiplexed into the optical fiber, as loss of optical power occurs at each reflector. An optical collimator 2810 is used to couple the multiplexed light into the optical waveguide or fiber 271.

Figure 29A:
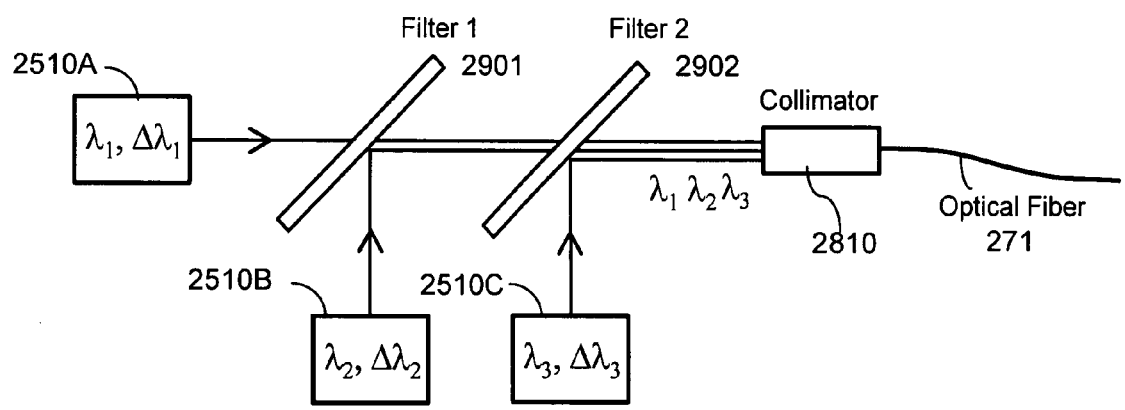
FIGS. 29A and 29B show another example of an optical multiplexer with dichroic filters to combine beams from different light sources into a common waveguide or optical path and the spectral properties of the dichroic filters.

FIG. 29A shows another example of the multiplexer 2520 which reduces the optical loss in the design in FIG. 28 and provides an efficient use of the available optical power. In this example, optical dichroic filters 2901 and 2902 are used to replace the partially reflective mirrors 2801 and 2802, respectively. A Dichroic filter may be implemented in various forms. One implementation is to use two short-pass interference filters as the dichroic filters 2901 and 2902.

Figure 29B:
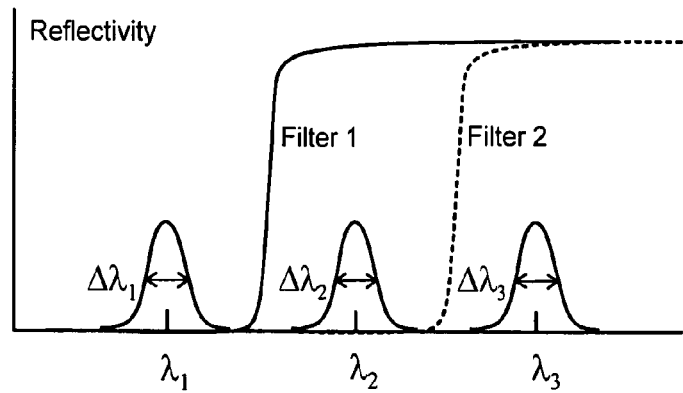

FIG. 29B shows the optical designs of the dichroic filters 2901 and 2902. The cut-off wavelength of the filter 2901 is set between the radiation bands of the first and second light sources centered at $\lambda 1$ and $\lambda 2$, respectively; that of the filter 2802 set between the radiation bands of the second and the third light sources centered at $\lambda 2$ and $\lambda 3$, respectively. With this arrangement, except for the imperfection of the filters, all radiation from the three light sources are coupled into the optical fiber 271 without significant optical loss. Interference optical filters of this kind can be fabricated using multilayer dielectric thin films. Other possible multiplexers include arrayed waveguide type and grating type.

Figure 30:
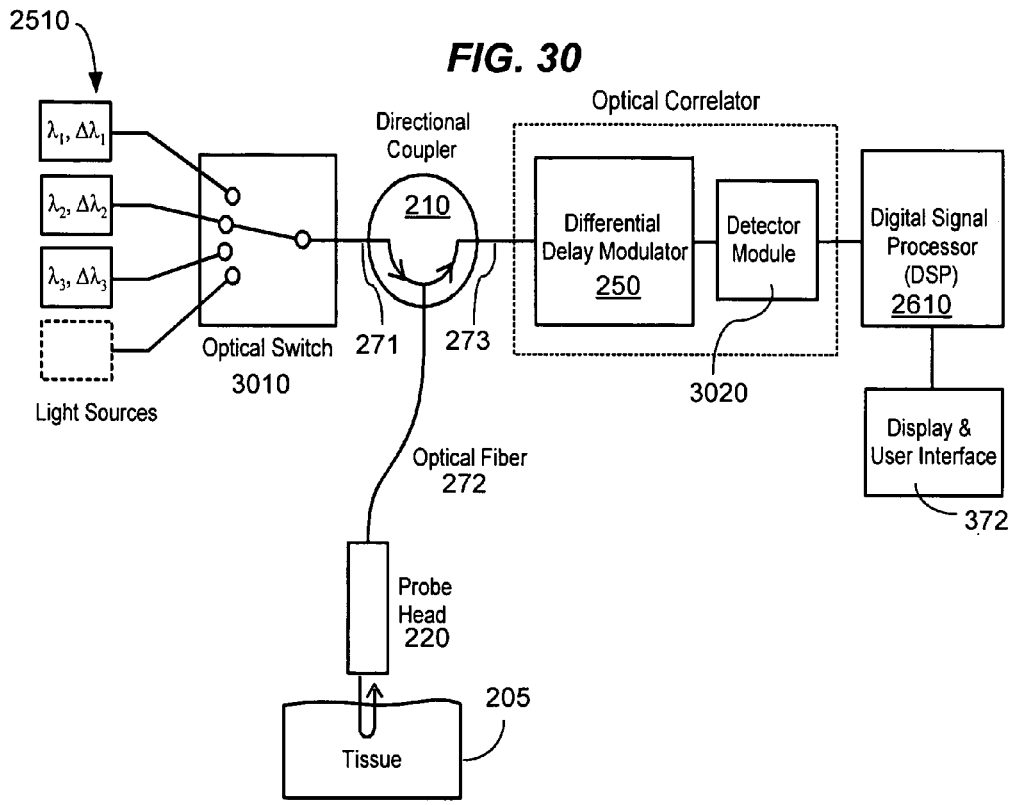
FIG. 30 shows an exemplary device that uses multiple light sources at fixed center emitting wavelengths for spectral absorbance mapping measurements, where an optical switch is used to sequentially direct different beams from different light sources into a common waveguide or optical path.

In the above devices for SAM measurements, light beams at different wavelength bands are simultaneously directed by the probe head 220 to the sample 205. Hence, the optical measurements at different wavelengths are performed simultaneously. Alternatively, the optical multiplexer 2520 may be replaced by an optical switch 3010 as shown in FIG. 30 to direct a probe beam within one of the wavelength bands at a time so that probe light beams at different wavelength bands are directed to the sample 205 sequentially at different times to obtain the reflectance maps. In one implementation, the N broad band light sources 2510 can be sequentially linked to the optical device in FIG. 30 through a 1×N optical switch as the switch 3010. The reflective maps, $A(\lambda_1)$, $A(\lambda_2)$ and so on at different wavelength bands are obtained sequentially and are then used in the calculation of SAM.

The choice of the broadband light sources in any of the above device designs can be made according to the specific absorption features to be measured. As an example, FIG. 31 shows an absorbance amplitude spectrum 3100 of a sample where an absorption peak 3110 is present. Three or more different broadband light sources with the center wavelengths shown may be used to map the peak 3110. To achieve a better spectral resolution, the number of the light sources may be increased. In the example of three light sources, the reflectance maps at the three different wavelengths, i.e., $A(\lambda_1)$, $A(\lambda_2)$ and $A(\lambda_3)$, can be used to calculate the strength of the feature for SAM.

The axial resolution (i.e., the depth resolution) of SAM is related to the bandwidth (spectral width), $\Delta\lambda$, of the light source at a center wavelength $\lambda_0$ is given by the following:

$$\Delta z = \frac{2\ln(2)}{\pi} \frac{\lambda_o^2}{\Delta\lambda} \quad (23)$$

For a given bandwidth, $\Delta\lambda$, the depth resolution of the corresponding reflectance map is determined by the above equation. Hence, a broad bandwidth is desirable for resolving a small spatial feature along the direction of the probe beam, which limits the spectral resolution as a tradeoff. For example, if one wants to map an spectral absorbance feature that occupies a 20 nm range near an optical wavelength of 1 µm, light sources of bandwidth around 5 nm can be chosen. Under these conditions, the spatial resolution for SAM is roughly 90 µm.

In the above multi-source SAM measurements, each light source has a fixed emission center wavelength and a bandwidth. In other implementations based on the above-described designs, multiple tunable laser sources may be used to replace the fixed light sources. Each tunable laser source may be configured to provide highly coherent radiation over a wavelength range of $\Delta\lambda$ centered at $\lambda$. Due to the same consideration that a spectral absorbance feature of interest may be too broad for a single tunable laser source to cover, two or more tunable laser sources, each tunable over a wavelength range centered at a different wavelength, can be implemented in various designs for SAM measurements.

Figure 32:
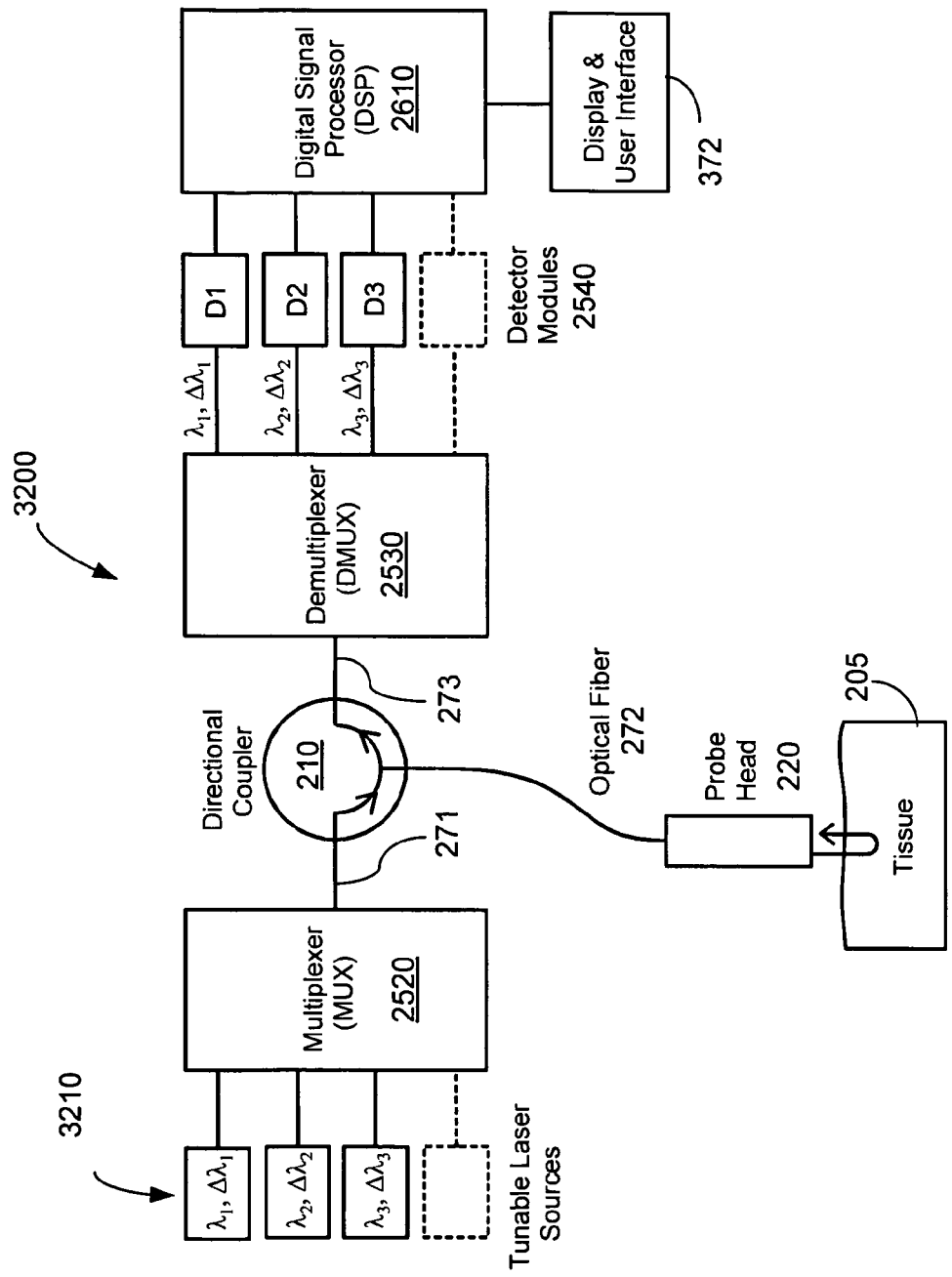
FIG. 32 shows an exemplary device that uses multiple tunable light sources for spectral absorbance mapping measurements.

FIG. 32 illustrates one example of a device 3200 for SAM measurements where two or more tunable lasers 3210 are used as the light sources. The optical radiations from the tunable laser sources 3210 are combined through the multiplexer 2520 before being guided to the probe head 220. The light waves from the probe head 220, including what is collected from the tissue under examination, are redirected towards the demultiplexer 2530 where they are separated into separated beams in different optical paths according to the wavelength bands, each of which is received by an optical detector.

This arrangement may be configured to allow for the simultaneous tuning of the wavelengths of the tunable laser sources 3210, which in turn allows for the simultaneous recording of the light waves from the probe head 220 in the different wavelength bands. One feature in the design in FIG. 32 is the lack of the optical differential delay modulator 250 used in other designs where one or more fixed light sources are used to produce the probe light. Each tunable laser is tuned through its tuning spectral range during the measurement and the recorded light intensity as a function of the laser wavelength in each of the bands can be computed to obtain a reflectance map for that band. The reflectance maps, for the various center wavelengths, can be computed by analyzing the photocurrents of the photodetectors as functions of the wavelength. A variation of the photocurrent with a certain wavelength periodicity indicates a reflection originated from a certain distance, or depth, in the sample 205. Such a computation is, in essence, a decomposition of the photocurrent according to its frequency, or commonly known as a Fourier transformation. In order for the reflectance maps to cover a range of the depth the tunable lasers should have an adequate coherent length which is comparable or longer than the range of the depth. Two or more reflectance maps for two or more wavelength bands can be obtained for the sample 205 under examination and can be used to derive the SAM of the sample 205 based on Equations (15)-(17).

This use of the tunable lasers may be implemented in the various device designs for SAM measurements by removing the optical differential delay modulator 250. For example, the design in FIG. 30 may be used, without the differential delay modulator 250, to sequentially direct light radiations from different tunable laser sources to the sample 205. When the radiation from a particular tunable laser is directed to the sample 205, the laser is tuned in its laser frequency through its tuning range to obtain measurements of the optical absorption at different wavelengths within the tuning range.

In some precise optical phase measurements using the above described techniques with tunable laser sources, a differential phase modulator 250 may be inserted in the common waveguide 273 to receive the light from the probe head in the first and second propagation modes and to produce and modulate the relative optical phase between the first and second propagation modes. The modulation of the relative optical phase between the first and second propagation modes causes the photocurrents out of the photodetectors 2540 (or detectors in the detector arrays 2014 and 2024) to shift their peak positions and valley positions with respect to the wavelength. This allows for accurate calculations of the reflected optical phase of the light reflected from the sample using mathematical analysis similar to the analysis represented by Equations 12 and 13.

Figure 33:
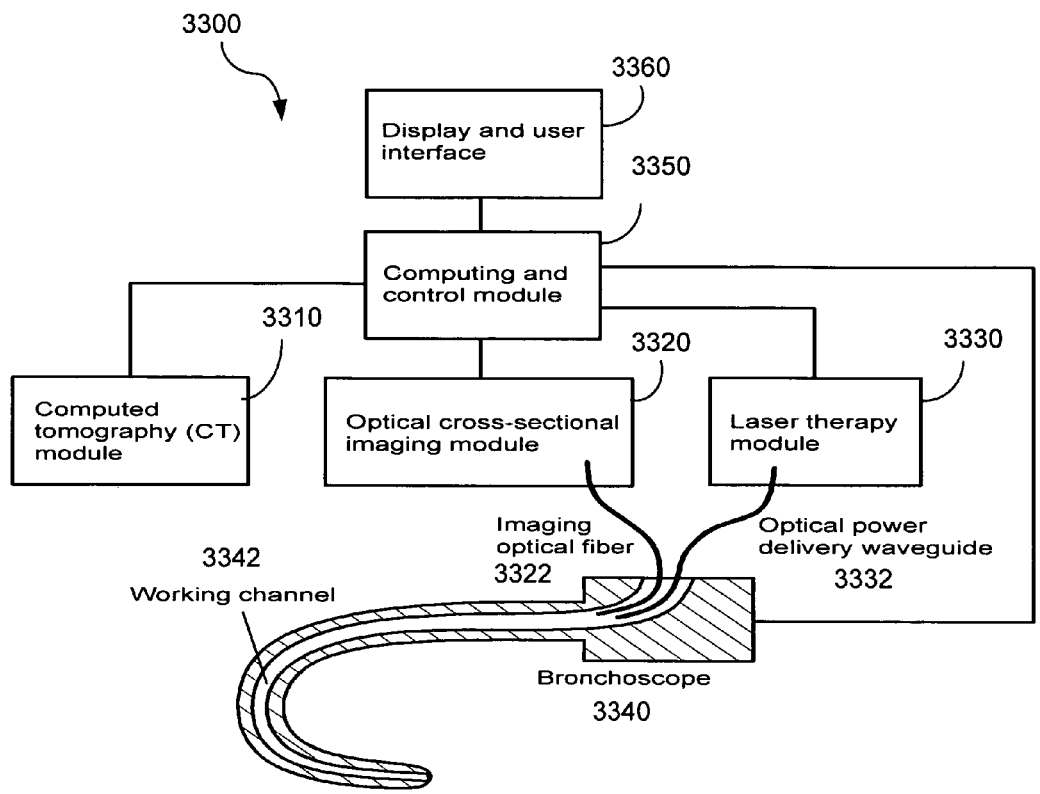
FIG. 33 shows an example of an integrated system that combines an X-ray CT scan module, a reference cross-sectional tissue imaging module, and a laser treatment module to provide a complete diagnostic and treatment platform for treating lung cancer.

As an application of the above non-invasive optical probing techniques and devices, FIG. 33 shows an example of an integrated system 3300 that combines an X-ray CT scan module 3310 for locating pulmonary nodules, a minimally invasive optical probing module 3320, and a treatment module 3330 to provide a complete diagnostic and treatment platform for treating lung cancer. The treatment module 3330 may be designed to use electromagnetic radiation, such as laser radiation, RF or microwave radiation energy, to treat a malignant condition at a selected target area. A bronchoscope 3340 is used to provide a means for inserting the optical probe for the optical probing module 3320 into the lung to optically measure a target area in the lung. In addition, the bronchoscope 3340 is also used to guide the laser beam from the laser treatment module 3330 to the lung for laser treatment. As illustrated, the bronchoscope 3340 includes a working channel 3342 that is hollow and receives the optical probe head and optical fiber 3322 for the optical probing module 3320 and an optical power delivery waveguide 3322 for the laser treatment module 3330. The working channel 3342 is inserted inside the lung to probe different targeted areas in the lung. The distal end of the working channel 3342 includes an end facet or window that transmits both the optical probe light and the laser beam from the laser treatment module 3330. A computing and control module 3350 is provided to control the three different modules 3310, 3320 and 3330 and to perform analysis on the measurements. A display and user interface module 3360, which may include a user input interface and a display monitor, is used to allow an operator to operate the system 3300.

The CT scan module 3310 is used to scan the lung of a patient to detect and locate all solitary pulmonary nodules (SPNs). Each SPN is visually located via the CT scan imaging. Next, the optical probing module 3320 is used to measure each SPN identified by the CT scan. This is a differential diagnosis and the optical measurement is analyzed to determine whether each SPN is benign or malignant. The laser treatment module 3330 is then used to treat each malignant SPN. All three procedures can be performed in one integrated system.

The minimally invasive optical probing module 3320 may be implemented in various embodiments as described in this application. As a specific example, the optical probing module 3320 may be implemented as a cross-sectional imaging module. The optical module 3320 can be used to allow the anticipated use of CT scans in early stage lung cancer diagnosis and, in addition, can facilitate cancer therapy using optical methods such as Laser Hyperthermia. The module 3320 utilizes optical correlation techniques to obtain optical tomographs to non-destructively reveal the tissue structure and other physiological information. The probe head of the imaging module 3320 is fiber optic-based and is inserted into the working channel 3342 of the bronchoscope 3340. The bronchoscope 3340 has been previously used to visually locate the tumor inside the lung. A sequential, in-vivo examination of the suspect tissue or SPN with the optical probing module 3320 can distinguish a calcified, benign SPN from a malignant one by virtue of their different structure and optical properties. This use of the optical probing module 3320 resolves the CT scan diagnostic dilemma, enabling an minimally invasive procedure to locate SPNs and then identify which nodules are malignant. Notably, the use of this diagnostic sequence based on the optical probing allows the physician to avoid most, if not all, pulmonary biopsies, thereby significantly reducing the risks discussed above and greatly improving chances for a successful diagnosis without side effects.

Figure 34:
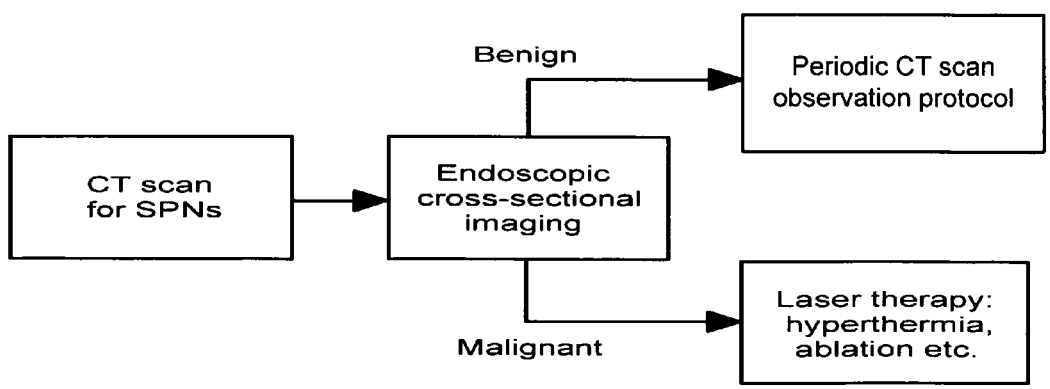
FIG. 34 shows one exemplary use of the system in FIG. 33 in detecting and treating lung cancer.

FIG. 34 illustrates one exemplary use of the system 3300 in FIG. 33. The CT scan is used to perform the initial examination of the lung to scan for all SPNs, benign and malignant. After the CT scan, the optical probing is performed at each detected SPN to determine whether the SPN is benign or malignant. If a SPN is determined to be malignant, the laser treatment can be performed to treat the malignant condition of the SPN by using the laser treatment module 3330. If no malignant SPN is found, the patient may be scheduled for periodic CT scans to monitor the condition of the lung.

TABLE 1

| Assumed Tumor diameter | 1 cm. |
| Approx. Tumor Volume | 0.5 cc |

TABLE 1-continued

| Optical Power delivered | 0.5 watt | 1.0 watt | 2.0 watts |
| Estimated Laser Power | 1.5 watt | 3.0 watt | 6.0 watt |
| Temperature Rise for: | | | |
| 5 sec. Exposure | +5 C. | +10 C. | +20 C. |
| 10 sec. Exposure | +10 C. | +20 C. | +40 C. |

The laser treatment may be implemented in various configurations such as laser hyperthermia treatment and laser ablation treatment. For example, a pulmonologist may use a high power laser in the laser treatment module 3330 and an optical fiber-based therapeutic probe inserted into the working channel 3342 of the bronchoscope 3340 to deliver optical power to the tumor. This procedure, called Laser Hyperthermia, has been shown to necrotize cancerous tissue. The laser emission wavelength is chosen so that essentially all of the light is absorbed by the tissue, e.g., within first centimeter of tissue. Several types of high power laser sources may be used. For example, compact, powerful diode-pumped solid state lasers are readily available. Optical fibers capable of transmitting substantial power levels (e.g., on the order of watts) are also available. We estimate that coupling of the laser optical power to the fiber can be accomplished with approximately 33% efficiency using normal methods known to practitioners in this field.

As an example, Table 1 lists calculated exposure times needed to elevate the temperature of the suspect tissue for different optical power levels delivered to the tissue. The laser power input to the optical delivery waveguide 3332 (e.g., optic fiber) would need to be three times higher assuming 33% coupling efficiency. In the above estimates, it is assume that the malignant tissue behaves thermally as if it were water (about 70% accurate) and that the nodule is essentially in poor thermal contact with the surrounding tissue. Researchers have found that a 10° C. rise in temperature is sufficient to kill cancer cells and that higher temperature rises kill malignant cells more quickly. Base upon the results of Table 1, a 3-6 watt laser should suffice to perform Laser Hyperthermia in-vivo with a 5-10 sec. exposure.

The integrated diagnostic and therapeutic system in FIG. 33 and the technique in FIG. 34 may be implemented to allow both SPN location/detection and bronchoscopic examination to be performed in a single session or visit. In addition, both differential diagnosis and laser therapy can therefore be performed during a single bronchoscopic procedure. Therefore, The three different procedures, SPN detection/location, malignant-benign differential diagnosis, and remedial therapy, can be performed in a single office visit. A CT Scan system may be modified to incorporate the much smaller optical devices for differential diagnosis and laser therapy so that the complete process may be performed on a single piece of equipment. This results in very efficient use of the physician's time and convenience for the patient. Laser therapy methods, such as laser hyperthermia and laser ablation, do not have significant adverse side effects on the patient under treatment and thus are advantageous in this regard in comparison with other therapeutic regimens such as chemotherapy and radiation. In addition, the integrated system in FIG. 34 may be implemented to reduce any delay in the differential diagnosis and therapy and thus such implementation can be advantageous over other methods that use the 'wait-and-see' observation of tumor size growth protocol which is often employed to distinguish between malignant and benign SPNs.

The integrated system in FIG. 33 may also be implemented by using treatment modules other than laser therapy modules. Various electromagnetic radiation therapies using the radiofrequency (RF) energy and microwave energy for ablation may be used. An RF or microwave waveguide probe may be inserted into the working channel 3342 to deliver the RF or microwave energy to a targeted SPN for treatment. For example, the laser treatment module 3330 may be replaced by a microwave ablation therapy unit. The distal end facet of the working channel can be made to transmit both the probe light and the RF/microwave radiation.

In addition, the integrated design shown in FIG. 33 may also be implemented for diagnosing and treating other illness. In one implementation, for example, an integrated diagnostic and treatment system may include a CT scan unit to locate ailing areas in a body part, a referenced cross-sectional imaging unit to analyze each ailing area, and a laser, RF or microwave irradiation therapy unit to treat a selected area. This system may be used to diagnose and treat lung cancer, prostate cancer and other tumors. One specific implementation of this system is the example in FIG. 33 for diagnosing and treating lung cancer where a bronchoscope is inserted into the lung for deliver the probe light and the treatment laser beam.

In implementing the system in FIG. 33, the optical probe head 220 of the optical imaging module 3320 and the therapy delivery waveguide 3332 may be unified as a single assembly when inserted inside the working channel 3342 so that the treatment radiation, which may be laser radiation, RF or microwave radiation, can be directed to approximately the same location where the optical probe head 220 is located. In this design, when a SPN is identified as malignant, the treatment radiation can be delivered to the same location where the malignant SPN is without changing the location of the distal tip of the working channel 3342. Therefore, this unified assembly may be used to simply the alignment of the treatment radiation with respect to a malignant SPN identified by the optical imaging module 3320.

Figure 35:
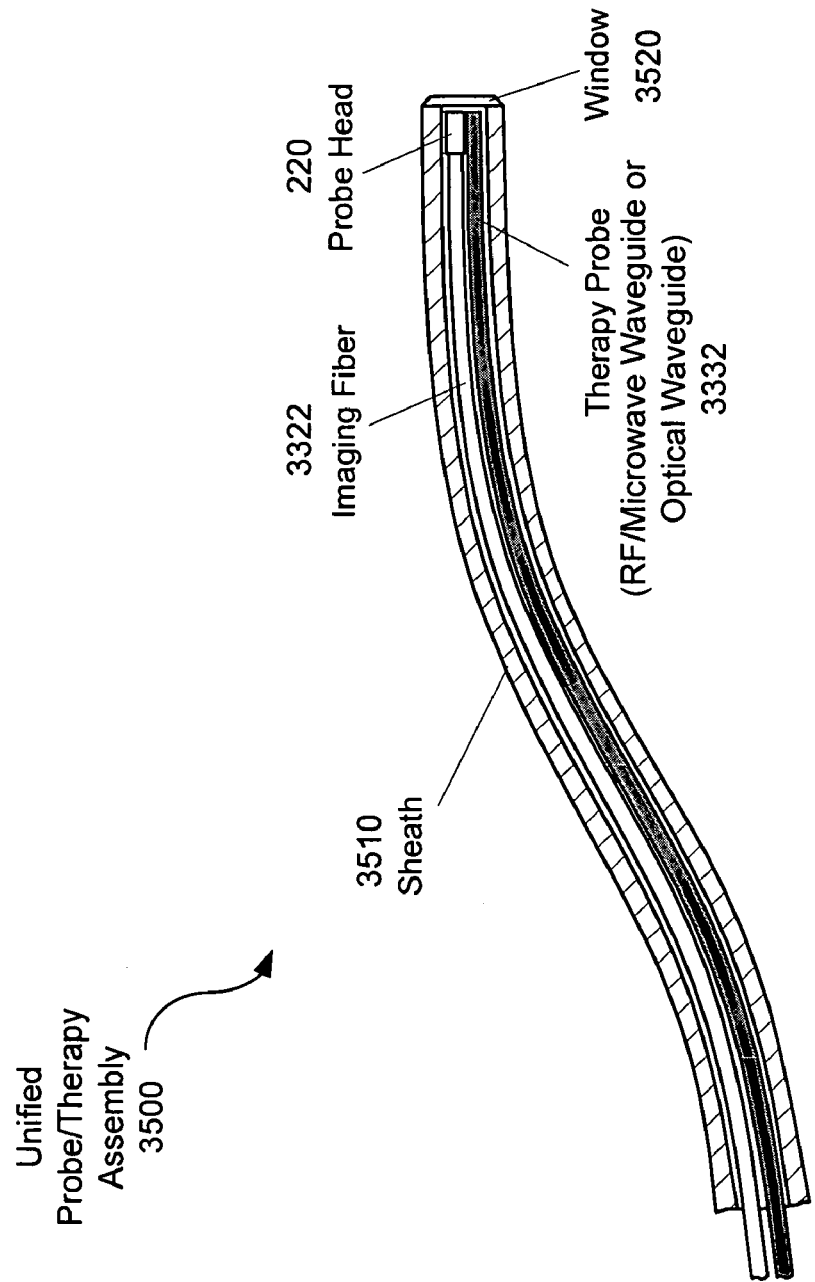
FIG. 35 shows a tubular unit or sheath for holding the probe fiber and the waveguide together as a single unit inserted inside the working channel shown in FIG. 33.

FIG. 35 shows one example of a unified assembly 3500. A tubular unit or sheath 3510 is used to hold the probe fiber 3322 and the waveguide 3332 together as a single unit. The probe head 220 at or near the end of the fiber 3322 and the distal end of the waveguide 3332 are placed next to each other at the distal end of the tubular unit 3510 within an end facet window 3520. As such, the probe head 220 and the distal end of the waveguide 3332 are aimed at the essentially the same location. The assembly 3500 is then inserted inside the working channel 3342 to place the end facet window 3520 at the end of the working channel 3342.

Only a few implementations are disclosed in this application. However, it is understood that variations, modifications and enhancements may be made.

What is claimed is what is described in the text and illustrated in the drawings, including:

1. A medical device, comprising:
    a bronchoscope comprising a working channel configured for insertion into a passage of a body to reach a target area inside the body;
    an optical fiber probe module comprising (1) a probe optic fiber having a portion inserted into the working channel of the bronchoscope and (2) an optical probe head coupled to an end of the probe optic fiber and located inside the working channel, the optical fiber probe module operable to direct probe light to and collect reflected light from the target area in the body through the probe optic fiber and the optical probe head and to obtain information of the target area from the collected reflected light; and
    a laser therapy module comprising a power delivery optic fiber having a portion inserted into the working channel of the bronchoscope to deliver a treatment laser beam to the target area,
    wherein the probe optic fiber is structured to support light in a first propagation mode and a second, different propagation mode, and the optical fiber probe module further comprises:
    a light source to produce the probe light, wherein the probe optic fiber receives and guides the probe light in the first propagation mode,
    wherein the optical probe head is coupled to the probe optic fiber to receive the light from the probe optic fiber and to reflect a first portion of the light back to the probe optic fiber in the first propagation mode and direct a second portion of the light to the targeted area, the probe head collecting reflection of the second portion from the target area and exporting to the probe optic fiber the reflection as a reflected second portion in the second propagation mode;
    an optical differential delay unit to produce and control a relative delay between the reflected first portion and the reflected second portion received from the probe optic fiber in response to a control signal;
    a detection module to receive the reflected first portion and the reflected second portion from the probe optic fiber and to extract information of the target area carried by the reflected second portion; and
    a control unit, which produces the control signal to the optical differential delay unit, to set the relative delay at two different bias values to select a layer of material inside the target area to measure an optical absorption of the selected layer.

2. The device as in claim 1, further comprising:
    a computed tomography (CT) module to scan at least a part of the body to obtain CT scan data of the scanned part of the body which is analyzed to identify and locate the target area suspicious of being malignant for further probing and analysis by the optical fiber probe module.

3. The device as in claim 1, wherein the detection module comprises:
    an optical device to direct light in the first propagation mode along a first optical path and light in the second propagation mode along a second, different optical path;
    a first optical element in the first optical path to separate light into a first set of different beams at different wavelengths;
    a plurality of first light detectors to respectively receive and detect the first set of different beams from the first optical element;
    a second optical element in the second optical path to separate light into a second set of different beams at the different wavelengths; and
    a plurality of second light detectors to respectively receive and detect the second set of different beams from the second optical element.

4. The device as in claim 3, wherein the first and second optical elements are optical gratings.

5. The device as in claim 1, wherein the detection module comprises a digital signal processor to process information of the target area in the reflected second portion and to generate spectral absorbance data of the target area.

6. The device as in claim 1, wherein the optical differential delay unit comprises:
    a mode splitting unit to separate received light into a first beam in the first propagation mode and a second beam in the second propagation mode; and a variable optical delay element in one of the first and the second beams to adjust an optical delay between the first and the second beams in response to the control signal.

7. The device as in claim 1, wherein the first and second propagation modes are two orthogonal polarization modes supported by the probe optic fiber, and wherein the detection module comprises:
an optical detector; and
an optical polarizer to receive and mix the reflected first and second portions to produce an optical output to the optical detector.

8. The device as in claim 1, wherein the optical probe head comprises a partial mode converter which sets the reflection from the target in the second propagation mode.

9. The device as in claim 1, wherein the optical probe head comprises:
a partial reflector to reflect the reflected first portion of the probe light and to transmit the second portion of the probe light to the sample; and
a polarization rotator located between the partial reflector and the target area to change a polarization of the reflected second portion in controlling the reflected second portion to be in the second propagation mode.

10. The device as in claim 1, wherein the optical probe head comprises:
a partial reflector to reflect the reflected first portion of the probe light and to transmit the second portion of the probe light to the target area; and
a Faraday rotator located between the partial reflector and the target area to change a polarization of the reflected second portion in controlling the reflected second portion to be in the second propagation mode.

11. The device as in claim 1, wherein the optical probe head comprises:
a partial reflector to reflect the reflected first portion of the probe light and to transmit the second portion of the probe light to the target area; and
a quarter wave plate located between the partial reflector and the target to change a polarization of the reflected second portion in controlling the reflected second portion to be in the second propagation mode.

12. The device as in claim 1, wherein the optical fiber probe module further comprises:
an input waveguide to receive the probe light from the light source and to guide the input beam in the first propagation mode;
an output waveguide to receive the reflected first and second portions from the probe optic fiber and to direct the reflected first and second portions to the optical differential delay unit; and
an optical router coupled to the input waveguide, the probe optic fiber, and the output waveguide, the optical router to direct light coming from the input waveguide to the probe optic fiber and light coming from the probe optic fiber to the output waveguide.

13. The device as in claim 12, wherein the optical router comprises:
an optical circulator;
a first beam splitter in the probe optic fiber to transmit light in the first propagation mode and to reflect light in the second propagation mode;
a second beam splitter in the output waveguide to transmit light in the first propagation mode and to reflect light in the second propagation mode; and
a bypass waveguide coupled between the first and the second beam splitters to direct the reflected second portion reflected by the first beam splitter to the second beam splitter which directs the reflected second portion into the output waveguide by reflection.

14. The device as in claim 12, further comprising a tunable optical filter located in one of the input waveguide, the probe optic fiber, and the output waveguide to select a portion of the spectral response of the target area to measure.

15. The device as in claim 1, further comprising a tunable optical filter to filter the probe light to select a portion of the spectral response of the target area to measure.

16. The device as in claim 1, further comprising a tunable optical filter to filter the reflected first and second portions to select a portion of the spectral response of the target area to measure.

17. A medical device, comprising:
a bronchoscope comprising a working channel configured for insertion into a passage of a body to reach a target area inside the body;
an optical fiber probe module comprising (1) a probe optic fiber having a portion inserted into the working channel of the bronchoscope and (2) an optical probe head coupled to an end of the probe optic fiber and located inside the working channel, the optical fiber probe module operable to direct probe light to and collect reflected light from the target area in the body through the probe optic fiber and the optical probe head and to obtain information of the target area from the collected reflected light; and
a laser therapy module comprising a power delivery optic fiber having a portion inserted into the working channel of the bronchoscope to deliver a treatment laser beam to the target area,
wherein the optical fiber probe module further comprises:
a plurality of light sources emitting light at different wavelength bands centered at different wavelengths as the probe light into the probe optic fiber, wherein the optical probe head reflects a first portion of the probe light back to the probe optic fiber in a first propagation mode and directs a second portion of the probe light to the target area, and wherein the probe head collects reflection of the second portion from the target area and exports to the probe optic fiber the reflection as a reflected second portion in a second propagation mode different from the first propagation mode;
an optical differential delay unit to produce and control a relative delay between the reflected first portion and the reflected second portion received from the single waveguide in response to a control signal;
a detection module to receive the reflected first portion and the reflected second portion and to extract information of the target area carried by the reflected second portion; and
a probe control unit, which produces the control signal to the optical differential delay unit, to set the relative delay at two different bias values to select a layer of material inside the target area to measure an optical absorption of the selected layer at each and every wavelength from the different light sources.

18. The device as in claim 17, further comprising:
a computed tomography (CT) module to scan at least a part of the body to obtain CT scan data of the scanned part of the body which is analyzed to identify and locate the target area suspicious of being malignant for further probing and analysis by the optical fiber probe module.

* * * * *

UNITED STATES PATENT AND TRADEMARK OFFICE
CERTIFICATE OF CORRECTION

| | | |
|---|---|---|
| PATENT NO. | : 7,970,458 B2 | Page 1 of 1 |
| APPLICATION NO. | : 11/253242 | |
| DATED | : June 28, 2011 | |
| INVENTOR(S) | : Peter E. Norris, Feiling Wang and Xiao-Li Li | |

It is certified that error appears in the above-identified patent and that said Letters Patent is hereby corrected as shown below:

In Column 26, Line 27, Equation (16) delete "$A_{II}(\lambda)=r_{II}e^{-\mu_g(\lambda)z_I-2\mu_h(\lambda)z_{II}}$," and insert -- $A_{II}(\lambda)=r_{II}e^{-2\mu_g(\lambda)z_I-2\mu_h(\lambda)z_{II}}$ --, therefor.

In Column 28, Line 36, delete "2110. the" and insert -- 2110. The --, therefor.

In Column 28, Line 61, delete "21110" and insert -- 2110 --, therefor.

In Column 33, Line 40, delete "map an" and insert -- map a --, therefor.

In Column 35, Line 44, delete "enabling an" and insert -- enabling a --, therefor.

In Column 36, Line 49, delete "The" and insert -- the --, therefor.

Signed and Sealed this
Second Day of October, 2012

David J. Kappos
*Director of the United States Patent and Trademark Office*